(12) United States Patent
Burkly et al.

(10) Patent No.: US 6,616,926 B1
(45) Date of Patent: Sep. 9, 2003

(54) METHODS OF MODULATING LIPID METABOLISM AND STORAGE

(75) Inventors: Linda Burkly, West Newton, MA (US); Li Chun Wang, North Grafton, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/704,917

(22) Filed: Nov. 2, 2000

Related U.S. Application Data

(63) Continuation of application No. PCT/US00/05662, filed on Mar. 3, 2000.
(60) Provisional application No. 60/122,640, filed on Mar. 3, 1999, and provisional application No. 60/124,446, filed on Mar. 15, 1999.

(51) Int. Cl.[7] ..................... A61K 39/395; A61K 38/00; G01N 33/566; C07K 1/00; C07H 21/04
(52) U.S. Cl. ................. 424/145.1; 424/130.1; 424/134.1; 424/138.1; 424/158.1; 435/7.21; 435/69.5; 436/501; 530/350; 530/388.22; 536/23.5
(58) Field of Search ........................... 514/2; 424/134.1, 424/138.1, 158.1, 130.1, 145.1; 435/7.21, 69.1; 436/501; 530/350, 388.22; 536/23.5

(56) References Cited

U.S. PATENT DOCUMENTS

| | | | |
|---|---|---|---|
| 4,588,585 A | 5/1986 | Mark et al. | |
| 4,868,116 A | 9/1989 | Morgan et al. | |
| 4,874,702 A | 10/1989 | Fiers et al. | |
| 4,980,286 A | 12/1990 | Morgan et al. | |
| 5,096,815 A | 3/1992 | Ladner et al. | |
| 5,122,464 A | 6/1992 | Wilson et al. | |
| 5,198,346 A | 3/1993 | Ladner et al. | |
| 5,223,409 A | 6/1993 | Ladner et al. | |
| 5,328,470 A | 7/1994 | Nabel et al. | |
| 5,747,641 A | 5/1998 | Frankel et al. | |
| 5,759,811 A | 6/1998 | Epstein et al. | |
| 5,789,650 A | 8/1998 | Lonberg et al. | |
| 5,798,230 A | 8/1998 | Bornkamm et al. | |

FOREIGN PATENT DOCUMENTS

| | | |
|---|---|---|
| EP | 412762 | 2/1991 |
| WO | WO 88/06630 | 9/1988 |
| WO | WO 89/02468 | 3/1989 |
| WO | WO 89/05345 | 6/1989 |
| WO | WO 89/07136 | 8/1989 |
| WO | WO 90/07861 | 7/1990 |
| WO | WO 91/06309 | 5/1991 |
| WO | WO 92/07573 | 5/1992 |
| WO | WO 92/09690 | 6/1992 |
| WO | WO 95/18856 | 7/1995 |
| WO | WO 95/23223 | 8/1995 |

OTHER PUBLICATIONS

Incardona et al., Development 125(3553–3562)1998.*
Chiag et al., Nature 383(407)1996.*
Bowie et al., 1990, Science 247:1306–1310.*
Agterberg et al., 1990, "Outer–membrane PhoE protein of *Escherichia coli* K–12 as an exposure vector: possibilities and limitations", Gene 88:37–45.
Apelqvist et al., 1997, "Sonic hedgehog directs specialised mesoderm differentiation in the intestine and pancreas", Curr. Biol. 7:801–804.
Armentano et al., 1990, "Expression of human factor IX in rabbit hepatocytes by retrovirus–mediated gene transfer: potential for gene therapy of hemophilia B", Proc. Natl. Acad. Sci. USA 87:6141–6145.
Barbas et al., 1992, "Semisynthetic combinatorial antibody libraries: a chemical solution to the diversity problem", Proc. Natl. Acad. .Sci. USA 89:4457–4461.
Berkner et al., 1988, "Development of adenovirus vectors for the expression of heterologous genes", Biotechniques 6:616–629.
Boerner et al., 1991, "Production of antigen–specific human monoclonal antibodies from in vitro–primed human splenocytes", J. Immunol. 147:86–95.
Breslow, 1996, "Mouse models of atherosclerosis", Science 272:685–688.
Callow et al., 1994, "Expression of human apolipoprotein B and assembly of lipoprotein(a) in transgenic mice", Proc. Natl. Acad. Sci. USA 91:2130–2134.
Chang et al., 1994, "Products, genetic linkage and limb patterning activity of a murine hedgehog gene", Development 120:3339–3353.
Charbit et al., 1986, "Probing the topology of a bacterial membrane protein by genetic insertion of a foreign epitope; expression at the cell surface", EMBO J. 5:3029–3037.
Chen et al., "Gene therapy for brain tumors: regression of experimental gliomas by adenovirus–mediated gene transfer in vivo", Proc. Natl. Acad. Sci. USA 91:3054–3057.
Chowdhury et al. 1991, "Long–term improvement of hypercholesterolemia after ex vivo gene therapy in LDLR–deficient rabbits", Science 254:1802–1805.
Clackson et al., 1991, "Making antibody fragments using phage display libraries", Nature 352:624–628.

(List continued on next page.)

*Primary Examiner*—Yvonne Eyler
*Assistant Examiner*—Michael Brannock
(74) *Attorney, Agent, or Firm*—Ropes & Gray LLP

(57) ABSTRACT

Anti-hedgehog antibodies directed at blocking the binding of hedgehog to its receptor patched-1, will impair lipid metabolism and storage. This invention presents methods for the treatment of a variety of lipid metabolism and lipid storage disorders, aberrant apolipoprotein expression, atherosclerosis and other lipid associated disorders using lipid modulators such as hedgehog antagonists or hedgehog agonists.

8 Claims, 2 Drawing Sheets

OTHER PUBLICATIONS

Co et al., 1991, "Humanized antibodies for antiviral therapy", Proc. Natl. Acad. Sci. USA 88:2869–2873.

Cull et al., 1992, "Screening for receptor ligands using large libraries of peptides linked to the C terminus of the lac repressor", Proc. Natl. Acad. Sci. USA 89:1865–1869.

Cunningham and Wells, 1989, "High–resolution epitope mapping of hGH–receptor interactions by alanine–scanning mutagenesis", Science 244:1081–1085.

Cwirla et al., 1990, "Peptides on phage: a vast library of peptides for identifying ligands", Proc. Natl. Acad. Sci. USA 87:6378–6382.

Dai et al., 1992, "Gene therapy via primary myoblasts: long–term expression of factor IX protein following transplantation in vivo", Proc. Natl. Acad. Sci. USA 89:10892–10895.

Dann et al., 1986, "Human renin: a new class of inhibitors", Biochem. Biophys. Res. Commun. 134:71–77.

Danos and Mulligan, 1988, "Safe and efficient generation of recombinant retroviruses with amphotropic and ecotropic host ranges", Proc. Natl. Acad. Sci. USA 85:6460–6464.

Devlin et al., 1990, "Random peptide libraries: a source of specific protein binding molecules", Science 249:404–406.

Echelard et al., 1993, "Sonic hedgehog, a member of a family of putative signaling molecules, is implicated in the regulation of CNS polarity", Cell 75:1417–1430.

Eglitis et al., 1985, "Gene expression in mice after high efficiency retroviral–mediated gene transfer", Science 230:1395–1398.

Ekker et al., 1995, "Patterning activities of vertabrate hedgehog proteins in the developing eye and brain", Curr. Biol. 5:944–955.

Fan et al., 1995, "Long–range sclerotome induction by sonic hedgehog: direct role of the amino–terminal cleavage product and modulation by the cyclic AMP signaling pathway", Cell 81:457–654.

Fancy et al., 1996, "New chemistry for the study of multiprotein complexes: the six–histidine tag as a receptor for a protein crosslinking reagent", Chem. Biol. 3:551–559.

Farese et al, 1995, "Knockout of the mouse apolipoprotein B gene results in embryonic lethality in homozygotes and protection against diet–induced hypercholesterolemia in heterozygotes", Proc. Natl. Acad. Sci. USA 92:1774–1778.

Ferry et al., 1991, "Retroviral–mediated gene transfer into hepatocytes in vivo", Proc. Natl. Acad. Sci. USA 88:8377–8381.

Flotte et al., 1993, Expression of the cystic fibrosis transmembrane conductance regulator from a novel adeno–associated virus promoter, J. Biol. Chem. 268:3781–3790.

Gordon et al., 1985, "Design of peptide derived amino alcohols as transition–state analog inhibitors of angiotensin converting enzyme", Biochem. Biophys. Res. Commun. 126:419–426.

Griffiths et al., 1993, "Human anti–self antibodies with high specificity from phage display libraries", Embo J. 12:725–734.

Gross and Witkip, 1961, "Selective cleavage of the methionyl peptide bonds in ribonuclease with cyanogen bromide", J. Am. Chem. Soc. 83:1510.

Hall et al., 1995, "A potential catalytic site revealed by the 1.7–A crystal structure of the amino–terminal signalling domain of Sonic hedgehog", Nature 378:212–216.

Hansson et al., 1992, "Expression of recombinant proteins on the surface of the coagulase–nagative bacterium *Staphylococcus xylosus*", J. Bacteriol. 174:4239–4245.

Hermonat et al., 1984, "Use of adeno–associated virus as a mammalian DNA cloning vector: transduction of neomycin resistance into mammalian tissue culture cells", Proc. Natl. Acad. Sci. USA 81:6466–6470.

Homanics et al., 1993, Targeted modification of the apolipoprotein B gene results in hypobetalipoproteinemia and developmental abnormalities in mice, Proc. Natl. Acad. Sci. USA 90:2389–2393.

Huang and Stoller, 1991, "Construction of representative immunoglobulin variable region cDNA libraries from human peripheral blood lymphocytes without in vitro stimulation", J. Immunol. Methods 141:227–236.

Huber et al., 1991, "Retroviral–mediated gene therapy for the treatment of hepatocellular carcinoma: an innovative approach for cancer therapy", Proc. Natl. Acad. Sci. USA 88:8039–8043.

Hwu et al., 1993, "Functional and molecular characterization of tumor–infiltrating lymphocytes transduced with tumor necrosis factor–alpha cDNA for the gene therapy of cancer in humans", J. Immunol. 150:4104–4115.

Ike et al., 1983, "Solid phase synthesis of polynucleotides. VIII. Synthesis of mixed oligodeoxyribonucleotides by the phosphotriester solid phase method", Nucleic Acids Res. 11:477–488.

Itakura et al., 1981, Recombinant DNA, Proc. $3^{rd}$ Cleveland Symposium On Macromolecules, A.G. Walton, ed. (Elsevier, Amsterdam) pp. 273–289.

Itakura et al., 1984, "Expression in *Escherichia coli* of a chemically synthesized gene for the hormone somatostatin", Science 198:1056–1063.

Itakura et al., 1984, "Synthesis and use of synthetic oligonucleotides", Annu. Rev. Biochem. 53:323–356.

Jones et al., 1986, "Replacing the complementarity–determining regions in a human antibody with those from a mouse", Nature 321:522–525.

Kaufman and Sharp, 1982, "Construction of a modular dihydrofolate reductase cDNA gene: analysis of signals utilized for efficient expression", Mol. Cell. Biol. 2:1304–1319.

Kay et al., 1992, "Hepatic gene therapy: persistent expression of human alpha 1–antitrypsin in mice after direct gene delivery in vivo", Hum. Gene Ther. 3:641–647.

Kinto et al., 1997, "Fibroblasts expressing Sonic hedgehog induce osteoblast differentiation and ectopic bone formation", FEBS Lett. 404:319–323.

Klauser et al., 1990, "Extracellular transport of cholera toxin B subunit using Neisseria IgA protease beta–domain: conformation–dependent outer membrane translocation", EMBO J. 9:1991–1999.

Kohler et al., 1975, "Continuous cultures of fused cells secreting antibody of predefined specificity", Nature 256:495–497.

Kuwajima et al., 1988, "Presentation of an antigenic determinant from hen egg–white lysozyme on the flagellar filament of Escherichia coli", Bio/Tech. 6:1080–1083.

Leung et al., 1989, "A method for random mutagenesis of a defined DNA segment using a modified polymerase chain reaction", Technique 1:11–15.

Lindley, 1956, "A new synthetic substrate for trypsin and its application to the determination of the amino–acid sequence of proteins", Nature 178:647.

Linton et al., 1993, "Familial hypobetalipoproteinemia", J. Lipid Res. 34:521–541.

Litingtung et al., 1998, "Sonic hedgehog is essential to foregut development", Nat. Genet. 20:58–61.

Mark et al, 1984, "Site-specific mutagenesis of the human fibroblast interferon gene", Proc. Natl. Acad. Sci. USA 81:5662–5666.

Marks et al., 1992, "Molecular evolution of proteins on filamentous phage. Mimicking the strategy of the immune system", J. Biol. Chem. 267:16007–16010.

McCormick et al., 1996, "Transgenic mice that overexpress mouse apolipoprotein B. Evidence that the DNA sequences controlling intestinal expression of the apolipoprotein B gene are distant from the structural gene", J. Biol Chem. 271:11963–11970.

Merrifield, 1967, "New approaches to the chemical synthesis of peptides", Recent Prog. Horm. Res23:451–482.

Miller, 1990, "Progress toward human gene therapy", Blood 76:271–278.

Mohler and Vani, 1992, "Molecular organization and embryonic expression of the hedgehog gene involved in cell–cell communication in segmental patterning of Drosophila", Development 115:957–971.

Muzyczka et al., 1992, "Use of adeno-associated virus as a general transduction vector for mammalian cells", Curr. Top. Microbiol. Immunol. 158:97–129.

Myers et al., 1985, "A general method for saturation mutagenesis of cloned DNA fragments", Science229:242–247.

Narang, 1983, "DNA synthesis", Tetrahedron 39:3–22.

Needleman et al., 1970, "A general method applicable to the search for similarities in the amino acid sequence of two proteins", J. Mol. Biol. 48:443–453.

Orlandi et al., 1989, "Cloning immunoglobulin variable domains for expression by the polymerase chain reaction", Proc. Natl. Acad. Sci. USA 86:3833–3837.

Persson et al., 1991, "Generation of diverse high–affinity human monoclonal antibodies by repertoire cloning", Proc. Natl. Acad. Sci. USA 88:2432–2436.

Powell-Braxton et al., 1998, "A mouse model of human familial hypercholesterolemia: markedly elevated low density lipoprotein cholesterol levels and severe atherosclerosis on a low–fat chow diet", Nat. Med. 4:934–938.

Purcell-Huynh et al., 1995, "Transgenic mice expressing high levels of human apolipoprotein B develop severe atherosclerotic lesions in response to a high–fat diet", J. Clin. Invest. 9:2246–2257 PMID: 7738190.

Queen et al., 1989, "A humanized antibody that binds to the interleukin 2 receptor", Proc. Natl. Acad. Sci. USA 86:10029–10033.

Riechmann et al., 1988, "Reshaping human antibodies for therapy", Nature 332:323–327.

Roberts et al., 1992, "Directed evolution of a protein: selection of potent neutrophil elastase inhibitors displayed on M13 fusion phage", Proc. Natl. Acad. Sci. USA 89:2429–2433.

Rosenfeld et al., 1991, "Adenovirus-mediated transfer of a recombinant alpha 1–antitrypsin gene to the lung epithelium in vivo", Science 252:431–434.

Rosenfeld et al., 1992, "In vivo transfer of the human cystic fibrosis transmembrane conductance regulator gene to the airway epithelium", Cell 68:143–155.

Sato et al., 1986, "Synthesis and antibiotic activity of a gramicidin s analogue containing bicyclic beta–turn dipeptides", J. Chem. Soc. Perkin Trans. 1:1231.

Schorr et al., 1991, "Surface expression of malarial antigens in Salmonella typhimurium: induction of serum antibody response upon oral vaccination of mice", Vaccine 9:675–681.

Scott et al., 1990, "Searching for peptide ligands with an epitope library", Science 249:386–390.

Scully et al., 1992, Case records of the Massachusetts General Hospital. Weekly clinicopathological excercises. Case 35–1992. An eight–month–old boy with diarrhea and failure to thrive. N. Engl. J. Med. 327:628–635.

Taylor and Jones, 1979, "Multiple new phenotypes induced in 10T1/2 and 3T3 cells treated with 5–azacytidine", Cell 17:771–779.

Tempest, 1991, "Reshaping a human monoclonal antibody to inhibit human respiratory syncytial virus infection in vivo", Biotechnology (N Y) 9:266–271.

Thiry et al., 1989, "Cloning of DNA sequences encoding foreign peptides and their expression in the K88 pili", Appl. Environ. Microbiol. 55:984–993.

Tratschin et al., 1984, "A human parvovirus, adeno-associated virus, as a eucaryotic vector: transient expression and encapsidation of the procaryotic gene for chloramphenicol acetyltransferase", Mol. Cell. Biol. 4:2072–2081.

Van Beusechem et al., 1992, "Long–term expression of human adenosine deaminase in rhesus monkeys transplanted with retrovirsus–infected bone–marrow cells", Proc. Natl. Acad. Sci. USA 89:7640–7644.

Verhoeyen et al., 1988, "Reshaping human antibodies: grafting an antilysozyme activity", Science 239:1534–1536.

Wang et al., 1993, "Bone morphogenetic protein–2 causes commitment and differentiation in C3H10T1/2 and 3T3 cells", Growth Factors 9:57–71.

Wells et al., 1985, "Cassette mutagenesis: an efficient method for generation of multiple mutations at defined sites", Gene 34:315–323.

Wilson et al., 1988, "Retrovirus–mediated transduction of adult hepatocytes", Proc. Natl. Acad. Sci. USA 85:3014–3018.

Wondisford et al., 1988, "Cloning of the human thyrotropin beta–subunit gene and transient expression of biologically active human thyrotropin after gene transfection", Mol. Endocrinol. 2:32–9.

Yang et al., 1997, "Expression of human GLI in mice results in failure to thrive, early death, and patchy Hirschsprung-like gastrointestinal dilatation", Mol. Med. 3:826–835.

Young et al, 1995, "A genetic model for absent chylomicron formation: mice producing apolipoprotein B in the liver, but not in the intestine", J. Clin. Invest 96:2932–2946.

* cited by examiner

High-Fat Diet Dependent Weight Loss in Anti-hh mAb Treated Mice

SEQUENCE LISTING

```
<160> NUMBER OF SEQ ID NOS:  22

<210> SEQ ID NO 1
<211> LENGTH: 1277
<212> TYPE: DNA
<213> ORGANISM: Gallus sp.
<220> FEATURE:
<221> NAME/KEY: CDS
<222> LOCATION: (1)..(1275)

<400> SEQUENCE: 1 atg gtc gaa atg ctg ctg ttg aca aga att ctc ttg gtg ggc ttc atc        48
Met Val Glu Met Leu Leu Leu Thr Arg Ile Leu Leu Val Gly Phe Ile
  1               5                  10                  15 tgc gct ctt tta gtc tcc tct ggg ctg act tgt gga cca ggc agg ggc        96
Cys Ala Leu Leu Val Ser Ser Gly Leu Thr Cys Gly Pro Gly Arg Gly
             20                  25                  30 att gga aaa agg agg cac ccc aaa aag ctg acc ccg tta gcc tat aag       144
Ile Gly Lys Arg Arg His Pro Lys Lys Leu Thr Pro Leu Ala Tyr Lys
         35                  40                  45 cag ttt att ccc aat gtg gca gag aag acc cta ggg gcc agt gga aga       192
Gln Phe Ile Pro Asn Val Ala Glu Lys Thr Leu Gly Ala Ser Gly Arg
```

-continued

| | | |
|---|---|---|
| tat gaa ggg aag atc aca aga aac tcc gag aga ttt aaa gaa cta acc<br>Tyr Glu Gly Lys Ile Thr Arg Asn Ser Glu Arg Phe Lys Glu Leu Thr<br>65                             70                        75                      80 | 240 |

```
         50                          55                          60
tat gaa ggg aag atc aca aga aac tcc gag aga ttt aaa gaa cta acc        240
Tyr Glu Gly Lys Ile Thr Arg Asn Ser Glu Arg Phe Lys Glu Leu Thr
 65                  70                  75                  80 cca aat tac aac cct gac att att ttt aag gat gaa gag aac acg gga        288
Pro Asn Tyr Asn Pro Asp Ile Ile Phe Lys Asp Glu Glu Asn Thr Gly
                 85                  90                  95 gct gac aga ctg atg act cag cgc tgc aag gac aag ctg aat gcc ctg        336
Ala Asp Arg Leu Met Thr Gln Arg Cys Lys Asp Lys Leu Asn Ala Leu
                100                 105                 110 gcg atc tcg gtg atg aac cag tgg ccc ggg gtg aag ctg cgg gtg acc        384
Ala Ile Ser Val Met Asn Gln Trp Pro Gly Val Lys Leu Arg Val Thr
            115                 120                 125 gag ggc tgg gac gag gat ggc cat cac tcc gag gaa tcg ctg cac tac        432
Glu Gly Trp Asp Glu Asp Gly His His Ser Glu Glu Ser Leu His Tyr
        130                 135                 140 gag ggt cgc gcc gtg gac atc acc acg tcg gat cgg gac cgc agc aag        480
Glu Gly Arg Ala Val Asp Ile Thr Thr Ser Asp Arg Asp Arg Ser Lys
145                 150                 155                 160 tac gga atg ctg gcc cgc ctc gcc gtc gag gcc ggc ttc gac tgg gtc        528
Tyr Gly Met Leu Ala Arg Leu Ala Val Glu Ala Gly Phe Asp Trp Val
                165                 170                 175 tac tac gag tcc aag gcg cac atc cac tgc tcc gtc aaa gca gaa aac        576
Tyr Tyr Glu Ser Lys Ala His Ile His Cys Ser Val Lys Ala Glu Asn
                180                 185                 190 tca gtg gca gcg aaa tca gga ggc tgc ttc cct ggc tca gcc aca gtg        624
Ser Val Ala Ala Lys Ser Gly Gly Cys Phe Pro Gly Ser Ala Thr Val
            195                 200                 205 cac ctg gag cat gga ggc acc aag ctg gtg aag gac ctg agc cct ggg        672
His Leu Glu His Gly Gly Thr Lys Leu Val Lys Asp Leu Ser Pro Gly
        210                 215                 220 gac cgc gtg ctg gct gct gac gcg gac ggc cgg ctg ctc tac agt gac        720
Asp Arg Val Leu Ala Ala Asp Ala Asp Gly Arg Leu Leu Tyr Ser Asp
225                 230                 235                 240 ttc ctc acc ttc ctc gac cgg atg gac agc tcc cga aag ctc ttc tac        768
Phe Leu Thr Phe Leu Asp Arg Met Asp Ser Ser Arg Lys Leu Phe Tyr
                245                 250                 255 gtc atc gag acg cgg cag ccc cgg gcc cgg ctg cta ctg acg gcg gcc        816
Val Ile Glu Thr Arg Gln Pro Arg Ala Arg Leu Leu Leu Thr Ala Ala
                260                 265                 270 cac ctg ctc ttt gtg gcc ccc cag cac aac cag tcg gag gcc aca ggg        864
His Leu Leu Phe Val Ala Pro Gln His Asn Gln Ser Glu Ala Thr Gly
            275                 280                 285 tcc acc agt ggc cag gcg ctc ttc gcc agc aac gtg aag cct ggc caa        912
Ser Thr Ser Gly Gln Ala Leu Phe Ala Ser Asn Val Lys Pro Gly Gln
        290                 295                 300 cgt gtc tat gtg ctg ggc gag ggc ggg cag cag ctg ctg ccg gcg tct        960
Arg Val Tyr Val Leu Gly Glu Gly Gly Gln Gln Leu Leu Pro Ala Ser
305                 310                 315                 320 gtc cac agc gtc tca ttg cgg gag gag gcg tcc gga gcc tac gcc cca       1008
Val His Ser Val Ser Leu Arg Glu Glu Ala Ser Gly Ala Tyr Ala Pro
                325                 330                 335 ctc acc gcc cag ggc acc atc ctc atc aac cgg gtg ttg gcc tcc tgc       1056
Leu Thr Ala Gln Gly Thr Ile Leu Ile Asn Arg Val Leu Ala Ser Cys
                340                 345                 350 tac gcc gtc atc gag gag cac agt tgg gcc cat tgg gcc ttc gca cca       1104
Tyr Ala Val Ile Glu Glu His Ser Trp Ala His Trp Ala Phe Ala Pro
            355                 360                 365 ttc cgc ttg gct cag ggg ctg ctg gcc gcc ctc tgc cca gat ggg gcc       1152
```

```
Phe Arg Leu Ala Gln Gly Leu Leu Ala Ala Leu Cys Pro Asp Gly Ala
        370             375                 380 atc cct act gcc gcc acc acc acc act ggc atc cat tgg tac tca cgg      1200
Ile Pro Thr Ala Ala Thr Thr Thr Thr Gly Ile His Trp Tyr Ser Arg
385                 390                 395                 400 ctc ctc tac cgc atc ggc agc tgg gtg ctg gat ggt gac gcg ctg cat      1248
Leu Leu Tyr Arg Ile Gly Ser Trp Val Leu Asp Gly Asp Ala Leu His
                405                 410                 415 ccg ctg ggc atg gtg gca ccg gcc agc tg                               1277
Pro Leu Gly Met Val Ala Pro Ala Ser
            420                 425

<210> SEQ ID NO 2
<211> LENGTH: 1190
<212> TYPE: DNA
<213> ORGANISM: Murine sp.
<220> FEATURE:
<221> NAME/KEY: CDS
<222> LOCATION: (1)..(1188)

<400> SEQUENCE: 2 atg gct ctg ccg gcc agt ctg ttg ccc ctg tgc tgc ttg gca ctc ttg       48
Met Ala Leu Pro Ala Ser Leu Leu Pro Leu Cys Cys Leu Ala Leu Leu
1               5                   10                  15 gca cta tct gcc cag agc tgc ggg ccg ggc cga gga ccg gtt ggc cgg       96
Ala Leu Ser Ala Gln Ser Cys Gly Pro Gly Arg Gly Pro Val Gly Arg
                20                  25                  30 cgg cgt tat gtg cgc aag caa ctt gtg cct ctg cta tac aag cag ttt      144
Arg Arg Tyr Val Arg Lys Gln Leu Val Pro Leu Leu Tyr Lys Gln Phe
            35                  40                  45 gtg ccc agt atg ccc gag cgg acc ctg ggc gcg agt ggg cca gcg gag      192
Val Pro Ser Met Pro Glu Arg Thr Leu Gly Ala Ser Gly Pro Ala Glu
        50                  55                  60 ggg agg gta aca agg ggg tcg gag cgc ttc cgg gac ctc gta ccc aac      240
Gly Arg Val Thr Arg Gly Ser Glu Arg Phe Arg Asp Leu Val Pro Asn
65                  70                  75                  80 tac aac ccc gac ata atc ttc aag gat gag gag aac agc ggc gca gac      288
Tyr Asn Pro Asp Ile Ile Phe Lys Asp Glu Glu Asn Ser Gly Ala Asp
                85                  90                  95 cgc ctg atg aca gag cgt tgc aaa gag cgg gtg aac gct cta gcc atc      336
Arg Leu Met Thr Glu Arg Cys Lys Glu Arg Val Asn Ala Leu Ala Ile
            100                 105                 110 gcg gtg atg aac atg tgg ccc gga gta cgc cta cgt gtg act gaa ggc      384
Ala Val Met Asn Met Trp Pro Gly Val Arg Leu Arg Val Thr Glu Gly
        115                 120                 125 tgg gac gag gac ggc cac cac gca cag gat tca ctc cac tac gaa ggc      432
Trp Asp Glu Asp Gly His His Ala Gln Asp Ser Leu His Tyr Glu Gly
130                 135                 140 cgt gcc ttg gac atc acc acg tct gac cgt gac cgt aat aag tat ggt      480
Arg Ala Leu Asp Ile Thr Thr Ser Asp Arg Asp Arg Asn Lys Tyr Gly
145                 150                 155                 160 ttg ttg gcg cgc cta gct gtg gaa gcc gga ttc gac tgg gtc tac tac      528
Leu Leu Ala Arg Leu Ala Val Glu Ala Gly Phe Asp Trp Val Tyr Tyr
                165                 170                 175 gag tcc cgc aac cac atc cac gta tcg gtc aaa gct gat aac tca ctg      576
Glu Ser Arg Asn His Ile His Val Ser Val Lys Ala Asp Asn Ser Leu
            180                 185                 190 gcg gtc cga gcc gga ggc tgc ttt ccg gga aat gcc acg gtg cgc ttg      624
Ala Val Arg Ala Gly Gly Cys Phe Pro Gly Asn Ala Thr Val Arg Leu
        195                 200                 205 cgg agc ggc gaa cgg aag ggg ctg agg gaa cta cat cgt ggt gac tgg      672
```

-continued

```
Arg Ser Gly Glu Arg Lys Gly Leu Arg Glu Leu His Arg Gly Asp Trp
    210                 215                 220 gta ctg gcc gct gat gca gcg ggc cga gtg gta ccc acg cca gtg ctg      720
Val Leu Ala Ala Asp Ala Ala Gly Arg Val Val Pro Thr Pro Val Leu
225                 230                 235                 240 ctc ttc ctg gac cgg gat ctg cag cgc cgc gcc tcg ttc gtg gct gtg      768
Leu Phe Leu Asp Arg Asp Leu Gln Arg Arg Ala Ser Phe Val Ala Val
                245                 250                 255 gag acc gag cgg cct ccg cgc aaa ctg ttg ctc aca ccc tgg cat ctg      816
Glu Thr Glu Arg Pro Pro Arg Lys Leu Leu Leu Thr Pro Trp His Leu
            260                 265                 270 gtg ttc gct gct cgc ggg cca gcg cct gct cca ggt gac ttt gca ccg      864
Val Phe Ala Ala Arg Gly Pro Ala Pro Ala Pro Gly Asp Phe Ala Pro
        275                 280                 285 gtg ttc gcg cgc cgc tta cgt gct ggc gac tcg gtg ctg gct ccc ggc      912
Val Phe Ala Arg Arg Leu Arg Ala Gly Asp Ser Val Leu Ala Pro Gly
        290                 295                 300 ggg gac gcg ctc cag ccg gcg cgc gta gcc cgc gtg gcg cgc gag gaa      960
Gly Asp Ala Leu Gln Pro Ala Arg Val Ala Arg Val Ala Arg Glu Glu
305                 310                 315                 320 gcc gtg ggc gtg ttc gca ccg ctc act gcg cac ggg acg ctg ctg gtc     1008
Ala Val Gly Val Phe Ala Pro Leu Thr Ala His Gly Thr Leu Leu Val
                325                 330                 335 aac gac gtc ctc gcc tcc tgc tac gcg gtt cta gag agt cac cag tgg     1056
Asn Asp Val Leu Ala Ser Cys Tyr Ala Val Leu Glu Ser His Gln Trp
            340                 345                 350 gcc cac cgc gcc ttc gcc cct ttg cgg ctg ctg cac gcg ctc ggg gct     1104
Ala His Arg Ala Phe Ala Pro Leu Arg Leu Leu His Ala Leu Gly Ala
        355                 360                 365 ctg ctc cct ggg ggt gca gtc cag ccg act ggc atg cat tgg tac tct     1152
Leu Leu Pro Gly Gly Ala Val Gln Pro Thr Gly Met His Trp Tyr Ser
370                 375                 380 cgc ctc ctt tac cgc ttg gcc gag gag tta atg ggc tg                  1190
Arg Leu Leu Tyr Arg Leu Ala Glu Glu Leu Met Gly
385                 390                 395

<210> SEQ ID NO 3
<211> LENGTH: 1281
<212> TYPE: DNA
<213> ORGANISM: Murine sp.
<220> FEATURE:
<221> NAME/KEY: CDS
<222> LOCATION: (1)..(1233)

<400> SEQUENCE: 3 atg tct ccc gcc tgg ctc cgg ccc cga ctg cgg ttc tgt ctg ttc ctg       48
Met Ser Pro Ala Trp Leu Arg Pro Arg Leu Arg Phe Cys Leu Phe Leu
1               5                   10                  15 ctg ctg ctg ctt ctg gtg ccg gcg gcg cgg ggc tgc ggg ccg ggc cgg       96
Leu Leu Leu Leu Leu Val Pro Ala Ala Arg Gly Cys Gly Pro Gly Arg
                20                  25                  30 gtg gtg ggc agc cgc cgg agg ccg cct cgc aag ctc gtg cct ctt gcc      144
Val Val Gly Ser Arg Arg Arg Pro Pro Arg Lys Leu Val Pro Leu Ala
            35                  40                  45 tac aag cag ttc agc ccc aac gtg ccg gag aag acc ctg ggc gcc agc      192
Tyr Lys Gln Phe Ser Pro Asn Val Pro Glu Lys Thr Leu Gly Ala Ser
    50                  55                  60 ggg cgc tac gaa ggc aag atc gcg cgc agc tct gag cgc ttc aaa gag      240
Gly Arg Tyr Glu Gly Lys Ile Ala Arg Ser Ser Glu Arg Phe Lys Glu
65                  70                  75                  80 ctc acc ccc aac tac aat ccc gac atc atc ttc aag gac gag gag aac      288
```

```
Leu Thr Pro Asn Tyr Asn Pro Asp Ile Ile Phe Lys Asp Glu Glu Asn
            85                  90                  95 acg ggt gcc gac cgc ctc atg acc cag cgc tgc aag gac cgt ctg aac       336
Thr Gly Ala Asp Arg Leu Met Thr Gln Arg Cys Lys Asp Arg Leu Asn
        100                 105                 110 tca ctg gcc atc tct gtc atg aac cag tgg cct ggt gtg aaa ctg cgg       384
Ser Leu Ala Ile Ser Val Met Asn Gln Trp Pro Gly Val Lys Leu Arg
            115                 120                 125 gtg acc gaa ggc cgg gat gaa gat ggc cat cac tca gag gag tct tta       432
Val Thr Glu Gly Arg Asp Glu Asp Gly His His Ser Glu Glu Ser Leu
        130                 135                 140 cac tat gag ggc cgc gcg gtg gat atc acc acc tca gac cgt gac cga       480
His Tyr Glu Gly Arg Ala Val Asp Ile Thr Thr Ser Asp Arg Asp Arg
145                 150                 155                 160 aat aag tat gga ctg ctg gcg cgc tta gca gtg gag gcc ggc ttc gac       528
Asn Lys Tyr Gly Leu Leu Ala Arg Leu Ala Val Glu Ala Gly Phe Asp
                165                 170                 175 tgg gtg tat tac gag tcc aag gcc cac gtg cat tgc tct gtc aag tct       576
Trp Val Tyr Tyr Glu Ser Lys Ala His Val His Cys Ser Val Lys Ser
            180                 185                 190 gag cat tcg gcc gct gcc aag aca ggt ggc tgc ttt cct gcc gga gcc       624
Glu His Ser Ala Ala Ala Lys Thr Gly Gly Cys Phe Pro Ala Gly Ala
        195                 200                 205 cag gtg cgc cta gag aac ggg gag cgt gtg gcc ctg tca gct gta aag       672
Gln Val Arg Leu Glu Asn Gly Glu Arg Val Ala Leu Ser Ala Val Lys
    210                 215                 220 cca gga gac cgg gtg ctg gcc atg ggg gag gat ggg acc ccc acc ttc       720
Pro Gly Asp Arg Val Leu Ala Met Gly Glu Asp Gly Thr Pro Thr Phe
225                 230                 235                 240 agt gat gtg ctt att ttc ctg gac cgc gag cca aac cgg ctg aga gct       768
Ser Asp Val Leu Ile Phe Leu Asp Arg Glu Pro Asn Arg Leu Arg Ala
                245                 250                 255 ttc cag gtc atc gag act cag gat cct ccg cgt cgg ctg gcg ctc acg       816
Phe Gln Val Ile Glu Thr Gln Asp Pro Pro Arg Arg Leu Ala Leu Thr
            260                 265                 270 cct gcc cac ctg ctc ttc att gcg gac aat cat aca gaa cca gca gcc       864
Pro Ala His Leu Leu Phe Ile Ala Asp Asn His Thr Glu Pro Ala Ala
        275                 280                 285 cac ttc cgg gcc aca ttt gcc agc cat gtg caa cca ggc caa tat gtg       912
His Phe Arg Ala Thr Phe Ala Ser His Val Gln Pro Gly Gln Tyr Val
    290                 295                 300 ctg gta tca ggg gta cca ggc ctc cag cct gct cgg gtg gca gct gtc       960
Leu Val Ser Gly Val Pro Gly Leu Gln Pro Ala Arg Val Ala Ala Val
305                 310                 315                 320 tcc acc cac gtg gcc ctt ggg tcc tat gct cct ctc aca agg cat ggg      1008
Ser Thr His Val Ala Leu Gly Ser Tyr Ala Pro Leu Thr Arg His Gly
                325                 330                 335 aca ctt gtg gtg gag gat gtg gtg gcc tcc tgc ttt gca gct gtg gct      1056
Thr Leu Val Val Glu Asp Val Val Ala Ser Cys Phe Ala Ala Val Ala
            340                 345                 350 gac cac cat ctg gct cag ttg gcc ttc tgg ccc ctg cga ctg ttt ccc      1104
Asp His His Leu Ala Gln Leu Ala Phe Trp Pro Leu Arg Leu Phe Pro
        355                 360                 365 agt ttg gca tgg ggc agc tgg acc cca agt gag ggt gtt cac tcc tac      1152
Ser Leu Ala Trp Gly Ser Trp Thr Pro Ser Glu Gly Val His Ser Tyr
    370                 375                 380 cct cag atg ctc tac cgc ctg ggg cgt ctc ttg cta gaa gag agc acc      1200
Pro Gln Met Leu Tyr Arg Leu Gly Arg Leu Leu Leu Glu Glu Ser Thr
385                 390                 395                 400
```

-continued

```
ttc cat cca ctg ggc atg tct ggg gca gga agc tgaagggact ctaaccactg    1253
Phe His Pro Leu Gly Met Ser Gly Ala Gly Ser
            405                 410 ccctcctgga actgctgtgc gtggatcc                                        1281
```

<210> SEQ ID NO 4
<211> LENGTH: 1313
<212> TYPE: DNA
<213> ORGANISM: Murine sp.
<220> FEATURE:
<221> NAME/KEY: CDS
<222> LOCATION: (1)..(1311)

<400> SEQUENCE: 4

```
atg ctg ctg ctg ctg gcc aga tgt ttt ctg gtg atc ctt gct tcc tcg     48
Met Leu Leu Leu Leu Ala Arg Cys Phe Leu Val Ile Leu Ala Ser Ser
  1               5                  10                  15 ctg ctg gtg tgc ccc ggg ctg gcc tgt ggg ccc ggc agg ggg ttt gga     96
Leu Leu Val Cys Pro Gly Leu Ala Cys Gly Pro Gly Arg Gly Phe Gly
             20                  25                  30 aag agg cgg cac ccc aaa aag ctg acc cct tta gcc tac aag cag ttt    144
Lys Arg Arg His Pro Lys Lys Leu Thr Pro Leu Ala Tyr Lys Gln Phe
         35                  40                  45 att ccc aac gta gcc gag aag acc cta ggg gcc agc ggc aga tat gaa    192
Ile Pro Asn Val Ala Glu Lys Thr Leu Gly Ala Ser Gly Arg Tyr Glu
     50                  55                  60 ggg aag atc aca aga aac tcc gaa cga ttt aag gaa ctc acc ccc aat    240
Gly Lys Ile Thr Arg Asn Ser Glu Arg Phe Lys Glu Leu Thr Pro Asn
 65                  70                  75                  80 tac aac ccc gac atc ata ttt aag gat gag gaa aac acg gga gca gac    288
Tyr Asn Pro Asp Ile Ile Phe Lys Asp Glu Glu Asn Thr Gly Ala Asp
                 85                  90                  95 cgg ctg atg act cag agg tgc aaa gac aag tta aat gcc ttg gcc atc    336
Arg Leu Met Thr Gln Arg Cys Lys Asp Lys Leu Asn Ala Leu Ala Ile
            100                 105                 110 tct gtg atg aac cag tgg cct gga gtg agg ctg cga gtg acc gag ggc    384
Ser Val Met Asn Gln Trp Pro Gly Val Arg Leu Arg Val Thr Glu Gly
        115                 120                 125 tgg gat gag gac ggc cat cat tca gag gag tct cta cac tat gag ggt    432
Trp Asp Glu Asp Gly His His Ser Glu Glu Ser Leu His Tyr Glu Gly
    130                 135                 140 cga gca gtg gac atc acc acg tcc gac cgg gac cgc agc aag tac ggc    480
Arg Ala Val Asp Ile Thr Thr Ser Asp Arg Asp Arg Ser Lys Tyr Gly
145                 150                 155                 160 atg ctg gct cgc ctg gct gtg gaa gca ggt ttc gac tgg gtc tac tat    528
Met Leu Ala Arg Leu Ala Val Glu Ala Gly Phe Asp Trp Val Tyr Tyr
                165                 170                 175 gaa tcc aaa gct cac atc cac tgt tct gtg aaa gca gag aac tcc gtg    576
Glu Ser Lys Ala His Ile His Cys Ser Val Lys Ala Glu Asn Ser Val
            180                 185                 190 gcg gcc aaa tcc ggc ggc tgt ttc ccg gga tcc gcc acc gtg cac ctg    624
Ala Ala Lys Ser Gly Gly Cys Phe Pro Gly Ser Ala Thr Val His Leu
        195                 200                 205 gag cag ggc ggc acc aag ctg gtg aag gac tta cgt ccc gga gac cgc    672
Glu Gln Gly Gly Thr Lys Leu Val Lys Asp Leu Arg Pro Gly Asp Arg
    210                 215                 220 gtg ctg gcg gct gac gac cag ggc cgg ctg ctg tac agc gac ttc ctc    720
Val Leu Ala Ala Asp Asp Gln Gly Arg Leu Leu Tyr Ser Asp Phe Leu
225                 230                 235                 240 acc ttc ctg gac cgc gac gaa ggc gcc aag aag gtc ttc tac gtg atc    768
Thr Phe Leu Asp Arg Asp Glu Gly Ala Lys Lys Val Phe Tyr Val Ile
```

```
                      245                 250                 255
gag acg ctg gag ccg cgc gag cgc ctg ctg ctc acc gcc gcg cac ctg      816
Glu Thr Leu Glu Pro Arg Glu Arg Leu Leu Leu Thr Ala Ala His Leu
            260                 265                 270 ctc ttc gtg gcg ccg cac aac gac tcg ggg ccc acg ccc ggg cca agc      864
Leu Phe Val Ala Pro His Asn Asp Ser Gly Pro Thr Pro Gly Pro Ser
        275                 280                 285 gcg ctc ttt gcc agc cgc gtg cgc ccc ggg cag cgc gtg tac gtg gtg      912
Ala Leu Phe Ala Ser Arg Val Arg Pro Gly Gln Arg Val Tyr Val Val
    290                 295                 300 gct gaa cgc ggc ggg gac cgc cgg ctg ctg ccc gcc gcg gtg cac agc      960
Ala Glu Arg Gly Gly Asp Arg Arg Leu Leu Pro Ala Ala Val His Ser
305                 310                 315                 320 gtg acg ctg cga gag gag gag gcg ggc gcg tac gcg ccg ctc acg gcg     1008
Val Thr Leu Arg Glu Glu Glu Ala Gly Ala Tyr Ala Pro Leu Thr Ala
                325                 330                 335 cac ggc acc att ctc atc aac cgg gtg ctc gcc tcg tgc tac gct gtc     1056
His Gly Thr Ile Leu Ile Asn Arg Val Leu Ala Ser Cys Tyr Ala Val
            340                 345                 350 atc gag gag cac agc tgg gca cac cgg gcc ttc gcg cct ttc cgc ctg     1104
Ile Glu Glu His Ser Trp Ala His Arg Ala Phe Ala Pro Phe Arg Leu
        355                 360                 365 gcg cac gcg ctg ctg gcc gcg ctg gca ccc gcc cgc acg gac ggc ggg     1152
Ala His Ala Leu Leu Ala Ala Leu Ala Pro Ala Arg Thr Asp Gly Gly
    370                 375                 380 ggc ggg ggc agc atc cct gca gcg caa tct gca acg gaa gcg agg ggc     1200
Gly Gly Gly Ser Ile Pro Ala Ala Gln Ser Ala Thr Glu Ala Arg Gly
385                 390                 395                 400 gcg gag ccg act gcg ggc atc cac tgg tac tcg cag ctg ctc tac cac     1248
Ala Glu Pro Thr Ala Gly Ile His Trp Tyr Ser Gln Leu Leu Tyr His
                405                 410                 415 att ggc acc tgg ctg ttg gac agc gag acc atg cat ccc ttg gga atg     1296
Ile Gly Thr Trp Leu Leu Asp Ser Glu Thr Met His Pro Leu Gly Met
            420                 425                 430 gcg gtc aag tcc agc tg                                              1313
Ala Val Lys Ser Ser
        435

<210> SEQ ID NO 5
<211> LENGTH: 1256
<212> TYPE: DNA
<213> ORGANISM: zebrafish sp.
<220> FEATURE:
<221> NAME/KEY: CDS
<222> LOCATION: (1)..(1254)

<400> SEQUENCE: 5 atg cgg ctt ttg acg aga gtg ctg ctg gtg tct ctt ctc act ctg tcc       48
Met Arg Leu Leu Thr Arg Val Leu Leu Val Ser Leu Leu Thr Leu Ser
1               5                   10                  15 ttg gtg gtg tcc gga ctg gcc tgc ggt cct ggc aga ggc tac ggc aga       96
Leu Val Val Ser Gly Leu Ala Cys Gly Pro Gly Arg Gly Tyr Gly Arg
            20                  25                  30 aga aga cat ccg aag aag ctg aca cct ctc gcc tac aag cag ttc ata      144
Arg Arg His Pro Lys Lys Leu Thr Pro Leu Ala Tyr Lys Gln Phe Ile
        35                  40                  45 cct aat gtc gcg gag aag acc tta ggg gcc agc ggc aga tac gag ggc      192
Pro Asn Val Ala Glu Lys Thr Leu Gly Ala Ser Gly Arg Tyr Glu Gly
    50                  55                  60 aag ata acg cgc aat tcg gag aga ttt aaa gaa ctt act cca aat tac      240
Lys Ile Thr Arg Asn Ser Glu Arg Phe Lys Glu Leu Thr Pro Asn Tyr
```

```
                65                  70                  75                  80
aat ccc gac att atc ttt aag gat gag gag aac acg gga gcg gac agg        288
Asn Pro Asp Ile Ile Phe Lys Asp Glu Glu Asn Thr Gly Ala Asp Arg
                85                  90                  95 ctc atg aca cag aga tgc aaa gac aag ctg aac tcg ctg gcc atc tct        336
Leu Met Thr Gln Arg Cys Lys Asp Lys Leu Asn Ser Leu Ala Ile Ser
            100                 105                 110 gta atg aac cac tgg cca ggg gtt aag ctg cgt gtg aca gag ggc tgg        384
Val Met Asn His Trp Pro Gly Val Lys Leu Arg Val Thr Glu Gly Trp
        115                 120                 125 gat gag gac ggt cac cat ttt gaa gaa tca ctc cac tac gag gga aga        432
Asp Glu Asp Gly His His Phe Glu Glu Ser Leu His Tyr Glu Gly Arg
    130                 135                 140 gct gtt gat att acc acc tct gac cga gac aag agc aaa tac ggg aca        480
Ala Val Asp Ile Thr Thr Ser Asp Arg Asp Lys Ser Lys Tyr Gly Thr
145                 150                 155                 160 ctg tct cgc cta gct gtg gag gct gga ttt gac tgg gtc tat tac gag        528
Leu Ser Arg Leu Ala Val Glu Ala Gly Phe Asp Trp Val Tyr Tyr Glu
                165                 170                 175 tcc aaa gcc cac att cat tgc tct gtc aaa gca gaa aat tcg gtt gct        576
Ser Lys Ala His Ile His Cys Ser Val Lys Ala Glu Asn Ser Val Ala
            180                 185                 190 gcg aaa tct ggg ggc tgt ttc cca ggt tcg gct ctg gtc tcg ctc cag        624
Ala Lys Ser Gly Gly Cys Phe Pro Gly Ser Ala Leu Val Ser Leu Gln
        195                 200                 205 gac gga gga cag aag gcc gtg aag gac ctg aac ccc gga gac aag gtg        672
Asp Gly Gly Gln Lys Ala Val Lys Asp Leu Asn Pro Gly Asp Lys Val
    210                 215                 220 ctg gcg gca gac agc gcg gga aac ctg gtg ttc agc gac ttc atc atg        720
Leu Ala Ala Asp Ser Ala Gly Asn Leu Val Phe Ser Asp Phe Ile Met
225                 230                 235                 240 ttc aca gac cga gac tcc acg acg cga cgt gtg ttt tac gtc ata gaa        768
Phe Thr Asp Arg Asp Ser Thr Thr Arg Arg Val Phe Tyr Val Ile Glu
                245                 250                 255 acg caa gaa ccc gtt gaa aag atc acc ctc acc gcc gct cac ctc ctt        816
Thr Gln Glu Pro Val Glu Lys Ile Thr Leu Thr Ala Ala His Leu Leu
            260                 265                 270 ttt gtc ctc gac aac tca acg gaa gat ctc cac acc atg acc gcc gcg        864
Phe Val Leu Asp Asn Ser Thr Glu Asp Leu His Thr Met Thr Ala Ala
        275                 280                 285 tat gcc agc agt gtc aga gcc gga caa aag gtg atg gtt gtt gat gat        912
Tyr Ala Ser Ser Val Arg Ala Gly Gln Lys Val Met Val Val Asp Asp
    290                 295                 300 agc ggt cag ctt aaa tct gtc atc gtg cag cgg ata tac acg gag gag        960
Ser Gly Gln Leu Lys Ser Val Ile Val Gln Arg Ile Tyr Thr Glu Glu
305                 310                 315                 320 cag cgg ggc tcg ttc gca cca gtg act gca cat ggg acc att gtg gtc       1008
Gln Arg Gly Ser Phe Ala Pro Val Thr Ala His Gly Thr Ile Val Val
                325                 330                 335 gac aga ata ctg gcg tcc tgt tac gcc gta ata gag gac cag ggg ctt       1056
Asp Arg Ile Leu Ala Ser Cys Tyr Ala Val Ile Glu Asp Gln Gly Leu
            340                 345                 350 gcg cat ttg gcc ttc gcg ccc gcc agg ctc tat tat tac gtg tca tca       1104
Ala His Leu Ala Phe Ala Pro Ala Arg Leu Tyr Tyr Tyr Val Ser Ser
        355                 360                 365 ttc ctg tcc ccc aaa act cca gca gtc ggt cca atg cga ctt tac aac       1152
Phe Leu Ser Pro Lys Thr Pro Ala Val Gly Pro Met Arg Leu Tyr Asn
    370                 375                 380 agg agg ggg tcc act ggt act cca ggc tcc tgt cat caa atg gga acg       1200
```

-continued

```
Arg Arg Gly Ser Thr Gly Thr Pro Gly Ser Cys His Gln Met Gly Thr
385                 390                 395                 400 tgg ctt ttg gac agc aac atg ctt cat cct ttg ggg atg tca gta aac      1248
Trp Leu Leu Asp Ser Asn Met Leu His Pro Leu Gly Met Ser Val Asn
                405                 410                 415 tca agc tg                                                            1256
Ser Ser
```

<210> SEQ ID NO 6
<211> LENGTH: 1425
<212> TYPE: DNA
<213> ORGANISM: Homo sapiens
<220> FEATURE:
<221> NAME/KEY: CDS
<222> LOCATION: (1)..(1425)
<223> OTHER INFORMATION: "nnn" encoding "Xaa" at position 1387-1389 may
      be a, t, c, g, other or unknown

<400> SEQUENCE: 6

```
atg ctg ctg ctg gcg aga tgt ctg ctg cta gtc ctc gtc tcc tcg ctg        48
Met Leu Leu Leu Ala Arg Cys Leu Leu Leu Val Leu Val Ser Ser Leu
  1               5                  10                  15 ctg gta tgc tcg gga ctg gcg tgc gga ccg ggc agg ggg ttc ggg aag       96
Leu Val Cys Ser Gly Leu Ala Cys Gly Pro Gly Arg Gly Phe Gly Lys
             20                  25                  30 agg agg cac ccc aaa aag ctg acc cct tta gcc tac aag cag ttt atc      144
Arg Arg His Pro Lys Lys Leu Thr Pro Leu Ala Tyr Lys Gln Phe Ile
         35                  40                  45 ccc aat gtg gcc gag aag acc cta ggc gcc agc gga agg tat gaa ggg      192
Pro Asn Val Ala Glu Lys Thr Leu Gly Ala Ser Gly Arg Tyr Glu Gly
     50                  55                  60 aag atc tcc aga aac tcc gag cga ttt aag gaa ctc acc ccc aat tac      240
Lys Ile Ser Arg Asn Ser Glu Arg Phe Lys Glu Leu Thr Pro Asn Tyr
 65                  70                  75                  80 aac ccc gac atc ata ttt aag gat gaa gaa aac acc gga gcg gac agg      288
Asn Pro Asp Ile Ile Phe Lys Asp Glu Glu Asn Thr Gly Ala Asp Arg
                 85                  90                  95 ctg atg act cag agg tgt aag gac aag ttg aac gct ttg gcc atc tcg      336
Leu Met Thr Gln Arg Cys Lys Asp Lys Leu Asn Ala Leu Ala Ile Ser
            100                 105                 110 gtg atg aac cag tgg cca gga gtg aaa ctg cgg gtg acc gag ggc tgg      384
Val Met Asn Gln Trp Pro Gly Val Lys Leu Arg Val Thr Glu Gly Trp
        115                 120                 125 gac gaa gat ggc cac cac tca gag gag tct ctg cac tac gag ggc cgc      432
Asp Glu Asp Gly His His Ser Glu Glu Ser Leu His Tyr Glu Gly Arg
    130                 135                 140 gca gtg gac atc acc acg tct gac cgc gac cgc agc aag tac ggc atg      480
Ala Val Asp Ile Thr Thr Ser Asp Arg Asp Arg Ser Lys Tyr Gly Met
145                 150                 155                 160 ctg gcc cgc ctg gcg gtg gag gcc ggc ttc gac tgg gtg tac tac gag      528
Leu Ala Arg Leu Ala Val Glu Ala Gly Phe Asp Trp Val Tyr Tyr Glu
                165                 170                 175 tcc aag gca cat atc cac tgc tcg gtg aaa gca gag aac tcg gtg gcg      576
Ser Lys Ala His Ile His Cys Ser Val Lys Ala Glu Asn Ser Val Ala
            180                 185                 190 gcc aaa tcg gga ggc tgc ttc ccg ggc tcg gcc acg gtg cac ctg gag      624
Ala Lys Ser Gly Gly Cys Phe Pro Gly Ser Ala Thr Val His Leu Glu
        195                 200                 205 cag ggc ggc acc aag ctg gtg aag gac ctg agc ccc ggg gac cgc gtg      672
Gln Gly Gly Thr Lys Leu Val Lys Asp Leu Ser Pro Gly Asp Arg Val
    210                 215                 220
```

```
ctg gcg gcg gac gac cag ggc cgg ctg ctc tac agc gac ttc ctc act      720
Leu Ala Ala Asp Asp Gln Gly Arg Leu Leu Tyr Ser Asp Phe Leu Thr
225                 230                 235                 240 ttc ctg gac cgc gac gac ggc gcc aag aag gtc ttc tac gtg atc gag      768
Phe Leu Asp Arg Asp Asp Gly Ala Lys Lys Val Phe Tyr Val Ile Glu
            245                 250                 255 acg cgg gag ccg cgc gag cgc ctg ctc acc gcc gcg cac ctg ctc          816
Thr Arg Glu Pro Arg Glu Arg Leu Leu Leu Thr Ala Ala His Leu Leu
        260                 265                 270 ttt gtg gcg ccg cac aac gac tcg gcc acc ggg gag ccc gag gcg tcc      864
Phe Val Ala Pro His Asn Asp Ser Ala Thr Gly Glu Pro Glu Ala Ser
                275                 280                 285 tcg ggc tcg ggg ccg cct tcc ggg ggc gca ctg ggg cct cgg gcg ctg      912
Ser Gly Ser Gly Pro Pro Ser Gly Gly Ala Leu Gly Pro Arg Ala Leu
290                 295                 300 ttc gcc agc cgc gtg cgc ccg ggc cag cgc gtg tac gtg gtg gcc gag      960
Phe Ala Ser Arg Val Arg Pro Gly Gln Arg Val Tyr Val Val Ala Glu
305                 310                 315                 320 cgt gac ggg gac cgc cgg ctc ctg ccc gcc gct gtg cac agc gtg acc     1008
Arg Asp Gly Asp Arg Arg Leu Leu Pro Ala Ala Val His Ser Val Thr
            325                 330                 335 cta agc gag gag gcc gcg ggc gcc tac gcg ccg ctc acg gcc cag ggc     1056
Leu Ser Glu Glu Ala Ala Gly Ala Tyr Ala Pro Leu Thr Ala Gln Gly
        340                 345                 350 acc att ctc atc aac cgg gtg ctg gcc tcg tgc tac gcg gtc atc gag     1104
Thr Ile Leu Ile Asn Arg Val Leu Ala Ser Cys Tyr Ala Val Ile Glu
    355                 360                 365 gag cac agc tgg gcg cac cgg gcc ttc gcg ccc ttc cgc ctg gcg cac     1152
Glu His Ser Trp Ala His Arg Ala Phe Ala Pro Phe Arg Leu Ala His
370                 375                 380 gcg ctc ctg gct gca ctg gcg ccc gcg cgc acg gac cgc ggc ggg gac     1200
Ala Leu Leu Ala Ala Leu Ala Pro Ala Arg Thr Asp Arg Gly Gly Asp
385                 390                 395                 400 agc ggc ggc ggg gac cgc ggg ggc ggc ggc aga gta gcc cta acc         1248
Ser Gly Gly Gly Asp Arg Gly Gly Gly Gly Arg Val Ala Leu Thr
            405                 410                 415 gct cca ggt gct gcc gac gct ccg ggt gcg ggg gcc acc gcg ggc atc     1296
Ala Pro Gly Ala Ala Asp Ala Pro Gly Ala Gly Ala Thr Ala Gly Ile
        420                 425                 430 cac tgg tac tcg cag ctg ctc tac caa ata ggc acc tgg ctc ctg gac     1344
His Trp Tyr Ser Gln Leu Leu Tyr Gln Ile Gly Thr Trp Leu Leu Asp
    435                 440                 445 agc gag gcc ctg cac ccg ctg ggc atg gcg gtc aag tcc agc nnn agc     1392
Ser Glu Ala Leu His Pro Leu Gly Met Ala Val Lys Ser Ser Xaa Ser
450                 455                 460 cgg ggg gcc ggg gga ggg gcg cgg gag ggg gcc                         1425
Arg Gly Ala Gly Gly Gly Ala Arg Glu Gly Ala
465                 470                 475

<210> SEQ ID NO 7
<211> LENGTH: 1622
<212> TYPE: DNA
<213> ORGANISM: Homo sapiens
<220> FEATURE:
<221> NAME/KEY: CDS
<222> LOCATION: (51)..(1283)

<400> SEQUENCE: 7
catcagccca ccaggagacc tcgcccgccg ctcccccggg ctccccggcc atg tct      56
                                                        Met Ser
                                                        1
```

-continued

```
ccc gcc cgg ctc cgg ccc cga ctg cac ttc tgc ctg gtc ctg ttg ctg      104
Pro Ala Arg Leu Arg Pro Arg Leu His Phe Cys Leu Val Leu Leu Leu
        5                   10                  15 ctg ctg gtg gtg ccc gcg gca tgg ggc tgc ggg ccg ggt cgg gtg gtg      152
Leu Leu Val Val Pro Ala Ala Trp Gly Cys Gly Pro Gly Arg Val Val
    20                  25                  30 ggc agc cgc cgg cga ccg cca cgc aaa ctc gtg ccg ctc gcc tac aag      200
Gly Ser Arg Arg Arg Pro Pro Arg Lys Leu Val Pro Leu Ala Tyr Lys
35                  40                  45                  50 cag ttc agc ccc aat gtg ccc gag aag acc ctg ggc gcc agc gga cgc      248
Gln Phe Ser Pro Asn Val Pro Glu Lys Thr Leu Gly Ala Ser Gly Arg
                55                  60                  65 tat gaa ggc aag atc gct cgc agc tcc gag cgc ttc aag gag ctc acc      296
Tyr Glu Gly Lys Ile Ala Arg Ser Ser Glu Arg Phe Lys Glu Leu Thr
            70                  75                  80 ccc aat tac aat cca gac atc atc ttc aag gac gag gag aac aca ggc      344
Pro Asn Tyr Asn Pro Asp Ile Ile Phe Lys Asp Glu Glu Asn Thr Gly
                85                  90                  95 gcc gac cgc ctc atg acc cag cgc tgc aag gac cgc ctg aac tcg ctg      392
Ala Asp Arg Leu Met Thr Gln Arg Cys Lys Asp Arg Leu Asn Ser Leu
100                 105                 110 gct atc tcg gtg atg aac cag tgg ccc ggt gtg aag ctg cgg gtg acc      440
Ala Ile Ser Val Met Asn Gln Trp Pro Gly Val Lys Leu Arg Val Thr
115                 120                 125                 130 gag ggc tgg gac gag gac ggc cac cac tca gag gag tcc ctg cat tat      488
Glu Gly Trp Asp Glu Asp Gly His His Ser Glu Glu Ser Leu His Tyr
                135                 140                 145 gag ggc cgc gcg gtg gac atc acc aca tca gac cgc gac cgc aat aag      536
Glu Gly Arg Ala Val Asp Ile Thr Thr Ser Asp Arg Asp Arg Asn Lys
            150                 155                 160 tat gga ctg ctg gcg cgc ttg gca gtg gag gcc ggc ttt gac tgg gtg      584
Tyr Gly Leu Leu Ala Arg Leu Ala Val Glu Ala Gly Phe Asp Trp Val
        165                 170                 175 tat tac gag tca aag gcc cac gtg cat tgc tcc gtc aag tcc gag cac      632
Tyr Tyr Glu Ser Lys Ala His Val His Cys Ser Val Lys Ser Glu His
180                 185                 190 tcg gcc gca gcc aag acg ggc ggc tgc ttc cct gcc gga gcc cag gta      680
Ser Ala Ala Ala Lys Thr Gly Gly Cys Phe Pro Ala Gly Ala Gln Val
195                 200                 205                 210 cgc ctg gag agt ggg gcg cgt gtg gcc ttg tca gcc gtg agg ccg gga      728
Arg Leu Glu Ser Gly Ala Arg Val Ala Leu Ser Ala Val Arg Pro Gly
                215                 220                 225 gac cgt gtg ctg gcc atg ggg gag gat ggg agc ccc acc ttc agc gat      776
Asp Arg Val Leu Ala Met Gly Glu Asp Gly Ser Pro Thr Phe Ser Asp
            230                 235                 240 gtg ctc att ttc ctg gac cgc gag ccc cac agg ctg aga gcc ttc cag      824
Val Leu Ile Phe Leu Asp Arg Glu Pro His Arg Leu Arg Ala Phe Gln
        245                 250                 255 gtc atc gag act cag gac ccc cca cgc cgc ctg gca ctc aca ccc gct      872
Val Ile Glu Thr Gln Asp Pro Pro Arg Arg Leu Ala Leu Thr Pro Ala
260                 265                 270 cac ctg ctc ttt acg gct gac aat cac acg gag ccg gca gcc cgc ttc      920
His Leu Leu Phe Thr Ala Asp Asn His Thr Glu Pro Ala Ala Arg Phe
275                 280                 285                 290 cgg gcc aca ttt gcc agc cac gtg cag cct ggc cag tac gtg ctg gtg      968
Arg Ala Thr Phe Ala Ser His Val Gln Pro Gly Gln Tyr Val Leu Val
                295                 300                 305 gct ggg gtg cca ggc ctg cag cct gcc cgc gtg gca gct gtc tct aca     1016
Ala Gly Val Pro Gly Leu Gln Pro Ala Arg Val Ala Ala Val Ser Thr
            310                 315                 320
```

-continued

```
cac gtg gcc ctc ggg gcc tac gcc ccg ctc aca aag cat ggg aca ctg        1064
His Val Ala Leu Gly Ala Tyr Ala Pro Leu Thr Lys His Gly Thr Leu
        325                 330                 335 gtg gtg gag gat gtg gtg gca tcc tgc ttc gcg gcc gtg gct gac cac        1112
Val Val Glu Asp Val Val Ala Ser Cys Phe Ala Ala Val Ala Asp His
340                 345                 350 cac ctg gct cag ttg gcc ttc tgg ccc ctg aga ctc ttt cac agc ttg        1160
His Leu Ala Gln Leu Ala Phe Trp Pro Leu Arg Leu Phe His Ser Leu
355                 360                 365                 370 gca tgg ggc agc tgg acc ccg ggg gag ggt gtg cat tgg tac ccc cag        1208
Ala Trp Gly Ser Trp Thr Pro Gly Glu Gly Val His Trp Tyr Pro Gln
            375                 380                 385 ctc ctc tac cgc ctg ggg cgt ctc ctg cta gaa gag ggc agc ttc cac        1256
Leu Leu Tyr Arg Leu Gly Arg Leu Leu Leu Glu Glu Gly Ser Phe His
        390                 395                 400 cca ctg ggc atg tcc ggg gca ggg agc tgaaaggact ccaccgctgc              1303
Pro Leu Gly Met Ser Gly Ala Gly Ser
        405                 410 cctcctggaa ctgctgtact gggtccagaa gcctctcagc caggagggag ctggccctgg      1363
aagggacctg agctggggga cactggctcc tgccatctcc tctgccatga agatacacca      1423
ttgagacttg actgggcaac accagcgtcc cccacccgcg tcgtggtgta gtcatagagc      1483
tgcaagctga gctggcgagg ggatggttgt tgacccctct ctcctagaga ccttgaggct      1543
ggcacggcga ctcccaactc agcctgctct cactacgagt tttcatactc tgcctccccc      1603
attgggaggg cccattccc                                                    1622

<210> SEQ ID NO 8
<211> LENGTH: 1190
<212> TYPE: DNA
<213> ORGANISM: Homo sapiens
<220> FEATURE:
<221> NAME/KEY: CDS
<222> LOCATION: (1)..(1188)

<400> SEQUENCE: 8 atg gct ctc ctg acc aat cta ctg ccc ttg tgc tgc ttg gca ctt ctg        48
Met Ala Leu Leu Thr Asn Leu Leu Pro Leu Cys Cys Leu Ala Leu Leu
1               5                   10                  15 gcg ctg cca gcc cag agc tgc ggg ccg ggc cgg ggg ccg gtt ggc cgg        96
Ala Leu Pro Ala Gln Ser Cys Gly Pro Gly Arg Gly Pro Val Gly Arg
                20                  25                  30 cgc cgc tat gcg cgc aag cag ctc gtg ccg cta ctc tac aag caa ttt        144
Arg Arg Tyr Ala Arg Lys Gln Leu Val Pro Leu Leu Tyr Lys Gln Phe
            35                  40                  45 gtg ccc ggc gtg cca gag cgg acc ctg ggc gcc agt ggg cca gcg gag        192
Val Pro Gly Val Pro Glu Arg Thr Leu Gly Ala Ser Gly Pro Ala Glu
        50                  55                  60 ggg agg gtg gca agg ggc tcc gag cgc ttc cgg gac ctc gtg ccc aac        240
Gly Arg Val Ala Arg Gly Ser Glu Arg Phe Arg Asp Leu Val Pro Asn
65                  70                  75                  80 tac aac ccc gac atc atc ttc aag gat gag gag aac agt gga gcc gac        288
Tyr Asn Pro Asp Ile Ile Phe Lys Asp Glu Glu Asn Ser Gly Ala Asp
                85                  90                  95 cgc ctg atg acc gag cgt tgc aag gag agg gtg aac gct ttg gcc att        336
Arg Leu Met Thr Glu Arg Cys Lys Glu Arg Val Asn Ala Leu Ala Ile
                100                 105                 110 gcc gtg atg aac atg tgg ccc gga gtg cgc cta cga gtg act gag ggc        384
Ala Val Met Asn Met Trp Pro Gly Val Arg Leu Arg Val Thr Glu Gly
            115                 120                 125
```

```
tgg gac gag gac ggc cac cac gct cag gat tca ctc cac tac gaa ggc    432
Trp Asp Glu Asp Gly His His Ala Gln Asp Ser Leu His Tyr Glu Gly
130                 135                 140 cgt gct ttg gac atc act acg tct gac cgc gac cgc aac aag tat ggg    480
Arg Ala Leu Asp Ile Thr Thr Ser Asp Arg Asp Arg Asn Lys Tyr Gly
145                 150                 155                 160 ttg ctg gcg cgc ctc gca gtg gaa gcc ggc ttc gac tgg gtc tac tac    528
Leu Leu Ala Arg Leu Ala Val Glu Ala Gly Phe Asp Trp Val Tyr Tyr
                165                 170                 175 gag tcc cgc aac cac gtc cac gtg tcg gtc aaa gct gat aac tca ctg    576
Glu Ser Arg Asn His Val His Val Ser Val Lys Ala Asp Asn Ser Leu
            180                 185                 190 gcg gtc cgg gcg ggc ggc tgc ttt ccg gga aat gca act gtg cgc ctg    624
Ala Val Arg Ala Gly Gly Cys Phe Pro Gly Asn Ala Thr Val Arg Leu
        195                 200                 205 tgg agc ggc gag cgg aaa ggg ctg cgg gaa ctg cac cgc gga gac tgg    672
Trp Ser Gly Glu Arg Lys Gly Leu Arg Glu Leu His Arg Gly Asp Trp
    210                 215                 220 gtt ttg gcg gcc gat gcg tca ggc cgg gtg gtg ccc acg ccg gtg ctg    720
Val Leu Ala Ala Asp Ala Ser Gly Arg Val Val Pro Thr Pro Val Leu
225                 230                 235                 240 ctc ttc ctg gac cgg gac ttg cag cgc cgg gct tca ttt gtg gct gtg    768
Leu Phe Leu Asp Arg Asp Leu Gln Arg Arg Ala Ser Phe Val Ala Val
                245                 250                 255 gag acc gag tgg cct cca cgc aaa ctg ttg ctc acg ccc tgg cac ctg    816
Glu Thr Glu Trp Pro Pro Arg Lys Leu Leu Leu Thr Pro Trp His Leu
            260                 265                 270 gtg ttt gcc gct cga ggg ccg gcg ccc gcg cca ggc gac ttt gca ccg    864
Val Phe Ala Ala Arg Gly Pro Ala Pro Ala Pro Gly Asp Phe Ala Pro
        275                 280                 285 gtg ttc gcg cgc cgg cta cgc gct ggg gac tcg gtg ctg gcg ccc ggc    912
Val Phe Ala Arg Arg Leu Arg Ala Gly Asp Ser Val Leu Ala Pro Gly
    290                 295                 300 ggg gat gcg ctt cgg cca gcg cgc gtg gcc cgt gtg gcg cgg gag gaa    960
Gly Asp Ala Leu Arg Pro Ala Arg Val Ala Arg Val Ala Arg Glu Glu
305                 310                 315                 320 gcc gtg ggc gtg ttc gcg ccg ctc acc gcg cac ggg acg ctg ctg gtg   1008
Ala Val Gly Val Phe Ala Pro Leu Thr Ala His Gly Thr Leu Leu Val
                325                 330                 335 aac gat gtc ctg gcc tct tgc tac gcg gtt ctg gag agt cac cag tgg   1056
Asn Asp Val Leu Ala Ser Cys Tyr Ala Val Leu Glu Ser His Gln Trp
            340                 345                 350 gcg cac cgc gct ttt gcc ccc ttg aga ctg ctg cac gcg cta ggg gcg   1104
Ala His Arg Ala Phe Ala Pro Leu Arg Leu Leu His Ala Leu Gly Ala
        355                 360                 365 ctg ctc ccc ggc ggg gcc gtc cag ccg act ggc atg cat tgg tac tct   1152
Leu Leu Pro Gly Gly Ala Val Gln Pro Thr Gly Met His Trp Tyr Ser
    370                 375                 380 cgg ctc ctc tac cgc tta gcg gag gag cta ctg ggc tg                 1190
Arg Leu Leu Tyr Arg Leu Ala Glu Glu Leu Leu Gly
385                 390                 395
```

<210> SEQ ID NO 9
<211> LENGTH: 1251
<212> TYPE: DNA
<213> ORGANISM: Zebrafish sp.
<220> FEATURE:
<221> NAME/KEY: CDS
<222> LOCATION: (1)..(1248)

<400> SEQUENCE: 9

```
atg gac gta agg ctg cat ctg aag caa ttt gct tta ctg tgt ttt atc      48
Met Asp Val Arg Leu His Leu Lys Gln Phe Ala Leu Leu Cys Phe Ile
 1               5                  10                  15 agc ttg ctt ctg acg cct tgt gga tta gcc tgt ggt cct ggt aga ggt      96
Ser Leu Leu Leu Thr Pro Cys Gly Leu Ala Cys Gly Pro Gly Arg Gly
             20                  25                  30 tat gga aaa cga aga cac cca aag aaa tta acc ccg ttg gct tac aag     144
Tyr Gly Lys Arg Arg His Pro Lys Lys Leu Thr Pro Leu Ala Tyr Lys
         35                  40                  45 caa ttc atc ccc aac gtt gct gag aaa acg ctt gga gcc agc ggc aaa     192
Gln Phe Ile Pro Asn Val Ala Glu Lys Thr Leu Gly Ala Ser Gly Lys
     50                  55                  60 tac gaa ggc aaa atc aca agg aat tca gag aga ttt aaa gag ctg att     240
Tyr Glu Gly Lys Ile Thr Arg Asn Ser Glu Arg Phe Lys Glu Leu Ile
 65                  70                  75                  80 ccg aat tat aat ccc gat atc atc ttt aag gac gag gaa aac aca aac     288
Pro Asn Tyr Asn Pro Asp Ile Ile Phe Lys Asp Glu Glu Asn Thr Asn
                 85                  90                  95 gct gac agg ctg atg acc aag cgc tgt aag gac aag tta aat tcg ttg     336
Ala Asp Arg Leu Met Thr Lys Arg Cys Lys Asp Lys Leu Asn Ser Leu
            100                 105                 110 gcc ata tcc gtc atg aac cac tgg ccc ggc gtg aaa ctg cgc gtc act     384
Ala Ile Ser Val Met Asn His Trp Pro Gly Val Lys Leu Arg Val Thr
        115                 120                 125 gaa ggc tgg gat gag gat ggt cac cat tta gaa gaa tct ttg cac tat     432
Glu Gly Trp Asp Glu Asp Gly His His Leu Glu Glu Ser Leu His Tyr
    130                 135                 140 gag gga cgg gca gtg gac atc act acc tca gac agg gat aaa agc aag     480
Glu Gly Arg Ala Val Asp Ile Thr Thr Ser Asp Arg Asp Lys Ser Lys
145                 150                 155                 160 tat ggg atg cta tcc agg ctt gca gtg gag gca gga ttc gac tgg gtc     528
Tyr Gly Met Leu Ser Arg Leu Ala Val Glu Ala Gly Phe Asp Trp Val
                165                 170                 175 tat tat gaa tct aaa gcc cac ata cac tgc tct gtc aaa gca gaa aat     576
Tyr Tyr Glu Ser Lys Ala His Ile His Cys Ser Val Lys Ala Glu Asn
            180                 185                 190 tca gtg gct gct aaa tca gga gga tgt ttt cct ggg tct ggg acg gtg     624
Ser Val Ala Ala Lys Ser Gly Gly Cys Phe Pro Gly Ser Gly Thr Val
        195                 200                 205 aca ctt ggt gat ggg acg agg aaa ccc atc aaa gat ctt aaa gtg ggc     672
Thr Leu Gly Asp Gly Thr Arg Lys Pro Ile Lys Asp Leu Lys Val Gly
    210                 215                 220 gac cgg gtt ttg gct gca gac gag aag gga aat gtc tta ata agc gac     720
Asp Arg Val Leu Ala Ala Asp Glu Lys Gly Asn Val Leu Ile Ser Asp
225                 230                 235                 240 ttt att atg ttt ata gac cac gat ccg aca acg aga agg caa ttc atc     768
Phe Ile Met Phe Ile Asp His Asp Pro Thr Thr Arg Arg Gln Phe Ile
                245                 250                 255 gtc atc gag acg tca gaa cct ttc acc aag ctc acc ctc act gcc gcg     816
Val Ile Glu Thr Ser Glu Pro Phe Thr Lys Leu Thr Leu Thr Ala Ala
            260                 265                 270 cac cta gtt ttc gtt gga aac tct tca gca gct tcg ggt ata aca gca     864
His Leu Val Phe Val Gly Asn Ser Ser Ala Ala Ser Gly Ile Thr Ala
        275                 280                 285 aca ttt gcc agc aac gtg aag cct gga gat aca gtt tta gtg tgg gaa     912
Thr Phe Ala Ser Asn Val Lys Pro Gly Asp Thr Val Leu Val Trp Glu
    290                 295                 300 gac aca tgc gag agc ctc aag agc gtt aca gtg aaa agg att tac act     960
Asp Thr Cys Glu Ser Leu Lys Ser Val Thr Val Lys Arg Ile Tyr Thr
```

-continued

```
                305                 310                 315                 320
gag gag cac gag ggc tct ttt gcg cca gtc acc gcg cac gga acc ata        1008
Glu Glu His Glu Gly Ser Phe Ala Pro Val Thr Ala His Gly Thr Ile
                    325                 330                 335 ata gtg gat cag gtg ttg gca tcg tgc tac gcg gtc att gag aac cac        1056
Ile Val Asp Gln Val Leu Ala Ser Cys Tyr Ala Val Ile Glu Asn His
            340                 345                 350 aaa tgg gca cat tgg gct ttt gcg ccg gtc agg ttg tgt cac aag ctg        1104
Lys Trp Ala His Trp Ala Phe Ala Pro Val Arg Leu Cys His Lys Leu
        355                 360                 365 atg acg tgg ctt ttt ccg gct cgt gaa tca aac gtc aat ttt cag gag        1152
Met Thr Trp Leu Phe Pro Ala Arg Glu Ser Asn Val Asn Phe Gln Glu
    370                 375                 380 gat ggt atc cac tgg tac tca aat atg ctg ttt cac atc ggc tct tgg        1200
Asp Gly Ile His Trp Tyr Ser Asn Met Leu Phe His Ile Gly Ser Trp
385                 390                 395                 400 ctg ctg gac aga gac tct ttc cat cca ctc ggg att tta cac tta agt        1248
Leu Leu Asp Arg Asp Ser Phe His Pro Leu Gly Ile Leu His Leu Ser
                405                 410                 415 tga                                                                    1251
```

<210> SEQ ID NO 10
<211> LENGTH: 425
<212> TYPE: PRT
<213> ORGANISM: Gallus sp.

<400> SEQUENCE: 10

```
Met Val Glu Met Leu Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
                20                  25                  30

Ile Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
        50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
```

```
225                 230                 235                 240
Phe Leu Thr Phe Leu Asp Arg Met Asp Ser Ser Arg Lys Leu Phe Tyr
                245                 250                 255
Val Ile Glu Thr Arg Gln Pro Arg Ala Arg Leu Leu Leu Thr Ala Ala
                260                 265                 270
His Leu Leu Phe Val Ala Pro Gln His Asn Gln Ser Glu Ala Thr Gly
                275                 280                 285
Ser Thr Ser Gly Gln Ala Leu Phe Ala Ser Asn Val Lys Pro Gly Gln
                290                 295                 300
Arg Val Tyr Val Leu Gly Glu Gly Gly Gln Leu Leu Pro Ala Ser
305                 310                 315                 320
Val His Ser Val Ser Leu Arg Glu Glu Ala Ser Gly Ala Tyr Ala Pro
                325                 330                 335
Leu Thr Ala Gln Gly Thr Ile Leu Ile Asn Arg Val Leu Ala Ser Cys
                340                 345                 350
Tyr Ala Val Ile Glu Glu His Ser Trp Ala His Trp Ala Phe Ala Pro
                355                 360                 365
Phe Arg Leu Ala Gln Gly Leu Leu Ala Ala Leu Cys Pro Asp Gly Ala
                370                 375                 380
Ile Pro Thr Ala Ala Thr Thr Thr Gly Ile His Trp Tyr Ser Arg
385                 390                 395                 400
Leu Leu Tyr Arg Ile Gly Ser Trp Val Leu Asp Gly Asp Ala Leu His
                405                 410                 415
Pro Leu Gly Met Val Ala Pro Ala Ser
                420                 425

<210> SEQ ID NO 11
<211> LENGTH: 396
<212> TYPE: PRT
<213> ORGANISM: Murine sp.

<400> SEQUENCE: 11

Met Ala Leu Pro Ala Ser Leu Leu Pro Leu Cys Cys Leu Ala Leu Leu
  1               5                  10                  15
Ala Leu Ser Ala Gln Ser Cys Gly Pro Gly Arg Gly Pro Val Gly Arg
                20                  25                  30
Arg Arg Tyr Val Arg Lys Gln Leu Val Pro Leu Leu Tyr Lys Gln Phe
                35                  40                  45
Val Pro Ser Met Pro Glu Arg Thr Leu Gly Ala Ser Gly Pro Ala Glu
                50                  55                  60
Gly Arg Val Thr Arg Gly Ser Glu Arg Phe Arg Asp Leu Val Pro Asn
 65                 70                  75                  80
Tyr Asn Pro Asp Ile Ile Phe Lys Asp Glu Glu Asn Ser Gly Ala Asp
                85                  90                  95
Arg Leu Met Thr Glu Arg Cys Lys Glu Arg Val Asn Ala Leu Ala Ile
                100                 105                 110
Ala Val Met Asn Met Trp Pro Gly Val Arg Leu Arg Val Thr Glu Gly
                115                 120                 125
Trp Asp Glu Asp Gly His His Ala Gln Asp Ser Leu His Tyr Glu Gly
                130                 135                 140
Arg Ala Leu Asp Ile Thr Thr Ser Asp Arg Asp Arg Asn Lys Tyr Gly
145                 150                 155                 160
Leu Leu Ala Arg Leu Ala Val Glu Ala Gly Phe Asp Trp Val Tyr Tyr
                165                 170                 175
```

-continued

```
Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Murine sp.

<400> SEQUENCE: 12

Met Ser Pro Ala Trp Leu Arg Pro Arg Leu Arg Phe Cys Leu Phe Leu
  1               5                  10                  15

Leu Leu Leu Leu Leu Val Pro Ala Ala Arg Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160
```

```
Asn Lys Tyr Gly Leu Leu Ala Arg Leu Ala Val Glu Ala Gly Phe Asp
                165                 170                 175
Trp Val Tyr Tyr Glu Ser Lys Ala His Val His Cys Ser Val Lys Ser
            180                 185                 190
Glu His Ser Ala Ala Ala Lys Thr Gly Gly Cys Phe Pro Ala Gly Ala
        195                 200                 205
Gln Val Arg Leu Glu Asn Gly Glu Arg Val Ala Leu Ser Ala Val Lys
    210                 215                 220
Pro Gly Asp Arg Val Leu Ala Met Gly Glu Asp Gly Thr Pro Thr Phe
225                 230                 235                 240
Ser Asp Val Leu Ile Phe Leu Asp Arg Glu Pro Asn Arg Leu Arg Ala
                245                 250                 255
Phe Gln Val Ile Glu Thr Gln Asp Pro Pro Arg Arg Leu Ala Leu Thr
            260                 265                 270
Pro Ala His Leu Leu Phe Ile Ala Asp Asn His Thr Glu Pro Ala Ala
        275                 280                 285
His Phe Arg Ala Thr Phe Ala Ser His Val Gln Pro Gly Gln Tyr Val
    290                 295                 300
Leu Val Ser Gly Val Pro Gly Leu Gln Pro Ala Arg Val Ala Ala Val
305                 310                 315                 320
Ser Thr His Val Ala Leu Gly Ser Tyr Ala Pro Leu Thr Arg His Gly
                325                 330                 335
Thr Leu Val Val Glu Asp Val Val Ala Ser Cys Phe Ala Ala Val Ala
            340                 345                 350
Asp His His Leu Ala Gln Leu Ala Phe Trp Pro Leu Arg Leu Phe Pro
        355                 360                 365
Ser Leu Ala Trp Gly Ser Trp Thr Pro Ser Glu Gly Val His Ser Tyr
370                 375                 380
Pro Gln Met Leu Tyr Arg Leu Gly Arg Leu Leu Glu Glu Ser Thr
385                 390                 395                 400
Phe His Pro Leu Gly Met Ser Gly Ala Gly Ser
                405                 410

<210> SEQ ID NO 13
<211> LENGTH: 437
<212> TYPE: PRT
<213> ORGANISM: Murine sp.

<400> SEQUENCE: 13

Met Leu Leu Leu Ala Arg Cys Phe Leu Val Ile Leu Ala Ser Ser
 1               5                  10                  15
Leu Leu Val Cys Pro Gly Leu Ala Cys Gly Pro Gly Arg Gly Phe Gly
            20                  25                  30
Lys Arg Arg His Pro Lys Lys Leu Thr Pro Leu Ala Tyr Lys Gln Phe
        35                  40                  45
Ile Pro Asn Val Ala Glu Lys Thr Leu Gly Ala Ser Gly Arg Tyr Glu
    50                  55                  60
Gly Lys Ile Thr Arg Asn Ser Glu Arg Phe Lys Glu Leu Thr Pro Asn
65                  70                  75                  80
Tyr Asn Pro Asp Ile Ile Phe Lys Asp Glu Glu Asn Thr Gly Ala Asp
                85                  90                  95
Arg Leu Met Thr Gln Arg Cys Lys Asp Lys Leu Asn Ala Leu Ala Ile
            100                 105                 110
Ser Val Met Asn Gln Trp Pro Gly Val Arg Leu Arg Val Thr Glu Gly
```

-continued

```
                115                 120                 125

Trp Asp Glu Asp Gly His His Ser Glu Glu Ser Leu His Tyr Glu Gly
            130                 135                 140

Arg Ala Val Asp Ile Thr Thr Ser Asp Arg Asp Arg Ser Lys Tyr Gly
        145                 150                 155                 160

Met Leu Ala Arg Leu Ala Val Glu Ala Gly Phe Asp Trp Val Tyr Tyr
                        165                 170                 175

Glu Ser Lys Ala His Ile His Cys Ser Val Lys Ala Glu Asn Ser Val
                    180                 185                 190

Ala Ala Lys Ser Gly Gly Cys Phe Pro Gly Ser Ala Thr Val His Leu
                195                 200                 205

Glu Gln Gly Gly Thr Lys Leu Val Lys Asp Leu Arg Pro Gly Asp Arg
            210                 215                 220

Val Leu Ala Ala Asp Asp Gln Gly Arg Leu Leu Tyr Ser Asp Phe Leu
        225                 230                 235                 240

Thr Phe Leu Asp Arg Asp Glu Gly Ala Lys Lys Val Phe Tyr Val Ile
                        245                 250                 255

Glu Thr Leu Glu Pro Arg Glu Arg Leu Leu Leu Thr Ala Ala His Leu
                    260                 265                 270

Leu Phe Val Ala Pro His Asn Asp Ser Gly Pro Thr Pro Gly Pro Ser
                275                 280                 285

Ala Leu Phe Ala Ser Arg Val Arg Pro Gly Gln Arg Val Tyr Val Val
            290                 295                 300

Ala Glu Arg Gly Gly Asp Arg Arg Leu Leu Pro Ala Ala Val His Ser
        305                 310                 315                 320

Val Thr Leu Arg Glu Glu Glu Ala Gly Ala Tyr Ala Pro Leu Thr Ala
                        325                 330                 335

His Gly Thr Ile Leu Ile Asn Arg Val Leu Ala Ser Cys Tyr Ala Val
                    340                 345                 350

Ile Glu Glu His Ser Trp Ala His Arg Ala Phe Ala Pro Phe Arg Leu
                355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
        385                 390                 395                 400

Ala Glu Pro Thr Ala Gly Ile His Trp Tyr Ser Gln Leu Leu Tyr His
                        405                 410                 415

Ile Gly Thr Trp Leu Leu Asp Ser Glu Thr Met His Pro Leu Gly Met
                    420                 425                 430

Ala Val Lys Ser Ser
                    435

<210> SEQ ID NO 14
<211> LENGTH: 418
<212> TYPE: PRT
<213> ORGANISM: zebrafish sp.

<400> SEQUENCE: 14

Met Arg Leu Leu Thr Arg Val Leu Leu Val Ser Leu Leu Thr Leu Ser
 1               5                  10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45
```

```
Pro Asn Val Ala Glu Lys Thr Leu Gly Ala Ser Gly Arg Tyr Glu Gly
     50                  55                  60

Lys Ile Thr Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
            115                 120                 125

Asp Glu Asp Gly His His Phe Glu Glu Ser Leu His Tyr Glu Gly Arg
        130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
                180                 185                 190

Ala Lys Ser Gly Gly Cys Phe Pro Gly Ser Ala Leu Val Ser Leu Gln
            195                 200                 205

Asp Gly Gly Gln Lys Ala Val Lys Asp Leu Asn Pro Gly Asp Lys Val
        210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
                260                 265                 270

Phe Val Leu Asp Asn Ser Thr Glu Asp Leu His Thr Met Thr Ala Ala
            275                 280                 285

Tyr Ala Ser Ser Val Arg Ala Gly Gln Lys Val Met Val Val Asp Asp
        290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
                340                 345                 350

Ala His Leu Ala Phe Ala Pro Ala Arg Leu Tyr Tyr Val Ser Ser
            355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser

<210> SEQ ID NO 15
<211> LENGTH: 475
<212> TYPE: PRT
<213> ORGANISM: Homo sapiens
<220> FEATURE:
<223> OTHER INFORMATION: Xaa at position 463 is any or unknown amino
      acid
```

<400> SEQUENCE: 15

```
Met Leu Leu Leu Ala Arg Cys Leu Leu Leu Val Leu Ser Ser Leu
 1               5                  10                  15
Leu Val Cys Ser Gly Leu Ala Cys Gly Pro Gly Arg Gly Phe Gly Lys
             20                  25                  30
Arg Arg His Pro Lys Lys Leu Thr Pro Leu Ala Tyr Lys Gln Phe Ile
         35                  40                  45
Pro Asn Val Ala Glu Lys Thr Leu Gly Ala Ser Gly Arg Tyr Glu Gly
     50                  55                  60
Lys Ile Ser Arg Asn Ser Glu Arg Phe Lys Glu Leu Thr Pro Asn Tyr
 65                  70                  75                  80
Asn Pro Asp Ile Ile Phe Lys Asp Glu Glu Asn Thr Gly Ala Asp Arg
                 85                  90                  95
Leu Met Thr Gln Arg Cys Lys Asp Lys Leu Asn Ala Leu Ala Ile Ser
            100                 105                 110
Val Met Asn Gln Trp Pro Gly Val Lys Leu Arg Val Thr Glu Gly Trp
            115                 120                 125
Asp Glu Asp Gly His His Ser Glu Glu Ser Leu His Tyr Glu Gly Arg
            130                 135                 140
Ala Val Asp Ile Thr Thr Ser Asp Arg Asp Arg Ser Lys Tyr Gly Met
145                 150                 155                 160
Leu Ala Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
            180                 185                 190
Ala Lys Ser Gly Gly Cys Phe Pro Gly Ser Ala Thr Val His Leu Glu
            195                 200                 205
Gln Gly Gly Thr Lys Leu Val Lys Asp Leu Ser Pro Gly Asp Arg Val
            210                 215                 220
Leu Ala Ala Asp Asp Gln Gly Arg Leu Leu Tyr Ser Asp Phe Leu Thr
225                 230                 235                 240
Phe Leu Asp Arg Asp Asp Gly Ala Lys Lys Val Phe Tyr Val Ile Glu
                245                 250                 255
Thr Arg Glu Pro Arg Glu Arg Leu Leu Leu Thr Ala Ala His Leu Leu
            260                 265                 270
Phe Val Ala Pro His Asn Asp Ser Ala Thr Gly Glu Pro Glu Ala Ser
            275                 280                 285
Ser Gly Ser Gly Pro Pro Ser Gly Gly Ala Leu Gly Pro Arg Ala Leu
            290                 295                 300
Phe Ala Ser Arg Val Arg Pro Gly Gln Arg Val Tyr Val Val Ala Glu
305                 310                 315                 320
Arg Asp Gly Asp Arg Arg Leu Leu Pro Ala Ala Val His Ser Val Thr
                325                 330                 335
Leu Ser Glu Glu Ala Ala Gly Ala Tyr Ala Pro Leu Thr Ala Gln Gly
            340                 345                 350
Thr Ile Leu Ile Asn Arg Val Leu Ala Ser Cys Tyr Ala Val Ile Glu
            355                 360                 365
Glu His Ser Trp Ala His Arg Ala Phe Ala Pro Phe Arg Leu Ala His
            370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Gly Arg Val Ala Leu Thr
```

```
                      405                 410                 415
Ala Pro Gly Ala Ala Asp Ala Pro Gly Ala Gly Ala Thr Ala Gly Ile
                420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser Xaa Ser
        450                 455                 460

Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
 1               5                  10                  15

Leu Leu Leu Leu Val Val Pro Ala Ala Trp Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
290                 295                 300
```

-continued

```
Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
                340                 345                 350

Asp His His Leu Ala Gln Leu Ala Phe Trp Pro Leu Arg Leu Phe His
                355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
                20                  25                  30

Arg Arg Tyr Ala Arg Lys Gln Leu Val Pro Leu Leu Tyr Lys Gln Phe
            35                  40                  45

Val Pro Gly Val Pro Glu Arg Thr Leu Gly Ala Ser Gly Pro Ala Glu
50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
                100                 105                 110

Ala Val Met Asn Met Trp Pro Gly Val Arg Leu Arg Val Thr Glu Gly
            115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
                180                 185                 190

Ala Val Arg Ala Gly Gly Cys Phe Pro Gly Asn Ala Thr Val Arg Leu
            195                 200                 205

Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
                260                 265                 270
```

```
Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
            355                 360                 365

Leu Leu Pro Gly Gly Ala Val Gln Pro Thr Gly Met His Trp Tyr Ser
        370                 375                 380

Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Zebrafish sp.

<400> SEQUENCE: 18

Met Asp Val Arg Leu His Leu Lys Gln Phe Ala Leu Leu Cys Phe Ile
  1               5                  10                  15

Ser Leu Leu Leu Thr Pro Cys Gly Leu Ala Cys Gly Pro Gly Arg Gly
                 20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
        50                  55                  60

Tyr Glu Gly Lys Ile Thr Arg Asn Ser Glu Arg Phe Lys Glu Leu Ile
 65                  70                  75                  80

Pro Asn Tyr Asn Pro Asp Ile Ile Phe Lys Asp Glu Asn Thr Asn
                 85                  90                  95

Ala Asp Arg Leu Met Thr Lys Arg Cys Lys Asp Lys Leu Asn Ser Leu
                100                 105                 110

Ala Ile Ser Val Met Asn His Trp Pro Gly Val Lys Leu Arg Val Thr
            115                 120                 125

Glu Gly Trp Asp Glu Asp Gly His His Leu Glu Glu Ser Leu His Tyr
        130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
                180                 185                 190

Ser Val Ala Ala Lys Ser Gly Gly Cys Phe Pro Gly Ser Gly Thr Val
            195                 200                 205

Thr Leu Gly Asp Gly Thr Arg Lys Pro Ile Lys Asp Leu Lys Val Gly
        210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
```

```
                    245                 250                 255
Val Ile Glu Thr Ser Glu Pro Phe Thr Lys Leu Thr Leu Thr Ala Ala
                260                 265                 270

His Leu Val Phe Val Gly Asn Ser Ser Ala Ala Ser Gly Ile Thr Ala
            275                 280                 285

Thr Phe Ala Ser Asn Val Lys Pro Gly Asp Thr Val Leu Val Trp Glu
        290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
                340                 345                 350

Lys Trp Ala His Trp Ala Phe Ala Pro Val Arg Leu Cys His Lys Leu
            355                 360                 365

Met Thr Trp Leu Phe Pro Ala Arg Glu Ser Asn Val Asn Phe Gln Glu
        370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415

<210> SEQ ID NO 19
<211> LENGTH: 1416
<212> TYPE: DNA
<213> ORGANISM: Drosophila sp.
<220> FEATURE:
<221> NAME/KEY: CDS
<222> LOCATION: (1)..(1413)

<400> SEQUENCE: 19 atg gat aac cac agc tca gtg cct tgg gcc agt gcc gcc agt gtc acc      48
Met Asp Asn His Ser Ser Val Pro Trp Ala Ser Ala Ala Ser Val Thr
 1               5                  10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
                20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
            35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
        50                  55                  60 acc tct ctg gtg gcc ctg ctg ctg atc gtc ttg ccg atg gtc ttt agc     240
Thr Ser Leu Val Ala Leu Leu Leu Ile Val Leu Pro Met Val Phe Ser
 65                 70                  75                  80 ccg gct cac agc tgc ggt cct ggc cga gga ttg ggt cgt cat agg gcg     288
Pro Ala His Ser Cys Gly Pro Gly Arg Gly Leu Gly Arg His Arg Ala
                 85                  90                  95 cgc aac ctg tat ccg ctg gtc ctc aag cag aca att ccc aat cta tcc     336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg     384
Glu Tyr Thr Asn Ser Ala Ser Gly Pro Leu Glu Gly Val Ile Arg Arg
        115                 120                 125 gat tcg ccc aaa ttc aag gac ctc gtg ccc aac tac aac agg gac atc     432
Asp Ser Pro Lys Phe Lys Asp Leu Val Pro Asn Tyr Asn Arg Asp Ile
    130                 135                 140
```

```
                                             -continued ctt ttc cgt gac gag gaa ggc acc gga gcg gat ggc ttg atg agc aag    480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa    528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac    576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att    624
His His Gly Gln Glu Ser Leu His Tyr Glu Gly Arg Ala Val Thr Ile
        195                 200                 205 gcc acc tcc gat cgc gac cag tcc aaa tac ggc atg ctc gct cgc ctg    672
Ala Thr Ser Asp Arg Asp Gln Ser Lys Tyr Gly Met Leu Ala Arg Leu
    210                 215                 220 gcc gtc gag gct gga ttc gat tgg gtc tcc tac gtc agc agg cgc cac    720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac    768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg    816
Gly Cys Phe Thr Pro Glu Ser Thr Ala Leu Leu Glu Ser Gly Val Arg
            260                 265                 270 aag ccg ctc ggc gag ctc tct atc gga gat cgt gtt ttg agc atg acc    864
Lys Pro Leu Gly Glu Leu Ser Ile Gly Asp Arg Val Leu Ser Met Thr
        275                 280                 285 gcc aac gga cag gcc gtc tac agc gaa gtg atc ctc ttc atg gac cgc    912
Ala Asn Gly Gln Ala Val Tyr Ser Glu Val Ile Leu Phe Met Asp Arg
    290                 295                 300 aac ctc gag cag atg caa aac ttt gtg cag ctg cac acg gac ggt gga    960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg   1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag   1056
Glu Ser Gln Lys Leu Thr Phe Val Phe Ala His Arg Ile Glu Glu Lys
            340                 345                 350 aac cag gtg ctc gta cgg gat gtg gag acg ggc gag ctg agg ccc cag   1104
Asn Gln Val Leu Val Arg Asp Val Glu Thr Gly Glu Leu Arg Pro Gln
        355                 360                 365 cga gtg gtc aag ttg ggc agt gtg cgc agt aag ggc gtg gtc gcg ccg   1152
Arg Val Val Lys Leu Gly Ser Val Arg Ser Lys Gly Val Val Ala Pro
    370                 375                 380 ctg acc cgc gag ggc acc att gtg gtc aac tcg gtg gcc gcc agt tgc   1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc   1248
Tyr Ala Val Ile Asn Ser Gln Ser Leu Ala His Trp Gly Leu Ala Pro
                405                 410                 415 atg cgc ctg ctg tcc acg ctg gag gcg tgg ctg ccc gcc aag gag cag   1296
Met Arg Leu Leu Ser Thr Leu Glu Ala Trp Leu Pro Ala Lys Glu Gln
            420                 425                 430 ttg cac agt tcg ccg aag gtg gtg agc tcg gcg cag cag cag aat ggc   1344
Leu His Ser Ser Pro Lys Val Val Ser Ser Ala Gln Gln Gln Asn Gly
        435                 440                 445 atc cat tgg tat gcc aat gcg ctc tac aag gtc aag gac tac gtg ctg   1392
Ile His Trp Tyr Ala Asn Ala Leu Tyr Lys Val Lys Asp Tyr Val Leu
    450                 455                 460
```

-continued

```
ccg cag agc tgg cgc cac gat tga                              1416
Pro Gln Ser Trp Arg His Asp
465                 470
```

<210> SEQ ID NO 20
<211> LENGTH: 471
<212> TYPE: PRT
<213> ORGANISM: Drosophila sp.

<400> SEQUENCE: 20

```
Met Asp Asn His Ser Ser Val Pro Trp Ala Ser Ala Ser Val Thr
 1               5                  10                  15

Cys Leu Ser Leu Gly Cys Gln Met Pro Gln Phe Gln Phe Gln Phe Gln
                20                  25                  30

Leu Gln Ile Arg Ser Glu Leu His Leu Arg Lys Pro Ala Arg Arg Thr
                35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Arg Gly Leu Gly Arg His Arg Ala
                85                  90                  95

Arg Asn Leu Tyr Pro Leu Val Leu Lys Gln Thr Ile Pro Asn Leu Ser
                100                 105                 110

Glu Tyr Thr Asn Ser Ala Ser Gly Pro Leu Glu Gly Val Ile Arg Arg
                115                 120                 125

Asp Ser Pro Lys Phe Lys Asp Leu Val Pro Asn Tyr Asn Arg Asp Ile
130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
                195                 200                 205

Ala Thr Ser Asp Arg Asp Gln Ser Lys Tyr Gly Met Leu Ala Arg Leu
210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
                260                 265                 270

Lys Pro Leu Gly Glu Leu Ser Ile Gly Asp Arg Val Leu Ser Met Thr
                275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
                340                 345                 350
```

```
Asn Gln Val Leu Val Arg Asp Val Glu Thr Gly Glu Leu Arg Pro Gln
        355                 360                 365

Arg Val Val Lys Leu Gly Ser Val Arg Ser Lys Gly Val Val Ala Pro
        370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Gln Asn Gly
        435                 440                 445

Ile His Trp Tyr Ala Asn Ala Leu Tyr Lys Val Lys Asp Tyr Val Leu
    450                 455                 460

Pro Gln Ser Trp Arg His Asp
465                 470

<210> SEQ ID NO 21
<211> LENGTH: 221
<212> TYPE: PRT
<213> ORGANISM: Artificial Sequence
<220> FEATURE:
<223> OTHER INFORMATION: Description of Artificial Sequence: degenerate
      polypeptide sequence
<222> LOCATION: 7
<223> OTHER INFORMATION: Gly, Ala, Val, Leu, Ile, Phe, Tyr or Trp
<222> LOCATION: 9
<223> OTHER INFORMATION: Arg, His or Lys
<222> LOCATION: 44
<223> OTHER INFORMATION: Gly, Ala, Val, Leu, Ile, Ser or Thr
<222> LOCATION: 85
<223> OTHER INFORMATION: Gly, Ala, Val, Leu, Ile, Ser or Thr
<222> LOCATION: 93
<223> OTHER INFORMATION: Lys, Arg, His, Asn or Gln
<222> LOCATION: 98
<223> OTHER INFORMATION: Lys, Arg or His
<222> LOCATION: 112
<223> OTHER INFORMATION: Ser, Thr, Tyr, Trp or Phe
<222> LOCATION: 132
<223> OTHER INFORMATION: Lys, Arg or His
<222> LOCATION: 137
<223> OTHER INFORMATION: Met, Cys, Ser or Thr
<222> LOCATION: 139
<223> OTHER INFORMATION: Gly, Ala, Val, Leu, Ile, Ser or Thr
<222> LOCATION: 181
<223> OTHER INFORMATION: Leu, Val, Met, Thr or Ser
<222> LOCATION: 183
<223> OTHER INFORMATION: His, Phe, Tyr, Ser, Thr, Met or Cys
<222> LOCATION: 185
<223> OTHER INFORMATION: Gln, Asn, Glu, or Asp
<222> LOCATION: 186
<223> OTHER INFORMATION: His, Phe, Tyr, Thr, Gln, Asn, Glu or Asp
<222> LOCATION: 189
<223> OTHER INFORMATION: Gln, Asn, Glu, Asp, Thr, Ser, Met or Cys
<222> LOCATION: 191
<223> OTHER INFORMATION: Ala, Gly, Cys, Leu, Val or Met
<222> LOCATION: 196
<223> OTHER INFORMATION: Arg, Lys, Met, Ile, Asn, Asp, Glu, Gln, Ser,
      Thr or Cys
<222> LOCATION: 200
<223> OTHER INFORMATION: Arg, Lys, Met or Ile
<222> LOCATION: 206
<223> OTHER INFORMATION: Ala, Gly, Cys, Asp, Glu, Gln, Asn, Ser, Thr or
      Met
<222> LOCATION: 207
<223> OTHER INFORMATION: Ala, Gly, Cys, Asp, Asn, Glu or Gln
<222> LOCATION: 209
<223> OTHER INFORMATION: Arg, Lys, Met, Ile, Asn, Asp, Glu or Gln
<222> LOCATION: 211
<223> OTHER INFORMATION: Leu, Val, Met or Ile
<222> LOCATION: 212
```

```
<223> OTHER INFORMATION: Phe, Tyr, Thr, His or Trp
<222> LOCATION: 216
<223> OTHER INFORMATION: Ile, Val, Leu or Met
<222> LOCATION: 217
<223> OTHER INFORMATION: Met, Cys, Ile, Leu, Val, Thr or Ser
<222> LOCATION: 219
<223> OTHER INFORMATION: Leu, Val, Met, Thr or Ser
<223> OTHER INFORMATION: each Xaa may also be any amino acid.

<400> SEQUENCE: 21

Cys Gly Pro Gly Arg Gly Xaa Gly Xaa Arg Arg His Pro Lys Lys Leu
 1               5                  10                  15

Thr Pro Leu Ala Tyr Lys Gln Phe Ile Pro Asn Val Ala Glu Lys Thr
                20                  25                  30

Leu Gly Ala Ser Gly Arg Tyr Glu Gly Lys Ile Xaa Arg Asn Ser Glu
            35                  40                  45

Arg Phe Lys Glu Leu Thr Pro Asn Tyr Asn Pro Asp Ile Ile Phe Lys
        50                  55                  60

Asp Glu Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                85                  90                  95

Val Xaa Leu Arg Val Thr Glu Gly Trp Asp Glu Asp Gly His His Xaa
                100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
                180                 185                 190

Lys Asp Leu Xaa Pro Gly Asp Xaa Val Leu Ala Ala Asp Xaa Xaa Gly
            195                 200                 205

Xaa Leu Xaa Xaa Ser Asp Phe Xaa Xaa Phe Xaa Asp Arg
210                 215                 220

<210> SEQ ID NO 22
<211> LENGTH: 167
<212> TYPE: PRT
<213> ORGANISM: Artificial Sequence
<220> FEATURE:
<223> OTHER INFORMATION: Description of Artificial Sequence: degenerate
      polypeptide sequence
<222> LOCATION: 7
<223> OTHER INFORMATION: Gly, Ala, Val, Leu, Ile, Pro, Phe or Tyr
<222> LOCATION: 8
<223> OTHER INFORMATION: Gly, Ala, Val, Leu or Ile
<222> LOCATION: 9
<223> OTHER INFORMATION: Gly, Ala, Val, Leu, Ile, Lys, His or Arg
<222> LOCATION: 12
<223> OTHER INFORMATION: Lys, Arg or His
<222> LOCATION: 13
<223> OTHER INFORMATION: Phe, Trp, Tyr or an amino acid gap
<222> LOCATION: 14
<223> OTHER INFORMATION: Gly, Ala, Val, Leu, Ile or an amino acid gap
<222> LOCATION: 17
<223> OTHER INFORMATION: Asn, Gln, His, Arg or Lys
<222> LOCATION: 19
<223> OTHER INFORMATION: Gly, Ala, Val, Leu, Ile, Ser or Thr
<222> LOCATION: 22
<223> OTHER INFORMATION: Gly, Ala, Val, Leu, Ile, Ser or Thr
```

```
<222> LOCATION: 27
<223> OTHER INFORMATION: Gly, Ala, Val, Leu, Ile, Ser or Thr
<222> LOCATION: 29
<223> OTHER INFORMATION: Ser, Thr, Gln or Asn
<222> LOCATION: 30
<223> OTHER INFORMATION: Met, Cys, Gly, Ala, Val, Leu, Ile, Ser or Thr
<222> LOCATION: 31
<223> OTHER INFORMATION: Gly, Ala, Val, Leu, Ile or Pro
<222> LOCATION: 33
<223> OTHER INFORMATION: Arg, His or Lys
<222> LOCATION: 40
<223> OTHER INFORMATION: Gly, Ala, Val, Leu, Ile, Pro, Arg, His or Lys
<222> LOCATION: 41
<223> OTHER INFORMATION: Gly, Ala, Val, Leu, Ile, Phe or Tyr
<222> LOCATION: 44
<223> OTHER INFORMATION: Arg, His or Lys
<222> LOCATION: 45
<223> OTHER INFORMATION: Gly, Ala, Val, Leu, Ile, Ser or Thr
<222> LOCATION: 46
<223> OTHER INFORMATION: Thr or Ser
<222> LOCATION: 48
<223> OTHER INFORMATION: Gly, Ala, Val, Leu, Ile, Asn or Gln
<222> LOCATION: 53
<223> OTHER INFORMATION: Arg, His or Lys
<222> LOCATION: 54
<223> OTHER INFORMATION: Asp or Glu
<222> LOCATION: 71
<223> OTHER INFORMATION: Ser or Thr
<222> LOCATION: 79
<223> OTHER INFORMATION: Glu, Asp, Gln or Asn
<222> LOCATION: 83
<223> OTHER INFORMATION: Glu or Asp
<222> LOCATION: 84
<223> OTHER INFORMATION: Arg, His or Lys
<222> LOCATION: 85
<223> OTHER INFORMATION: Gly, Ala, Val, Leu or Ile
<222> LOCATION: 87
<223> OTHER INFORMATION: Gly, Ala, Val, Leu, Ile, Thr or Ser
<222> LOCATION: 95
<223> OTHER INFORMATION: Met, Cys, Gln, Asn, Arg, Lys or His
<222> LOCATION: 100
<223> OTHER INFORMATION: Arg, His or Lys
<222> LOCATION: 107
<223> OTHER INFORMATION: Trp, Phe, Tyr, Arg, His or Lys
<222> LOCATION: 114
<223> OTHER INFORMATION: Gly, Ala, Val, Leu, Ile, Ser, Thr, Tyr or Phe
<222> LOCATION: 115
<223> OTHER INFORMATION: Gln, Asn, Asp or Glu
<222> LOCATION: 116
<223> OTHER INFORMATION: Asp or Glu
<222> LOCATION: 125
<223> OTHER INFORMATION: Gly, Ala, Val, Leu, or Ile
<222> LOCATION: 134
<223> OTHER INFORMATION: Arg, His or Lys
<222> LOCATION: 135
<223> OTHER INFORMATION: Asn, Gln, Thr or Ser
<222> LOCATION: 139
<223> OTHER INFORMATION: Gly, Ala, Val, Leu, Ile, Ser, Thr, Met or Cys
<222> LOCATION: 141
<223> OTHER INFORMATION: Gly, Ala, Val, Leu, Ile, Thr or Ser
<222> LOCATION: 157
<223> OTHER INFORMATION: Arg, His or Lys
<222> LOCATION: 158
<223> OTHER INFORMATION: Asn, Gln, Gly, Ala, Val, Leu or Ile
<222> LOCATION: 160
<223> OTHER INFORMATION: Gly, Ala, Val, Leu or Ile
<222> LOCATION: 162
<223> OTHER INFORMATION: Gly, Ala, Val, Leu, Ile, Ser, Thr or Cys
<222> LOCATION: 166
<223> OTHER INFORMATION: Gly, Ala, Val, Leu, Ile, Thr or Ser
<222> LOCATION: 167
<223> OTHER INFORMATION: Asp or Glu

<400> SEQUENCE: 22

Cys Gly Pro Gly Arg Gly Xaa Xaa Xaa Arg Arg Xaa Xaa Xaa Pro Lys
 1               5                  10                  15

Xaa Leu Xaa Pro Leu Xaa Tyr Lys Gln Phe Xaa Pro Xaa Xaa Xaa Glu
```

-continued

```
                  20                  25                  30
Xaa Thr Leu Gly Ala Ser Gly Xaa Xaa Glu Gly Xaa Xaa Xaa Arg Xaa
            35                  40                  45
Ser Glu Arg Phe Xaa Xaa Leu Thr Pro Asn Tyr Asn Pro Asp Ile Ile
    50                  55                  60
Phe Lys Asp Glu Glu Asn Xaa Gly Ala Asp Arg Leu Met Thr Xaa Arg
65                  70                  75                  80
Cys Lys Xaa Xaa Xaa Asn Xaa Leu Ala Ile Ser Val Met Asn Xaa Trp
            85                  90                  95
Pro Gly Val Xaa Leu Arg Val Thr Glu Gly Xaa Asp Glu Asp Gly His
            100                 105                 110
His Xaa Xaa Xaa Ser Leu His Tyr Glu Gly Arg Ala Xaa Asp Ile Thr
        115                 120                 125
Thr Ser Asp Arg Asp Xaa Xaa Lys Tyr Gly Xaa Leu Xaa Arg Leu Ala
        130                 135                 140
Val Glu Ala Gly Phe Asp Trp Val Tyr Tyr Glu Ser Xaa Xaa His Xaa
145                 150                 155                 160
His Xaa Ser Val Lys Xaa Xaa
            165
```

METHODS OF MODULATING LIPID METABOLISM AND STORAGE

RELATED APPLICATIONS

This is a continuation of PCT/US00/05662 filed on Mar. 3, 2000 as a continuation-in-part of prior U.S. provisional Ser. No. 60/122,640 filed on Mar. 3, 1999 and U.S. provisional Ser. No. 60/124,446 filed on Mar. 15, 1999. The entire disclosure of each of the aforesaid patent applications are incorporated herein by reference.

FIELD OF THE INVENTION

This invention relates generally to methods for modulating the metabolism and storage of lipids. The invention relates particularly to the use of lipid metabolism and storage modulators such as agonists or antagonists of hedgehog activity to alter the metabolism of lipids in the gastrointestinal tract, as well as to alter the storage of lipids in gut epithelial tissue.

BACKGROUND OF THE INVENTION

Pathological conditions that affect storage, breakdown and intestinal absorption of lipids are included in a broad category of so-called "lipid metabolism disorders," and there are a variety of disorders that have been diagnosed. These include: diet-induced and regular hypercholesterolemia (Farese et al. *Proc. Natl. Acad. Sci. USA* 1995 92:1774–1778), abetalipoproteinemia and hypobetalipoproteinemia (Linton et al. *J. Lipid Res.*1993 34:521–541.) Several other lipid metabolism disorders of unknown origin have also been identified including Anderson's disease (Anderson et al. *Med. J. Aust.* 1961 11:617–621), and atherosclerosis (Purcell-Huynh et al. *J. Clin. Invest.* 1995 95:2246–2257.) General symptoms of lipid metabolism disorders include, but are not limited to, chronic diarrhea, inadequate weight gain or weight loss, inability to lose excess weight and general failure to thrive. (Case 35–1999, New England Journal of Medicine; 327: 628–635 1992.) The various lipid metabolism disorders have been thought to originate through aberrant expression of apolipoproteins and/or regulation of genes responsible for various aspects of lipid metabolism.

Apo-B is synthesized by the intestine and the liver in mammals, where it serves as the main structural component in the formation of chylomicrons and the synthesis of very low-density (VLDL), low-density (LDL) and indeterminate (IDL) lipoproteins. The formation of chylomicrons by the intestine is very important for the absorption and transport dietary fats and fat-soluble vitamins. Genetically modified mice that express apo-B in the liver, but not in the intestine can not form chylomicrons. (Young et al. *J. Cli. Invest.* 1995 96:2932–2946.) In fact, apolipoprotein knock-out mice exhibit early death (death at embryonic day 11.5) and impaired lipoprotein formation in the yolk sac. (Farese et al. *Proc. Natl. Acad. Sci. USA* 1995 92:1774–1778.)

The various lipid metabolism disorders are also thought to originate via malfunctions in embryonic tissue development. The generation of the intestines from the embryonic gut material depends solely on intercellular signaling between endodermal and mesodermal cells of the gut. It has been widely recognized that the hedgehog-signaling pathway plays a critical role in the direction of specialized mesoderm differentiation in the intestine and pancreas. (Apelqvist et al. *Current Biology* 1997 7:801–804.) Hedgehog is initially expressed in mouse embryos in the ventral part of the foregut endoderm, and has been shown to mediate endodermally derived signals in embryonic hindgut. (Id.) Specifically, mice with targeted deletion of hedgehog have evident foregut defects that are apparent as early as embryonic day 9.5, when the tracheal diverticulum begins to outgrow, suggesting that hedgehog and its signaling components are involved in foregut defects in humans. (Litingtung et al. *Nature Genetics* 1998 20:58–60.) See also Yang et al. *Molecular Medicine* 1997 3:826–835.

Many attempts to treat lipid metabolism disorders have been made with little practical success. (Case 35–1999, New England Journal of Medicine; 327: 628–635 1992.) There are currently no treatments that address lipid metabolism disorders by modulating their metabolism at the source, namely, the intestine. Nor are there any treatments that can potentially eliminate the disorder in and of itself. Therefore, it would be desirable to develop a method of treatment that could modulate lipid metabolism in the intestine. It would also be desirable to develop a method of therapy that could treat a lipid metabolism disorder for the sole purpose of substantially eliminating the disorder.

SUMMARY OF THE INVENTION

This invention is based on part on our discovery that the hedgehog-signaling pathway may play a role in the intestinal metabolism of lipids, including regulation of apolipoprotein expression, endogenous cholesterol synthesis and uptake of exogenous dietary cholesterol. Specifically, our discoveries support the role of the hedgehog-mediated signaling pathway in the metabolism and storage of lipids.

It would be useful to develop methods using hedgehog agonists or antagonists that would act as modulators of lipid metabolism and storage and, consequently, act as modulators of the effects and symptoms of certain lipid metabolism disorders. We have solved this problem by developing methods of modulating lipid metabolism and storage using hedgehog modulators that are capable of binding to the hedgehog receptor without eliciting signaling by hedgehog and, thus, serve as antagonists to hedgehog activity. We have also developed methods of modulating lipid metabolism and storage using hedgehog modulators that act as hedgehog antagonists by binding to the hedgehog protein and thus, inhibit or compete with hedgehog's ability to bind to its receptor. Further, we have developed methods of modulating lipid metabolism and storage using modulators that are versions of hedgehog and related small molecules that are capable of binding to, or enhancing the binding affinity of hedgehog and, thus, act as agonists. Further, we have developed methods of modulating lipid metabolism using hedgehog modulators that are antibodies acting as as antagonists, in that they are capable of binding to hedgehog, and thus, block it from binding to its receptor.

One aspect of the present invention relates to a method for modulating lipid metabolism in a subject. Briefly, the subject method comprises administering a pharmaceutically effective amount of a composition containing a hedgehog modulator. The modulator can be either a hedgehog antagonist or agonist in a pharmaceutically effective amount.

In other embodiments, the methods of the present invention can be used to modulate the formation of vacuoles in gut epithelial cells in a subject.

In another embodiment, the methods of the present invention can be used to control the sequestering of lipids in gut epithelial cells.

In still other embodiments, the methods of the present invention can be used for preventing or for treating a variety of lipid metabolism disorders, including: preventing, treating or protecting a subject from cholesterol-related disorders; preventing or treating atherosclerosis; preventing or treating apolipoprotein disorders, including apo-B deficiency disorders; preventing or treating abetalipoproteinemia and normotriglyceridemic abetalipoproteinemia; for treating hypobetalipoproteinemia; for treating chylmicron-retention diseases; for treating vitamin A and E malabsorption and deficiency disorders; and for treating, preventing or protecting from obesity.

In one embodiment, the present invention provides a method for the treatment of a lipid metabolism disorder utilizing a pharmaceutically effective composition containing, as an active ingredient, a hedgehog modulator. In one of the preferred embodiments, the invention contemplates using a modulator to control lipid metabolism in a subject afflicted with a lipid metabolism disorder involving accumulation of lipid material in intestinal epithelial cells or tissues.

In another embodiment, the invention contemplates using a hedgehog modulator to modulate lipid metabolism in a subject afflicted with a lipid metabolism disorder, including, but not limited to, obesity.

In preferred embodiments, the hedgehog modulator is a hedgehog antagonist selected from the group consisting of a hedgehog mimetic, or an active fragment thereof; a modified hedgehog protein, or an active fragment thereof; a hedgehog variant; or an anti-hedgehog homolog. The anti-hedgehog homolog can be a human antibody, a chimeric antibody, a humanized antibody or any active fragments thereof.

In certain embodiments, the subject method is carried out using a modulator which is a hedgehog agonist that is capable of binding to the hedgehog receptor with, at least the same, if not a higher, binding affinity as the hedgehog protein.

Another aspect of the present invention relates to a therapeutic preparation of a small molecule hedgehog modulator therapeutic, in which the modulator is either a hedgehog antagonist or agonist provided in a pharmaceutically acceptable carrier in an amount sufficient to treat a lipid metabolism disorder.

DETAILED DESCRIPTION OF THE INVENTION

I. Overview

Figure 1:
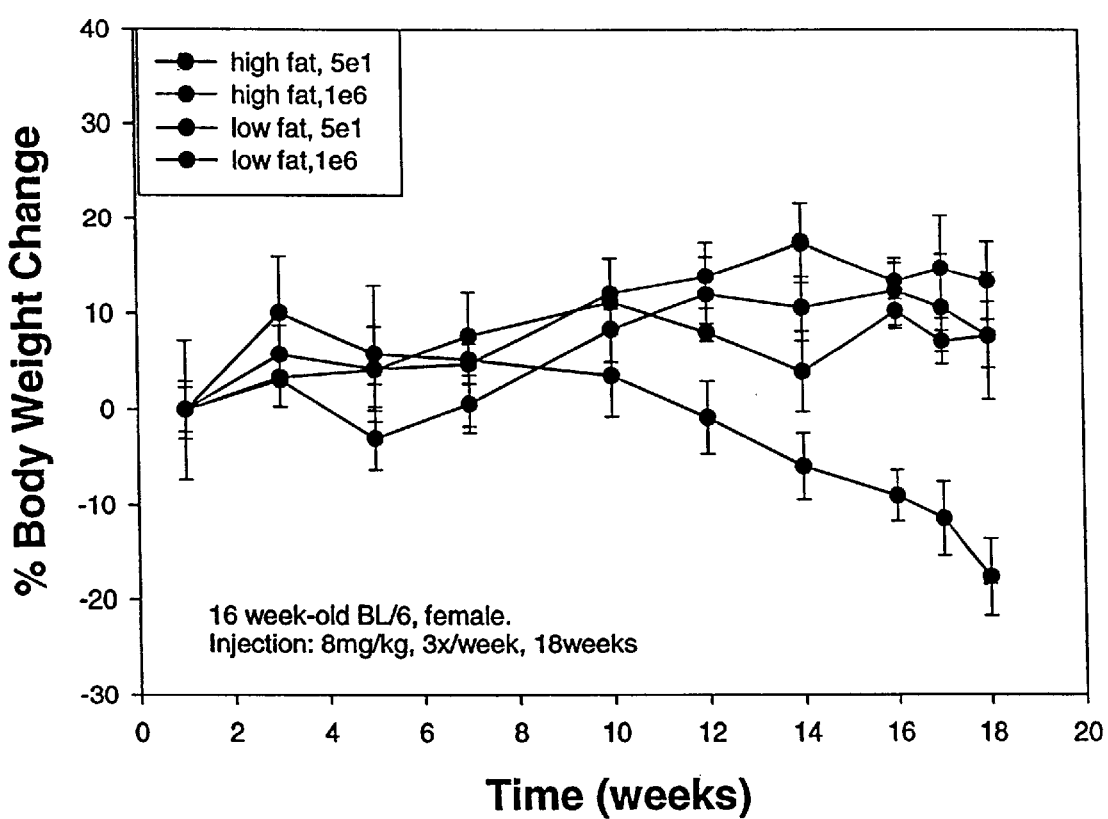
FIG. 1: Three week old BALB/c mice (n=4) and 16 week old BL/6 mice (n=4) were injected with control 1E6 mab or hedgehog antagonist 5E1 mab (8 mg/kg; three times per week) for 18 weeks. Mice were subject to either chow diet or high fat diet (19.2% fat) from the beginning of antibody treatments. Body weight was measured every week and is shown as a percentage of weight change as compared to the first weeks weight post treatment.

In experiments conducted in the course of the present invention, treatment of both prenatal and post-natal mice with anti-hedgehog antibodies resulted in failure to thrive, runting, diarrhea and early death. Histological analysis of these mice revealed prominent apical or subnuclear vacuole formation and lipid accumulation within the vacuoles of the intestinal epithelial cells. These symptoms were induced through blockage of the hedgehog-signaling pathway, and are those most closely associated with a variety of lipid metabolism and storage disorders.

The present application is directed to the discovery that preparations of lipid metabolism and storage modulators (herein referred to as "lipid modulator") can be used to control the storage, breakdown and intestinal absorption of lipids. In general, the method of the present invention can be characterized as including a step of administering a pharmaceutically effective amount of a lipid modulator which alters the metabolism and storage of a lipid. The lipid modulator is most preferably a hedgehog antagonist or agonist. The subject method can be most preferably carried out on intestinal epithelial cells, which may be part of an intact tissue or organ.

II. Definitions

For convenience, certain terms employed in the specification, examples, and appended claims are collected here. All citations are incorporated herein by reference, unless specified otherwise.

As used herein, the term "lipid modulator" includes any compound that in any way acts to alter or modulate lipid metabolism and storage; the term "modulate" means to regulate according to measure or proportion. The most preferred lipid modulators of the present invention are hedgehog agonists or antagonists (defined infra), agonist or antagonist meaning, respectively, that it either agonizes or antagonizes the hedgehog signaling pathway, thus leading to the alteration of lipid metabolism and storage.

As used herein, the term "hedgehog antagonist" includes any compound that inhibits hedgehog from binding with its receptor. For the purposes of the invention a "hedgehog antagonist" refers to an agent, e.g., a polypeptide such as an anti-hedgehog or anti-patched antibody which can inhibit or block hedgehog and/or patched-mediated binding or which can otherwise modulate hedgehog and/or patched function, e.g., by inhibiting or blocking hedgehog-ligand mediated hedgehog signal transduction. Such an antagonist of the hedgehog/patched interaction is an agent which has one or more of the following properties: (1) it coats, or binds to, a hedgehog on the surface of a hedgehog bearing or secreting cell with sufficient specificity to inhibit a hedgehog-ligand/hedgehog interaction, e.g., the hedgehog/patched interaction; (2) it coats, or binds to, a hedgehog on the surface of a hedgehog-bearing or secreting cell with sufficient specificity to modify, and preferably to inhibit, transduction of a hedgehog-mediated signal e.g., hedgehog/patched-mediated signaling; (3) it coats, or binds to, a hedgehog receptor, (e.g., patched) in or on cells with sufficient specificity to inhibit the hedgehog /patched interaction; (4) it coats, or binds to, a hedgehog receptor (e.g., patched) in or on cells with sufficient specificity to modify, and preferably to inhibit, transduction of hedgehog mediated hedgehog signaling, e.g., patched-mediated hedgehog signaling. Characteristic four is a specific antagonist called a functional antagonist. A functional antagonist has at least the following properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH3H10T1/2 cell-based AP induction assay.

In preferred embodiments the antagonist has one or both of properties 1 and 2. In other preferred embodiments the antagonist has one or both of properties 3 and 4. Moreover, more than one antagonist can be administered to a patient, e.g., an agent which binds to hedgehog can be combined with an agent which binds to patched. As discussed herein, the antagonists used in methods of the invention are not limited to a particular type or structure of molecule so that, for purposes of the invention, any agent capable of binding to hedgehog antigens and which effectively blocks or coats hedgehog is considered to be an equivalent of the antagonists used in the examples herein.

For example, antibodies or antibody homologs (discussed below) as well as other molecules such as soluble forms of the natural binding proteins for hedgehog are useful. Soluble forms of the natural binding proteins for hedgehog include soluble patched peptides, patched fusion proteins, or bifunctional patched/Ig fusion proteins. For example, a soluble form of patched or a fragment thereof may be administered to bind to hedghog, and preferably compete for a hedgehog binding site on cells, thereby leading to effects similar to the administration of antagonists such as anti-hedgehog antibodies. In particular, soluble hedgehog mutants that bind patched but do not elicit hedgehog-dependent signaling are included within the scope of the invention. Such hedgehog mutants can act as competitive inhibitors of wild type hedgehog protein and are considered "antagonists".

The most preferred embodiments are patched or hedgehog antagonists used in the method of the invention to bind to, including block or coat, cell-surface hedgehog or patched. These compositions include monoclonal antibody such an anti-hedgehog or anti-patched antibody homolog. Preferred antibodies and homologs for treatment, in particular for human treatment, include human antibody homologs, humanized antibody homologs, chimeric antibody homologs, Fab, Fab', F(ab')2 and F(v) antibody fragments, and monomers or dimers of antibody heavy or light chains or mixtures thereof. Thus, monoclonal antibodies against hedgehog are the preferred binding agent in the method of the invention.

The subject treatments are effective on both human and animal subjects afflicted with these conditions. Animals subject to conditions of which the invention is applicable extend to both domestic animals and livestock, raised either as pets or for commercial purposes. Examples are dogs, cats, cattle, horses, sheep, hogs and goats.

As used herein, the term "hedgehog agonist" includes any compound that activates the hedgehog receptor.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., hedgehog or patched). The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof), wherein the light chains of the immunoglobulin may be of types kappa or lambda. "Antibody homologs" also include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain. In another aspect the invention features a variant of a chimeric molecule which includes: (1) a hedgehog targeting moiety, e.g., a patched moiety capable of binding to antigen (i.e., hedgehog); (2) optionally, a second peptide, e.g., one which increases solubility or in vivo life time of the hedgehog targeting moiety, e.g., a member of the immunoglobulin super family or fragment or portion thereof, e.g., a portion or a fragment of IgG, e.g., the human IgG1 heavy chain constant region, e.g., CH2 and CH3 hinge regions; and a toxin moiety. The hedgehog targeting moiety can be any naturally occurring hedgehog ligand or fragment thereof, e.g., a patched peptide or a similar conservatively substituted amino acid sequence. A preferred targeting moiety is a soluble patched fragment. The chimeric molecule can be used to treat a subject, e.g., a human, at risk for disorder related to proliferation of epithelial cells such as hair follicles and the like.

As used herein, a "human antibody homolog" is an antibody homolog produced by recombinant DNA technology, in which all of the amino acids of an immunoglobulin light or heavy chain that are derived from a human source.

As used herein, "amino acid" is a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

As used herein, the term "protein" is any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

As used herein, the term "N-terminal end" refers to the first amino acid (amino acid number 1) of the mature form of a protein, the "mature form" of a protein comprising the primary amino acid sequence after removal of any signal, or other sequence.

As used herein, the term "fragment," as applied to an isolated antagonist, can be as small as a single amino acid provided that it retains antagonist activity. It may be at least about 10 residues, more typically at least about 40 residues, preferably at least about 100 residues in length. Fragments can be generated by methods known to those skilled in the art. The ability of a candidate fragment to exhibit isolated hedgehog biological activity can be also assessed by methods known to those skilled in the art as described herein.

As used herein, the term "functional equivalent" of a hedgehog antagonist of the invention is an agent that may have different amino acid residues as the hedgehog antagonist but acts as a functional antagonist nonetheless. "fusion"- refers to a co-linear linkage of two or more proteins or fragments thereof via their individual peptide backbones through genetic expression of a polynucleotide molecule encoding those proteins. It is preferred that the proteins or fragments thereof be from different sources. Thus, preferred fusion proteins include an hedgehog protein or fragment covalently linked to a second moiety that is not an hedgehog. Specifically, an "hedgehog protein/ Ig fusion" is a protein comprising an hedgehog protein of the invention, or fragment thereof linked to an N-terminus of an immunoglobulin chain wherein a portion of the N-terminus of the immunoglobulin is replaced with the hedgehog protein. In general, a fusion protein can be represented by the general formula X-hh-Y, wherein hh represents a portion of the protein which is derived from one of the vertebrate hh proteins, and X and Y are independently absent or represent amino acid sequences which are not related to one of the vertebrate hh sequences in an organism, including naturally occurring mutants.

As used herein, the term "genetic fusion" refers to a co-linear, covalent linkage of two or more proteins or fragments thereof via their individual peptide backbones, through genetic expression of a polynucleotide molecule encoding those proteins.

As used herein, the term "vesicle" refers to any aggregate of lipophilic molecules. The vesicle may be obtained from a biologic source (e.g., a lipid bilayer such as a cell membrane or a cholic acid-derived detergent preparation) or from a non-biologic source (e.g., a non-biologic detergent vesicle). The shape, type, and configuration of the vesicle is not intended to limit the scope of this invention.

As used herein, the term "mutant" is any change in the genetic material of an organism, in particular any change (i.e., deletion, substitution, addition, or alteration) in a wild-type polynucleotide sequence or any change in a wild-type protein.

As used herein, the term "wild-type" is the naturally-occurring polynucleotide sequence of an exon of a protein, or a portion thereof, or protein sequence, or portion thereof, respectively, as it normally exists in vivo.

As used herein, the term "standard hybridization conditions" refers to salt and temperature conditions substantially equivalent to 0.5×SSC to about 5×SSC and 65 (C for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulphate, and 100 (g/ml denatured, sonicated salmon sperm DNA at 65 (C for 12–20 hours, and washing with 75 mM NaCl/7.5 mM sodium citrate (0.5×SSC)/1% SDS at 65(C. Lower stringency conditions may, for example, include hybridizing with plaque screen buffer, 10% dextran sulphate and 110 (g/ml denatured, sonicated salmon sperm DNA at 55 (C for 12–20 hours, and washing with 300 mM NaCl/30 mM sodium citrate (2.0×SSC)/1% SDS at 55 (C. See also Current Protocols in Molecular Biology, John Wiley & Sons, Inc. New York, Sections 6.3.1–6.3.6, (1989).

As used herein, the term "expression vector" refers to a polynucleotide, such as a DNA plasmid or phage (among other common examples) which allows expression of at least one gene when the expression vector is introduced into a host cell. The vector may, or may not, be able to replicate in a cell.

As used herein, the term "isolated" (used interchangeably with "substantially pure") refers to when applied to nucleic acid i.e., polynucleotide sequences, that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) chemically synthesized; (iii) recombinantly produced by cloning; or (iv) purified, as by cleavage and gel separation. Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional hedgehog sequences.

As used herein, the term "isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is : (i) chemically synthesized; or (ii) expressed in a host cell and purified away from associated proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

As used herein, the term "heterologous promoter" is a promoter that is not naturally associated with a gene or a purified nucleic acid.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by a similar amino acid (e.g., similar in steric and/or electronic nature), then the molecules can be refered to as homologous at that position. The percentage homology between two sequences is a function of the number of matching or homologous positions shared by the two sequences divided by the number of positions compared× 100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). An "unrelated" or "non-homologous" sequence shares less than 40 percent identity, though preferably less than 25 percent identity, with a sequence of the present invention. Generally, a comparison is made when two sequences are aligned to give maximum homology. Such alignment can be provided using, for instance, the method of Needleman et al., *J. Mol Biol.* 48: 443–453 (1970), implemented conveniently by computer programs described in more detail below. Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354–352, Nat. Biomed. Res. Foundation, Washington, D.C. (1978). Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The term "Hedgehog N-terminal fragment" is used interchangeably with "Hedgehog" and refers to the active mature sequence that is proteolytically cleaved from the hedgehog precursor.

The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms.

The phrase "internal amino acid" means any amino acid in a peptide sequence that is neither the N-terminal amino acid nor the C-terminal amino acid.

A "hedgehog protein" of the invention is defined in terms of having at least a portion that consists of the consensus amino acid sequence as disclosed in U.S. patent application No. 60/067,423. The term also means a hedgehog polypeptide, or a functional variant of a hedgehog polypeptide, or homolog of a hedgehog polypeptide, or functional variant, which has biological activity.

The terms "peptide(s)", "protein(s)" and "polypeptide(s)" are used interchangeably herein. The terms "polynucleotide sequence" and "nucleotide sequence" are also used interchangeably herein. The term "Hedgehog fragment" is used interchangeably with "Hedgehog". Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

A hedgehog molecule has "biological activity" if it has at least one of the following properties: (i) the molecule meets the hedgehog consensus criteria as defined herein e.g., (SEQ ID NOS:21 or 22) and has the ability to bind to its receptor, patched-1 or it encodes, upon expression, a polypeptide that has this characteristic; (ii) the molecule meets the hedgehog consensus criteria as defined herein or it encodes, upon expression, a polypeptide that has this characteristic; and (iii) it induces alkaline phosphatase activity in C3H 10 T1/2 cells.

The term "patched" or "ptc" refers to a family of related transmembrane proteins that have been implicated in the signal transduction induced by contacting a cell with a hedgehog protein. For example, the mammalian ptc family includes ptc1 and ptc2.

As used herein, the term 'gene' or 'recombinant gene' refers to a nucleic acid comprising an open reading frame encoding one of the vertebrate hh polypeptides of the present invention, including both exon and (optionally) intron sequences. A 'recombinant gene' refers to nucleic acid encoding a vertebrate hh polypeptide and comprising vertebrate hh-encoding exon sequences, though it may optionally include intron sequences which are either derived from a chromosomal vertebrate hh gene or from an unrelated chromosomal gene. The term 'intron' refers to a DNA sequence present in a given vertebrate hh gene which is not translated into protein and is generally found between exons.

The term 'transformation', as used herein, refers to a process in which a cell's genotype is changed as a result of the cellular uptake of exogenous DNA or RNA. For example, the transformed cell expresses a recombinant form of a vertebrate hh polypeptide or, where anti-sense expression occurs from the transferred gene, the expression of a naturally-occurring form of the vertebrate hh protein is disrupted.

As used herein, the term 'transfection' means the introduction of a nucleic acid, e.g., an expression vector, into a recipient cell by nucleic acid-mediated gene transfer.

As used herein, the term 'vector' refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as 'expression vectors'. In general, expression vectors of utility in recombinant DNA techniques are often in the form of 'plasmids' which refer generally to circular double stranded DNA loops which, in their vector form are not bound to the chromosome. In the present specification, 'plasmid' and 'vector' are used interchangeably as the plasmid is the most commonly used form of vector. However, the invention is intended to include such other forms of expression vectors which serve equivalent functions and which become known in the art subsequently hereto.

'Transcriptional regulatory sequence' is a generic term used to refer to DNA sequences, such as initiation signals, enhancers, and promoters, which induce or control transcription of protein coding sequences with which they are operably linked. In preferred embodiments, transcription of one of the recombinant vertebrate hedgehog genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of hedgehog proteins.

As used herein, the term 'tissue-specific promoter' means a DNA sequence that serves as a promoter, i.e., regulates expression of a selected DNA sequence operably linked to the promoter, and which effects expression of the selected DNA sequence in specific cells of a tissue, such as cells of neural origin, e.g. neuronal cells. The term also covers so-called 'leaky' promoters, which regulate expression of a selected DNA primarily in one tissue, but cause expression in other tissues as well.

'Cells,' 'host cells' or 'recombinant host cells' are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "internal epithelial tissue" refers to tissue inside the body which has characteristics similar to the epidermal layer in the skin. Examples include the lining of the intestine.

The term "vacuole" refers to a membrane bound vesicle of eukaryotic cells that are generally greater than 100 nm in diameter to which functions cannot be definitely ascribed. It may refer to lysosomes, endosomes, secretory vesicles, phagocytic organelles or other membrane bound organelles.

The term "lipid" refers to a heterogeneous class of organic compounds which are extractable from biological material by nonpolar solvents such as ether, chloroform, benzene etc., but not by aqeous solvents. Some lipids, like cholesterol, may be found complexed with protein to form lipoproteins.

The term "cholesterol" refers to sterols, which are essential neutral lipd constituents of most eukaryotic plasma membranes. Animals usually obtain cholesterol from their diet, but there is the capacity from endogenous production to supply most of the daily requirement.

As used herein, "proliferating" and "proliferation" refer to cells undergoing mitosis.

As used herein, "transformed cells" refers to cells that have spontaneously converted to a state of unrestrained growth, i.e., they have acquired the ability to grow through an indefinite number of divisions in culture. Transfected cells may be characterized by such terms as neoplastic, anaplastic and/or hyperplastic, with respect to their loss of growth control.

As used herein, the term "immortalized cells" refers to cells which have been altered via chemical and/or recombinant means such that the cells have the ability to grow through an indefinite number of divisions in culture.

A "patient" or "subject" to be treated by the subject method can mean either a human or non-human animal.

An "effective amount" of an antagonist or agonist of the invention with respect to the subject method of treatment, refers to an amount of either an agonist or antagonist in a preparation which, when applied as part of a desired dosage regimen, brings about a change in the rate of e.g. lipid metabolism, vacuole formation, fat accumulation and the like according to clinically acceptable standards for the disorder to be treated.

The "growth state" of a cell refers to the rate of proliferation of the cell and the state of differentiation of the cell.

III. General Properties of Hedgehog Proteins

Isolated hedgehog proteins are naturally occurring or recombinant proteins of the hedgehog family and may be obtainable from either invertebrate or vertebrate sources (see references below). Members of the vertebrate hedgehog protein family share homology with proteins encoded by the Drosophila hedgehog (hh) gene (Mohler and Vani, (1992) Development 115, 957–971). To date, the combined screening of mouse genomic and cDNA libraries has identified three mammalian hh counterparts referred to as Desert hedgehog (Dhh), Sonic hedgehog (Shh) and Indian hedgehog (Ihh), which also exist in other mammals such as humans as well as in fish and birds. Other members include Moonrat hedgehog (Mhh), as well as Tiggy-winkle hedgehog (TwHh) and echidna hedgehog (Ehh).

Hedgehog genes encode glycoproteins which undergo cleavage, yielding an N-terminal domain of about 20 kDa responsible for signaling and a carboxy terminal fragment of about 25 kDa. Various other fragments that encompass the 20 kDa moiety are considered within the definition of "isolated hedgehog protein". Publications disclosing these sequences, as well as their chemical and physical properties, include (Hall et al., (1995) Nature 378, 212–216; Ekker et al., (1995) Current Biology 5, 944–955; Fan et al., (1995) Cell 81, 457–465, Chang et al., (1994) Development 120, 3339–3353; Echelard et al., (1993) Cell 75, 1414–1430 34–38); PCT Patent Application WO 9523223 (Jessell, Dodd, Roelink and Edlund).

Hedgehog family members include any of the naturally-occurring native hedgehog proteins including allelic, phylogenetic counterparts or other variants thereof, whether naturally-sourced or chemically produced including muteins or mutant proteins, as well as recombinant forms and new, active members of the hedgehog family.

The vertebrate family of hedgehog genes includes at least four members, e.g., paralogs of the single drosophila hedgehog gene (reference). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Isolated hedgehog proteins used in the methods of this invention are naturally occurring or recombinant proteins of the hedgehog family and may be obtainable from either invertebrate or from vertebrate sources (see references below). Members of the vertebrate hedgehog protein family share homology with proteins encoded by the Drosophila hedgehog (hh) gene (Mohler and Vani, (1992) Development 115, 957–971). Other members continue to be identified.

Mouse and chicken Shh and mouse Ihh genes (see, for example, U.S. Pat. No. 5,789,543) encode glycoproteins which undergo cleavage, yielding an amino terminal fragment of about 20 kDa and a carboxy terminal fragment of about 25 kDa. The most preferred 20 kDa fragment has the consensus sequence SEQ ID NO:22. Various other fragments that encompass the 20 kDa moiety are considered within the presently claimed invention. Publications disclosing these sequences, as well as their chemical and physical properties, include Hall et al., (1995) Nature 378, 212–216; Ekker et al., (1995) Current Biology 5, 944–955; Fan et al., (1995) Cell 81, 457–465, Chang et al., (1994) Development 120, 3339–3353; Echelard et al., (1993) Cell 75, 1414–1430 34–38); PCT Patent Application WO 95/23223 (Jessell, Dodd, Roelink and Edlund; PCT Patent Publication WO 95/18856 (Ingham, McMahon and Tabin). U.S. Pat. No. 5,759,811 lists the Genbank accession numbers of a complete mRNA sequence encoding human Sonic hedgehog; a partial sequence of human Indian hedgehog mRNA, 5' end; and a partial sequence of human Desert hedgehog mRNA. The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The vertebrate family of hedgehog genes includes at least four members, e.g., paralogs of the single drosophila hedgehog gene (SEQ ID No.19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No.8; and a zebrafish Thh is encoded by SEQ ID No.9.

TABLE 1

Guide to hedgehog sequences in Sequence Listing

| | Nucleotide | Amino Acid |
| --- | --- | --- |
| Chicken Shh | SEQ ID No. 1 | SEQ ID No. 10 |
| Mouse Dhh | SEQ ID No. 2 | SEQ ID No. 11 |
| Mouse Jhh | SEQ ID No. 3 | SEQ ID No. 12 |

TABLE 1-continued

Guide to hedgehog sequences in Sequence Listing

| | Nucleotide | Amino Acid |
| --- | --- | --- |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to a proteolytic N-terminal portion of the mature protein.

In addition to the sequence variation between the various hedgehog homologs, the proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

Family members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family. Particularly useful hedgehog polypeptides have portions that include all or part of SEQ ID NOS:21–22.

Isolated hedgehog polypeptides used in the method of the invention have biological activity. The polypeptides include an amino acid sequence at least 60%, 80%, 90%, 95%, 98%, or 99% homologous to an amino acid sequence from SEQ ID NOS; 21–22. The polypeptide can also include an amino acid sequence essentially the same as an amino acid sequence in SEQ ID NOS:21–22. The polypeptide is at least 5, 10, 20, 50, 100, or 150 amino acids in length and includes at least 5, preferably at least 10, more preferably at least 20, most preferably at least 50, 100, or 150 contiguous amino acids from SEQ ID NOS: 21–22.

In one embodiment, isolated hedgehog is a hedgehog polypeptide with one or more of the following characteristics:

(i) it has at least 30, 40, 42, 50, 60, 70, 80, 90 or 95% sequence identity with amino acids of SEQ ID NOS:21–22;

(ii) it has a cysteine or a functional equivalent as the N-terminal end;

(iii) it may induce alkaline phosphatase activity in C3H10T1/2 cells;

(iv) it has an overall sequence identity of at least 50%, preferably at least 60%, more preferably at least 70, 80, 90, or 95%, with a polypeptide of SEQ ID NO; 21–22

(v) it can be isolated from natural sources such as mammalian cells;

(vi) it can bind or interact with patched; and (vii) it is modified at at least one amino acid residue by a polyalkylene glycol polymer attached to the residue or, optionally, via a linker molecule to the amino acid residue.

Preferred nucleic acids encode a polypeptide comprising an amino acid sequence at least 60% homologous or identical, more preferably 70% homologous or identical, and most preferably 80% homologous or identical with an amino acid sequence selected from the group consisting of SEQ ID Nos:21–22. Nucleic acids which encode polypeptides at least about 90%, more preferably at least about 95%, and most preferably at least about 98–99% homology or identity with an amino acid sequence represented in one of SEQ ID Nos:21–22 are also within the scope of the invention.

In another embodiment, the hedgehog protein is a polypeptide encodable by a nucleotide sequence that hybridizes under stringent conditions to a hedgehog coding sequence represented in one or more of SEQ ID NOS:1–9 or 19. Appropriate stringency conditions which promote DNA hybridization, for example, 6.0×sodium chloride/sodium citrate (SSC) at about 45 degrees C., followed by a wash of 2.0×SSC at 50 degrees C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50 degrees C. to a high stringency of about 0.2×SSC at 50 degrees C. In addition, the temperature in the wash step can be increased from low stringency conditions at room temperature, about 22 degrees C., to high stringency conditions at about 65 degrees C.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos:8–14. Nucleic acids which encode polypeptides at least about 90%, more preferably at least about 95%, and most preferably at least about 98–99% homology with an amino acid sequence represented in one of SEQ ID Nos:10–18 or 20 are also within the scope of the invention.

Hedgehog polypeptides preferred by the present invention, in addition to native hedgehog proteins, are at least 60% homologous, more preferably 70% homologous and most preferably 80% homologous with an amino acid sequence represented by any of SEQ ID Nos:10–18 or 20. Polypeptides which are at least 90%, more preferably at least 95%, and most preferably at least about 98–99% homologous with a sequence selected from the group consisting of SEQ ID Nos:10–18 or 20 are also within the scope of the invention.

With respect to fragments of hedgehog polypeptide, preferred hedgehogs moieties include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No.15, 28–202 of SEQ ID No.16, and 23–198 of SEQ ID No.17. By "corresponding approximately" it is meant that the sequence of interest is at most 20 amino acid residues different in length to the reference sequence, though more preferably at most 5, 10 or 15 amino acid different in length.

Still other preferred hedgehog polypeptides includes an amino acid sequence represented by the formula A-B wherein: (i) A represents all or the portion of the amino acid sequence designated by residues 1–168 of SEQ ID No:21; and B represents at least one amino acid residue of the amino acid sequence designated by residues 169–221 of SEQ ID No:21; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No:13; (iv) A represents all or the portion of the amino acid sequence designated by residues 23–193 of SEQ ID No:11; and B represents at least one amino acid residue of the amino acid sequence designated by residues 194–250 of SEQ ID No:11; (v) A represents all or the portion of the amino acid sequence designated by residues 28–197 of SEQ ID No:12; and B represents at least one amino acid residue of the amino acid sequence designated by residues 198–250 of SEQ ID No:12; (vi) A represents all or the portion of the amino acid sequence designated by residues 29–197 of SEQ ID No:16; and B represents at least one amino acid residue of the amino acid sequence designated by residues 198–250 of SEQ ID No:16; or (vii) A represents all or the portion of the amino acid sequence designated by residues 23–193 of SEQ ID No.17, and B represents at least one amino acid residue of the amino acid sequence designated by residues 194–250 of SEQ ID No.17. In certain preferred embodiments, A and B together represent a contiguous polypeptide sequence designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above.

A. Expression and Production of Hedgehog Polypeptides

It will be understood by persons having ordinary skill in the art that full length hedgehog polypeptides and both agonist and antagonist polypeptides described herein can be produced by any suitable method known in the art. Such methods range from direct protein synthetic methods to constructing a DNA sequence directly encoding hedgehog polypeptide sequences described above and expressing those hedgehog sequences in a suitable transformed host. Alternatively, hedgehog polypeptides of the invention may be developed by expressing full-length hedgehog proteins and then modifying them appropriately after expression to form the functional antagonist.

1. Direct Expression of Hedgehog Polypeptides.

Generally, to produce a hedgehog sequence (whether or not an agonist or antagonist) a complete hedgehog amino acid sequence may be used to construct a back-translated gene. See Maniatis et al., supra. Further, a DNA oligomer containing a nucleotide sequence coding for full length hedgehog may be synthesized. For example, several small oligonucleotides coding for portions of the desired hedgehog polypeptide may be synthesized and then ligated. The individual oligonucleotides typically contain 5' or 3' overhangs for complementary assembly. Hedgehog cDNA may be obtained by screening a human cDNA library with a labeled DNA fragment encoding the hedgehog polypeptides of SEQ ID NOS:1–8 and 11 and identifying positive clones by autoradiography. Further rounds of plaque purification and hybridization are performed using conventional methods.

If a DNA sequence is obtained encoding full length hedgehog polypeptide, the DNA may then be modified or mutagenized (see, e.g., Section C and D; Zoeller et al., (1984) Proc. Natl. Acad. Sci. USA, 81, 5662–66, and U.S. Pat. No. 4,588,585)) so as to express a hedgehog polypeptide, which may be an agonist or antagonist polypeptide. In recombinant methods, internal or terminal fragments of a hedgehog polypeptide can be generated by removing one or more nucleotides from one end (for a terminal fragment) or both ends (for an internal fragment) of a DNA sequence, which encodes for the isolated hedgehog polypeptide. Expression of the mutagenized DNA produces polypeptide fragments that are tested for biological activity. Digestion with "end nibbling" endonucleases can also generate DNAs which encode an array of fragments. DNA that encode fragments of a protein can also be generated by random shearing, restriction digestion or a combination or both.

Another method of constructing a similar DNA sequence would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced.

Therefore, isolated polynucleotides (e.g., RNA or DNA) acting as antagonists are used in the methods of the invention. Thus, the hedgehog polypeptides may encode hedgehog antagonists or hedgehog agonists that include a hedgehog polypeptide sequence in which the N-terminal cysteine is replaced by an N-terminal extension moiety. The isolated DNA sequence of the polypeptide can therefore encode, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog and that replaces the N-terminal cysteine of hedgehog; linked to (b) a second polypeptide that is a hedgehog protein, or a portion of hedgehog protein. Isolated polynucleotides of the invention also may encode for a hedgehog polypeptide that includes an N-terminal extension moiety that may contains the Cys-1 of a mature hedgehog polypeptide (e.g., Sonic hedgehog).

The isolated DNA sequence may encode, upon expression, a hedgehog polypeptide that contains the primary amino acid sequence comprising a hedgehog polypeptide lacking that N-terminal cysteine corresponding to Cys-1 of a mature hedgehog, such as, for instance, mature Sonic hedgehog. For example, the isolated DNA sequence or a portion thereof can encode a hedgehog polypeptide that has a deletion of no greater than about 12 amino acids beginning from that N-terminal cysteine corresponding to Cys-1 of mature Sonic hedgehog. Isolated hedgehog polypeptide used in the invention may also be generated that encode a antagonist or an agonist that has a mutation of the N-terminal cysteine to another amino acid residue. The isolated DNA sequence can also encode a antagonist or agonist that includes an N-terminal extension moiety.

Once assembled (by synthesis, site-directed mutagenesis or another method), the DNA sequences encoding a particular hedgehog polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR1, pBR322, pMB9 and their derivatives, wider host range plasmids, such as M13 and filamentous single-stranded DNA phages. Preferred *E. coli* vectors include pL vectors containing the lambda phage pL promoter (U.S. Pat. No. 4,874,702), pET vectors containing the T7 polymerase promoter (Studier et al., Methods in Enzymology 185: 60–89, 1990 1) and the pSP72 vector. Useful expression vectors for yeast cells, for example, include the centromere plasmids.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda (for example pL), the control regions of fd coat protein, the promoter for 3-phosphoglycerate kinase or other glycolytic enzymes, the promoters of acid phosphatase, e.g., Pho5, the promoters of the yeast alpha-mating system and other sequences known to control the expression of genes of prokaryotic or eukaryotic cells and their viruses, and various combinations thereof. Any suitable host may be used to produce in quantity the isolated hedgehog polypeptides described herein, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of *E. coli*, (Example 1), Pseudomonas, Bacillus, Streptomyces, fungi, yeast (e.g., Pichia; Example 3) insect cells such as *Spodoptera frugiperda* (SF9), and High Five™, animal cells such as Chinese hamster ovary (CHO), mouse cells such as NS/O cells, African green monkey cells COS1, COS7, BSC1, BSC40, and BMT10, and human cells, as well as plant cells.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation. For example, to produce isolated polypeptide of interest in large-scale animal culture, the copy number of the expression vector must be controlled. Amplifiable vectors are well known in the art. See, for example, Kaufman and Sharp, (1982) Mol. Cell. Biol., 2, 1304–1319 and U.S. Pat.

No. 4,470,461 and 5,122,464. Such operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) being located at the N-terminus of the product. This ensures that the hedgehog polypeptide, once expressed, maintains the core structure.

The proteins produced by a transformed host can be purified according to any suitable method. Such standard methods include chromatography (e.g., ion exchange, affinity and sizing column chromatography), centrifugation, differential solubility, or by any other standard technique for protein purification. For immunoaffinity chromatography, a protein such as Sonic hedgehog may be isolated by binding it to an affinity column comprising antibodies that were raised against Sonic hedgehog, or a related protein and were affixed to a stationary support. Alternatively, affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, mass spectrometry, nuclear magnetic resonance and x-ray crystallography.

2. Production of Hedgehog Polypeptide Fragments from Full-length Polypeptides.

Fragments of an isolated hedgehog protein having hedgehog antagonist or agonist activity are also produced efficiently using methods known to those of skill in the art. Functional hedgehog polypeptide can be generated from intact hedgehog proteins. Peptides can be specifically cleaved by proteolytic enzymes, including, but not limited to plasmin, thrombin, trypsin, chymotrypsin or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine and phenylalanine. Alternate sets of cleaved protein fragments are generated by preventing cleavage at a site which is susceptible to a proteolytic enzyme. For instance, reaction of the epsilon-amino acid groups of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with alpha-halo ethylamines yields peptide linkages that are hydrolyzed by trypsin (Lindley, (1956) Nature 178, 647). In addition, chemical reagents that cleave peptide chains at specific residues can be used. For example, cyanogen bromide cleaves peptides at methionine residues (Gross and Witkip, (1961) J. Am. Chem. Soc. 83, 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

3. Chemical Synthetic Methods.

Hedgehog polypeptides can also be chemically synthesized using techniques known in the art such as the Merrifield solid phase F moc or t-Boc chemistry. Merrifield, Recent Progress in Hormone Research 23: 451 (1967). Examples of prior art methods which allow production and testing of the agonists and antagonists are discussed below. These, or analogous methods may be used to make and screen fragments and analogs of an isolated polypeptide (e.g., hedgehog) which can be shown to have biological activity. Hedgehog polypeptides can also be created by a combination of chemical and recombinant methods to generate hedgehog chimeras.

B. Production of Other Hedgehog Polypeptide DNA and Peptide Sequences

1. Random Mutagenesis Methods.

Amino acid sequence variants of the functional hedgehog polypeptides can be prepared by random mutagenesis of DNA which encodes the protein or a particular portion thereof. Useful methods to induce mutations include PCR mutagenesis and saturation mutagenesis. The following examples of such methods are not intended to limit the scope of the present invention, but merely serve to illustrate representative techniques. Persons having ordinary skill in the art will recognize that other methods are also useful in this regard.

PCR Mutagenesis: See, for example Leung et al., (1989) Technique 1, 11–15.

Saturation Mutagenesis: One method is described generally in Mayers et al., (1989) Science 229, 242.

Degenerate Oligonucleotide Mutagenesis: See for example Harang, S. A., (1983) Tetrahedron 39, 3; Itakura et al., (1984) Ann. Rev. Biochem. 53, 323 and Itakura et al., Recombinant DNA, Proc. 3rd Cleveland Symposium on Macromolecules, pp. 273–289 (A. G. Walton, ed.), Elsevier, Amsterdam, 1981.

2. Directed Mutagenesis Methods.

Site-directed methods are another way in which an N-terminal cysteine (or a functional equivalent) can be effectively removed to produce the core structure of a functional hedgehog polypeptide. Non-random, or directed, mutagenesis provides specific sequences or mutations in specific portions of a polynucleotide sequence that encodes an isolated polypeptide, to provide variants which include deletions, insertions or substitutions of residues of the known amino acid sequence of the isolated polypeptide.

Alanine scanning Mutagenesis: See Cunningham and Wells, (1989) Science 244, 1081–1085).

Oligonucleotide-Mediated Mutagenesis: See, for example, Adelman et al., (1983) DNA 2, 183. We created a functional hedgehog polypeptide using oligonucleotide-directed mutagenesis by engineering an isolated DNA sequence that encodes a functional antagonist that has a mutation of the N-terminal cysteine to another amino residue, preferably a serine residue.

Cassette Mutagenesis: See Wells et al., (1985) Gene 34, 315.

Combinatorial Mutagenesis: See, for example, Ladner et al., WO 88/06630

One of ordinary skill in the art would appreciate that methods exist for generating sets of mutants of the subject hedgehog proteins, and these methods are especially useful for identifying potential variant sequences (e.g. homologs) that are either functional antagonists or agonists of the biological activity of hedgehog proteins. In this way, one screens combinatorial libraries containing such sets of antagonist and agonist mutants to generate, for example, novel hedgehog homologs which can act as either agonists or antagonists. Hedgehog homologs can be generated by this approach to act as antagonists, in that they are able to mimic, for example, binding to patched receptors, yet not induce any biological response, thereby inhibiting the action of authentic hedgehog or hedgehog agonists. Hedgehog homologs can be generated by this approach to act as agonists also, in that they are able to bind to the hedgehog receptor with at least the same, if not greater binding affinity that normal hedgehog.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-K-T-L-G-A-S-G-R-Y-E-G-K-I-X(3)-R-N-S-E-R-F-K-E-L-T-P-N-Y-N-P-D-I-I-F-K-D-E-E-N-T-G-A-D-R-L-M-T-Q-R-C-K-D-K-L-N-X(4)-L-A-I-S-V-M-N-X(5)-W-P-G-V-X(6)-L-R-V-T-E-G-W-D-E-D-G-H-H-X(7)-E-E-S-L-H-Y-E-G-R-A-V-D-I-T-T-S-D-R-D-X(8)-S-K-Y-G-X(9)-L-X(10)-R-L-A-V-E-A-G-F-D-W-V-Y-Y-E-S-K-A-H-I-H-C-S-V-K-A-E-N-S-V-A-A-K-S-G-G-C-F-P-G-S-A-X(11)-V-X(12)-L-X(13)-X(14)-G-G-X(15)-K-X-(16)-V-K-D-L-X(17)-P-G-D-X(18)-V-L-A-A-D-X(19)-X(20)-G-X(21)-L-X(22)-X(23)-S-D-F-X(24)-X(25)-F-X(26)-D-R (SEQ ID No: 21), wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gin; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gin, Asn, Glu, or Asp; Xaa(14) represents His, Phe, Tyr, Thr, Gin, Asn, Glu or Asp; Xaa(15) represents Gin, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gin, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gin; Xaa(21) represents Arg, Lys, Met, Ile, Asn, Asp, Glu or Gin; Xaa(22) represent Leu, Val, Met or Ile; Xaa(23) represents Phe, Tyr, Thr, His or Trp; Xaa(24) represents Ile, Val, Leu or Met; Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4)-X(5)-X(6)-P-K-X(7)-L-X(8)-P-L-X(9)-Y-K-Q-F-X(10)-P-X(11)-X(12)-X(13)-E-X(14)-T-L-G-A-S-G-X(15)-X(16)-E-G-X(17)-X(18)-X(19)-R-X(20)-S-E-R-F-X(21)-X(22)-L-T-P-N-Y-N-P-D-I-I-F-K-D-E-E-N-X(23)-G-A-D-R-L-M-T-X(24)-R-C-K-X(25)-X(26)-X(27)-N-X(28)-L-A-I-S-V-M-N-X(29)-W-P-G-V-X(30)-L-R-V-T-E-G-X(31)-D-E-D-G-H-H-X(32)-X(33)-X(34)-S-L-H-Y-E-G-R-A-X(35)-D-I-T-T-S-D-R-D-X(36)-X(37)-K-Y-G-X(38)-L-X(39)-R-L-A-V-E-A-G-F-D-W-V-Y-Y-E-S-X(40)-X(41)-H-X(42)-H-X(43)-S-V-K-X(44)-X(45) (SEQ ID No: 22), wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gin, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gin or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gin; Xaa(21) represents Arg, His or Lys; Xaa(22) represents Asp or Glu; Xaa(23) represents Ser or Thr; Xaa(24) represents Glu, Asp, Gin or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gin, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gin, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gin, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gin, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos.5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one aspect of this method, the amino acid sequences for a population of hedgehog polypeptides are aligned, preferably to promote the highest homology possible. Such a population of variants can include, for example, hedgehog antagonists from one or more species or hedgehog agonists. Amino acids, which appear at each position of the aligned hedgehog polypeptide sequences are selected to create a degenerate set of combinatorial sequences. There are many ways by which the library of potential hedgehog homologs described above can be generated. Various techniques are known in the art for screening generated mutant gene products.

Techniques for screening large gene libraries often include cloning the gene library into replicable expression vectors, transforming appropriate cells with the resulting library of vectors, and expressing the genes under conditions in which detection of a desired activity, e.g., in this case, agonist or antagonist activity, or to a downstream intracellular protein, facilitates relatively easy isolation of the vector encoding the gene whose product was detected. Such methods include two hybrid systems in which a hedgehog receptor is used as the "bait" protein and the library of variants of the hedgehog antagonist are expressed as "fish" proteins and various display libraries in which the candidate antagonists are displayed on the surface of a cell or viral particle, and the ability of particular cells or viral particles to bind an appropriate receptor protein via the displayed product is detected in a "panning assay". See, for example, Ladner et al., WO 88/06630; Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; Barbas et al. (1992) *PNAS* 89:4457–4461), Charbit et al. (1986) *EMBO* 5, 3029–3037), Schorr et al. (1991) *Vaccines* 91, pp. 387–392), Agterberg, et al. (1990) *Gene* 88, 37–45, Thiry et al. (1989) *Appl. Environ. Microbiol.* 55, 984–993); Kuwajima et al. (1988) *Bio/Tech.* 6, 1080–1083); Hansson et al. (1992) *J. Bacteriol.* 174, 4239–4245 and Klauser et al. (1990) *EMBO J.* 9, 1991–1999); Cull et al. (1992) *PNAS USA* 89:1865–1869.

C. Other Variants of Isolated Hedgehog Polypeptides

Included in the methods of the invention are the use of isolated molecules that are: allelic variants, natural mutants, induced mutants, proteins encoded by DNA that hybridize under high or low stringency conditions to a polynucleotide which encodes a hedgehog-related polypeptide such as the functional polypeptides of this invention. All variants described herein are expected to retain the antagonist biological function or full agonist biological function. Preferred analogs include biologically active hedgehog polypeptide fragments whose sequences differ from known hedgehog sequences herein by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Other conservative substitutions can be readily known by workers of ordinary skill. For example, for the amino acid alanine, a conservative substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions that may be expected to induce changes in the functional properties of isolated polypeptides are those in which: (i) a polar residue, e.g., serine or threonine, is substituted for (or by) a hydrophobic residue, e.g., leucine, isoleucine, phenylalanine, or alanine; (ii) a cysteine residue (i.e., the N-terminal cysteine and optionally one or more other internal cysteines) is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine.

D. Peptide Mimetics

The invention also provides for the use of mimetics, e.g. peptide or non-peptide hedgehog agents. The peptide mimetics are able to either agonize or antagonize the biological activity of hedgehog protein, for example by disrupting binding of hedgehog to a naturally occurring ligand, e.g., a receptor or by binding to the receptor with greater affinity than normal hedgehog. The critical residues of a subject polypeptide which are involved in molecular recognition of a receptor polypeptide or which are involved in its inability to promote hedgehog-dependent signaling, can be determined and used to generate peptidomimetics (see, for example, "Peptide inhibitors of human papillomavirus protein binding to retinoblastoma gene protein" European patent applications EP-412,762A and EP-B31,080A). For example, scanning mutagenesis can be used to map the amino acid residues of a particular polypeptide involved in its ability or inability to promote hedgehog-dependent signaling, peptidomimetic compounds (e.g. diazepine or isoquinoline derivatives) can be generated which mimic those residues and which therefore can interfere with the function of hedgehog.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647)); and Sato et al. (1986) J Chem Soc Perkin Trans 1:1231)), and beta-aminoalcohols (Gordon et al. (1985) Biochem Biophys Res Commun126:419); and Dann et al. (1986) Biochem Biophys Res Commun 134:71)).

E. Production of Hedgehog Polypeptides from Antibody Homologs

The technology for producing monoclonal antibody homologs is well known. Briefly, an immortal cell line (typically myeloma cells) is fused to lymphocytes (typically splenocytes) from a mammal immunized with whole cells expressing a given antigen, e.g., hedgehog, and the culture supernatants of the resulting hybridoma cells are screened for antibodies against the antigen. See, generally, Kohler et at., 1975, Nature 265: 295–497, "Continuous Cultures of Fused Cells Secreting Antibody of Predefined Specificity".

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-hedgehog antibodies may be identified by immunoprecipitation of 125I-labeled cell lysates from hedgehog-expressing cells. Anti-hedgehog antibodies may also be identified by flow cytometry, e.g., by measuring fluorescent staining of antibody-expressing cells incubated with an antibody believed to recognize hedgehog. The lymphocytes used in the production of hybridoma cells typically are isolated from immunized mammals whose sera have already tested positive for the presence of anti-hedgehog antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-hedgehog antibodies may be screened by testing the hybridoma culture supernatant for secreted antibodies having the ability to bind to a recombinant hedgehog-expressing cell line.

To produce anti-hedgehog antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-hedgehog antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several mouse anti-hedgehog monoclonal antibodies have been described in the prior art.

Fully human monoclonal antibody homologs against hedgehog or patched are another preferred binding agent which may block or coat hedgehog or patched antigens in the method of the invention. In their intact form these may be prepared using in vitro-primed human splenocytes, as described by Boerner et al., 1991, J. Immunol. 147:86–95, "Production of Antigen-specific Human Monoclonal Antibodies from In Vitro-Primed Human Splenocytes".

Alternatively, they may be prepared by repertoire cloning as described by Persson et al., 1991, Proc. Nat. Acad. Sci. USA 88: 2432–2436, "Generation of diverse high-affinity human monoclonal antibodies by repertoire cloning" and Huang and Stollar, 1991, J. Immunol. Methods 141: 227–236, "Construction of representative immunoglobulin variable region CDNA libraries from human peripheral blood lymphocytes without in vitro stimulation". U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells, which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Yet another preferred binding agent which may block or coat hedgehog or patched antigens in the method of the invention is a humanized recombinant antibody homolog having the capability of binding to a hedgehog or patched protein. Following the early methods for the preparation of chimeric antibodies, a new approach was described in EP 0239400 (Winter et al.) whereby antibodies are altered by substitution of their complementarily determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping". (Riechmann et al., 1988 Nature 332: 323–327, "Reshaping human antibodies for therapy"; Verhoeyen et al., 1988, Science 239: 1534–1536, "Reshaping of human antibodies using CDR-grafting in Monoclonal Antibodies".

Typically, complementarily determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986 Nature 321: 522–525, "Replacing the complementarity-determining regions in a human antibody with those from a mouse"; Riechmann, 1988, Nature 332:323–327, "Reshaping human antibodies for therapy"; Queen et al., 1989, Proc. Nat. Acad. Sci. USA 86:10029, "A humanized antibody that binds to the interleukin 2 receptor" and Orlandi et al., 1989, Proc. Natl. Acad. Sci. USA 86:3833 "Cloning Immunoglobulin variable domains for expression by the polymerase chain reaction".

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In a number of cases, it appears to be critical to alter residues in the framework regions of the acceptor antibody in order to obtain binding activity. (Queen et al., 1989, Proc. Nat. Acad. Sci. USA 86: 10029–10033, "A humanized antibody that binds to the interleukin 2 receptor") and WO 90/07861 (Protein Design Labs Inc.) have described the preparation of a humanized antibody that contains modified residues in the framework regions of the acceptor antibody by combining the CDRs of a murine mAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [supra]) and also for antibodies specific for herpes simplex virus (HSV) (Co. et al., 1991, Proc. Nat. Acad. Sci. USA 88: 2869–2873, "Humanised antibodies for antiviral therapy".

According to the above described two step approach in WO 90/07861, Queen et al. outlined several criteria for designing humanized immunoglobulins. The first criterion is to use as the human acceptor the framework from a particular human immunoglobulin that is usually homologous to the non-human donor immunoglobulin to be humanized, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRsS.

One may use a different approach (see Tempest, 1991, Biotechnology 9: 266–271, "Reshaping a human monoclonal antibody to inhibit human respiratory syncytial virus infection in vivo") and utilize, as standard, the V region frameworks derived from NEWM and REI heavy and light chains respectively for CDR-grafting without radical introduction of mouse residues. An advantage of using the Tempest et al., 1991 approach to construct NEWM and REI based humanized antibodies is that the 3dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody. Preferred hedgehog polypeptide useful in the present invention include chimeric recombinant and humanized recombinant antibody homologs (i.e., intact immunoglobulins and portions thereof) with hedgehog or patched specificity.

F. Testing for Functionality

While many bioassays have been used to demonstrate hedgehog activity, the C3H10T1/2 cell line provides a simple system for assessing hedgehog function without the complication of having to work with primary cell cultures or organ explants. The mouse embryonic fibroblast line C3H10T1/2 is a mesenchymal stem cell line that, under defined conditions, can differentiate into adipocytes, chondrocytes, and bone osteoblasts (Taylor, S. M., and Jones, P. A., Cell 17: 771–779 (1979) and Wang, E. A., et al., Growth Factors 9: 57–71 (1993). Bone morphogenic proteins drive the differentiation of C3H10T1/2 cells into the bone cell lineage and alkaline phosphatase induction has been used as a marker for this process (Wang et al., supra). Shh has a similar effect on C3H10T1/2 cells (Kinto, N. et al., FEBS Letts. 404: 319–323 (1997) and we routinely use the alkaline phosphatase induction by Shh as a quantitative measure of its in vitro potency. Shh treatment also produces a dose-dependent increase in gli-1 and ptc-1 expression, which can be readily detected by a PCR-based analysis.

IV. Functional Antagonists

The functional antagonists of the present invention are obtainable from isolated hedgehog proteins. Thus, Sonic, Indian or Desert may be converted into functional antagonists, as disclosed in U.S. patent application Ser. No. 60/106,703, and described briefly below. Other functional antagonists are anti-hedgehog or anti-patched-1 antibodies, as disclosed in U.S. patent application Ser. No. 60/078,935.

One of the most preferred polypeptides for use in the methods of the invention are antagonists of a biological activity of the naturally occurring or recombinant hedgehog protein (e.g., an isolated hedgehog such as a member of the vertebrate family obtainable from Sonic, Indian or Desert hedgehog protein described above). The functional antagonists have at least the following properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH3H10T1/2 cell-based AP induction assay. Antagonists of the invention may also have the additional properties of being (iii) unable to induce ptc-1 and gli-1 expression. Persons having ordinary skill in the art can easily test any putative hedgehog antagonist for these properties. In particular, the mouse embryonic fibroblast line C3H10T1/2 is a mesenchymal stem cell line that is hedgehog responsive. Hedgehog treatment of the cells causes an upregulation of gli-1 and patched-1 (known indicators of hedgehog dependent signaling) and also causes induction of alkaline phosphatase activity, an indicator that the cells have differentiated down the chondrocyte/bone osteoblast lineage. Several hedgehog variants are unable to elicit a hedgehog-dependent response on C3H10T1/2 cells, but they competed with mature hedgehog for function and therefore served as functional antagonists.

A. N-Modified Hedgehog Polypeptides as Antagonists

Certain hedgehog variants that contain N-terminal modifications can block hedgehog function because they lack the ability to elicit a hedgehog-dependent response but retain the ability to bind to hedgehog receptor, patched-1. The critical primary amino acid sequence that defines whether a hedgehog polypeptide (i.e., a Sonic, Indian or Desert hedgehog) is a functional hedgehog antagonist is the N-terminal cysteine residue which corresponds to Cys-1 of the mature hedgehog. So long as the hedgehog polypeptide either lacks this N-terminal cysteine completely or contains this N-terminal cysteine in a modified form (e.g. chemically modified or included as part of an N-terminal extension moiety), the resulting polypeptide can act as a functional hedgehog antagonist. In this regard, the fact that an N-terminal cysteine "corresponds to Cys-1" means: (a) the N-terminal cysteine is the Cys-1 of mature Sonic, Indian or Desert hedgehog; or (b) the N-terminal cysteine occupies the same position as Cys-1 of mature Sonic, Indian or Desert hedgehog. Provided that, for example, a Sonic hedgehog has an N-terminal cysteine corresponding to Cys-1 that is altered or otherwise modified as described herein, it can antagonize the action of any other member of the hedgehog family. Therefore, persons having ordinary skill in the art will understand that it is possible to an Indian hedgehog protein that antagonizes the activity of Sonic, Desert or Indian hedgehogs.

Examples of these antagonists with N-terminal modifications are included below and one skilled in the art can alter the disclosed structure of the antagonist, e.g., by producing fragments or analogs, and test the newly produced structures for antagonist activity. These examples in no way limit the structure of any related hedgehog antagonists, but are merely provided for further description. These, or analogous methods, can be used to make and screen fragments and analogs of a antagonist polypeptides. There are several variants that are able to function as antagonists.

1. N-terminal Extensions

Antagonist polypeptides of the invention may include a hedgehog polypeptide sequence in which the N-terminal cysteine is linked to an N-terminal extension moiety. The isolated antagonist polypeptide can therefore be, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog, linked to (b) an N-terminal cysteine corresponding to Cys-1 of Sonic hedgehog that is part of a hedgehog antagonist of the invention, or a portion of hedgehog antagonist. This N-terminal extension moiety (e.g., the first N-terminal polypeptide portion) can be a histidine tag, a maltose binding protein, glutathione-S-transferase, a DNA binding domain, or a polymerase activating domain. The functional antagonist may include an N-terminal extension moiety that contains an element which replaces the Cys-1 of mature hedgehog or an N-terminal cysteine that corresponds to Cys-1 of a mature Sonic hedgehog.

2. N-terminal Deletions

Another variation of a functional antagonist is a hedgehog protein that is missing no greater than about 12 amino acids beginning from that N-terminal cysteine corresponding to Cys-1 of a mature hedgehog. Deletions in more than the about the first 12 contiguous amino acid residues do not generate functional antagonists. Preferably, deletions of about 10 contiguous amino acids will provide suitable functional antagonists. One can, however, remove fewer than 10 contiguous residues and still maintain antagonist function. Moreover, one can delete various combinations of non-contiguous residues provided that there are at least about 3 deleted residues in total.

These structures highlight the importance of the N-terminus of hedgehog proteins for function. All of the variants were indistinguishable from mature Sonic hedgehog (Shh) in their ability to bind patched-1, but were inactive in the in vitro C3H10T1/2 AP induction assay. All these N-terminal variants are unable to promote hedgehog-dependent signaling.

3. N-terminal Mutations

Yet another functional antagonist has a mutation of the N-terminal cysteine to another amino acid residue. Any amino acid residue may acceptable and persons having ordinary skill in the art following the teachings described herein will be able to perform the mutations and test the effects of such mutations. One example is Shh in which the N-terminal cysteine is replaced with a serine residue. This mutated form is indistinguishable from mature Shh in its ability to bind patched-1, but it blocks AP induction by mature Shh when tested for function in the C3H10T1/2 AP induction assay.

4. N-terminal Cysteine Modifications

Because the primary amino acid sequence of hedgehog contains the Cys-1 that is important for biological activity, certain other modifications will result in inactive antagonist variants of hedgehog protein. Another antagonist is an isolated functional antagonist of a hedgehog polypeptide, comprising a hedgehog polypeptide containing an N-terminal cysteine that corresponds to Cys-1 of a mature Sonic hedgehog, except that the cysteine is in a modified form. Antagonist polypeptides of hedgehog may have non-sequence modifications that include in vivo or in vitro chemical derivatization of their N-terminal cysteine, as well as possible changes in acetylation, methylation, phosphorylation, amidation, carboxylation or glycosylation. As an example, the functional antagonist can have an N-terminal cysteine in an oxidized form. Thus, a functional antagonist can have an N-terminal cysteine that is effectively modified by including it as part of an N-terminal extension moiety.

B. Other Embodiments

The antagonist polypeptides of the invention can include amino acid sequences that are at least 60% homologous to a hedgehog protein. The antagonist must exhibit at least the following functional antagonist properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH3H10T1/2 cell-based AP induction assay.

Antagonists useful in the present invention also include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, isolated antagonist is a polypeptide with one or more of the following characteristics:

(i) it has at least 60, more preferably 90 and most preferably 95% sequence identity with amino acids of SEQ ID NO:21–22;

(ii) it either has a modified N-terminal cysteine or lacks an N-terminal cysteine or has an N-terminal cysteine in a position different from the N-terminal cysteine corresponding to Cys-1 of the hedgehog;

(iii) it blocks alkaline phosphatase induction by mature hedgehog in CH3H10T1/2 cells;

(iv) it binds or interacts with its receptor patched-1 with an affinity that may be less than, but is preferably at least the same as, the binding of mature hedgehog protein to patched-1;

(v) it is unable to induce ptc-1 and gli-1 expression in vitro in CH3H10T1/2 cells; or (vi) it is unable to induce AP in CH3H10T1/2 assays.

Moreover, isolated hedgehog antagonists useful in the present invention can also be a recombinant fusion protein containing additional C-terminal sequences unrelated to hedgehog. Thus, the antagonist polypeptide may also include all or a fragment of an amino acid sequence from SEQ ID NOS:21–22 fused, in reading frame, to additional amino acid residues. One version of the polypeptides of the invention is a protein having a first polypeptide portion and a hedgehog antagonist portion, the antagonist portion being fused or otherwise linked either 5' or 3' to the first polypeptide portion. Thus, first, additional polypeptide portion has an amino acid sequence unrelated to an antagonist polypeptide. The additional polypeptide portion can be, e.g., any of glutathione-S-transferase, a DNA binding domain, or a polymerase activating domain, a histidine tag, an immunoglobulin or portion thereof, fused or otherwise linked to either the N- or C-terminus of the antagonist portion.

Additional modified polypeptides include those that contain chemical moieties such as polyethylene glycol (PEG) and/or dextran, among others. The addition of such chemical moieties may be specific to the N-terminal cysteine or may involve linkages to other amino acid residues of the antagonist polypeptide. Moieties such as PEG or dextran, or constructs such as immunoglobulin fusions, may serve to increase the effective half-life of the antagonist proteins when they are used as therapeutics. Hedgehog proteins are conjugated most preferably via a terminal reactive group on the polyalkylene glycol polymer although conjugations can also be branched from non-terminal reactive groups. The polymer with the reactive group(s) is designated herein as "activated polymer". The reactive group would be expected to selectively react with free amino or other reactive groups on the hedgehog protein. In theory, the activated polymer(s) are reacted so that attachment could occur at any available hedgehog amino group such as alpha amino groups or the epsilon-amino groups of lysines, or —SH groups of cysteines. Free carboxylic groups, suitably activated carbonyl groups, hydroxyl, guanidyl, oxidized carbohydrate moieties and mercapto groups of the hedgehog protein (if available) can also be used as attachment sites.

In particular, the chemical modification of any N-terminal cysteine to protect the thiol, with concomitant conjugation with a polyalkylene glycol moiety (i.e., PEG), can be carried out in numerous ways by someone skilled in the art. See U.S. Pat. No. 4,179,337. The sulfhydryl moiety, with the thiolate ion as the active species, is the most reactive functional group in a protein. There are many reagents that react faster with the thiol than any other groups. See Chemistry of Protein Conjugation and Cross-Linking (S. S. Wong, CRC Press, Boca Raton, Fla., 1991). The thiol of an N-terminal cysteine, such as found in all hedgehog proteins, would be expected to be more reactive than internal cysteines within the sequence. This is because the close proximity to the alpha-amine will lower the pKa of the thiol resulting in a greater degree of proton dissociation to the reactive thiolate ion at neutral or acid pH. In addition, the cysteine at the N-terminus of the structure is more likely to be exposed than the other two cysteines in the hedgehog sequence that are found buried in the protein structure.

Other examples of methods that provide linkage between a polyalkylene glycol and the N-terminal cysteine would be reactions with other alpha-haloacetyl compounds, organomercurials, disulfide reagents, and other N-substituted maleimides. Numerous derivatives of these active species are available commercially (e.g., ethyl iodoacetate (Aldrich, Milwaukee Wis.), phenyl disulfide (Aldrich), and N-pyrenemaleimide (Molecular Probes, Eugene Oreg.)) or could be synthesized readily (e.g., N-alkyliodoacetamides, N-alkylmaleimides, and organomercurials).

Another aspect to the reactivity of an N-terminal cysteine is that it can take part in reaction chemistries unique to its 1,2-aminothiol configuration. One example is the reaction with thioester groups to form an N-terminal amide group via a rapid S to N shift of the thioester. This reaction chemistry can couple together synthetic peptides and can be used to add single or multiple, natural or unnatural, amino acids or other hydrophobic groups via the appropriately activated peptide. Another example, is the reaction with aldehydes to form the thiazolidine adduct. Numerous hydrophobic derivatives of thiol esters (e.g., C2–C24 saturated and unsaturated fatty acyl Coenzyme A esters (Sigma Chemical Co., St. Louis, Mo.)), aldehydes (e.g., butyraldehyde, n-decyl aldehyde, and n-myristyl aldehyde (Aldrich)), and ketones (e.g., 2-, 3-, and 4-decanone (Aldrich)) are available commercially or could be synthesized readily. In a similar manner, thiomorpholine could be prepared from a variety of alpha-haloketone starting materials.

B. Attachment of a Polymer Moiety to the C-terminus of Hedgehog

Notwithstanding the fact that the chemistry needed to attach a polyalkylene glycol moiety to the N-terminal cysteine or the lysines of hedgehog protein is readily available, it is not necessarily correct to assume that, once a particular "PEG" linkage chemistry is available for a particular amino acid, the attachment of the polymer moiety to that particular amino acid will have the intended effect.

Indeed, although the polymer may be attached anywhere on the hedgehog molecule that is not already modified by, for example, a hydrophobic group, the most preferred site for polymer coupling is at a site other than the N-terminus of the hedgehog and other than the lysine(s). The most preferred sites are site(s) at or near the C-terminus. Several observations suggest that the C-terminus or amino acids near the C-terminus would be preferred targets for modification with a polyalkylene glycol moiety: (i) The wild-type protein is naturally modified with cholesterol at this site, indicating that it is exposed and available for modification. Indeed, we showed that treatment with thrombin results in selective release of the C-terminal 3 amino acids (See U.S. Ser. No. 60/106,703, filed Nov. 2, 1998); (ii) We performed extensive SAR analyses and discovered that the C-terminal 11 amino acids could be deleted without harmful effects on folding or function; (iii) We have made hedgehog/Ig fusion proteins by attaching an Ig moiety to the C-terminus of hedgehog without harmful effects on folding or function (data not presented here).

While there is no simple chemical strategy for targeting a polyalkylene glycol polymer such as PEG to the C-terminus of hedgehog, it is straightforward to genetically engineer a site that can be used to target the polymer moiety, as discussed above with regard to site-directed mutagenesis. For example, incorporation of a Cys at a site that is at or near the C-terminus allows specific modification using a maleimide, vinylsulfone or haloacetate-activated polyalkylene glycol (e.g., PEG). As discussed above in Section A, these derivatives can be used specifically for modification of the engineered C-terminal cysteines due to the high selectively of these reagents for Cys. Other strategies such as incorporation of a histidine tag which can be targeted (Fancy et al., (1996) Chem. & Biol. 3: 551) or an additional glycosylation site, represent other alternatives for modifying the C-terminus of hedgehog.

Within the broad scope of the present invention, a single polymer molecule may be employed for conjugation with the hedgehog protein and modified versions thereof as discussed above, although it is also contemplated that more than one polymer molecule can be attached as well. Conjugated hedgehog compositions of the invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive or cross-linkable in character, to enhance various properties or characterisics of the overall conjugated material. Accordingly, the polymer may contain any functionality, repeating groups, linkages, or other constitutent structures which do not preclude the efficacy of the conjugated hedgehog composition for its intended purpose. Other objectives and advantages of the present invention will be more fully apparent from the ensuing disclosure and appended claims.

Illustrative polymers that may usefully be employed to achieve these desirable characteristics are described herein below in exemplary reaction schemes. In covalently bonded peptide applications, the polymer may be functionalized and then coupled to free amino acid(s) of the peptide(s) to form labile bonds.

Generally from about 1.0 to about 10 moles of activated polymer per mole of protein is employed, depending on the particular reaction chemistry and the protein concentration. The final amount is a balance between maximizing the extent of the reaction while minimizing non-specific modifications of the product and, at the same time, defining chemistries that will maintain optimum activity, while at the same time optimizing, if possible, the half-life of the protein. Preferably, at least about 50% of the biological activity of the protein is retained, and most preferably 100% is retained.

The reactions may take place by any suitable method used for reacting biologically active materials with inert polymers. Generally the process involves preparing an activated polymer (that may have at least one terminal hydroxyl group) and thereafter reacting the protein with the activated polymer to produce the soluble protein suitable for formulation. The above modification reaction can be performed by several methods, which may involve one or more steps.

Suitable methods of attaching a polyalkylene glycol moiety to a C-terminal cysteine involve using such moieties that are activated with a thiol reactive group, as generally discussed above. Common thiol reactive groups include maleimides, vinylsulfones or haloacetates. These derivatives can be used specifically for modification of cysteines due to the high selectively of these reagents for —SH. Maleimides react specifically with free sulfhydryls (cysteine residues) in minutes, under slightly acidic to neutral (pH 6.0–7.5) conditions. This pH range is preferred although the reaction will proceed, albeit slowly, at pH 5.0. Halogens (iodoacetyl functions) react with —SH groups at physiological pH's to slightly basic conditions. Both of these reactive groups result in the formation of stable thioether bonds.

In the practice of the present invention, polyalkylene glycol residues of C1–C4 alkyl polyalkylene glycols, preferably polyethylene glycol (PEG), or poly(oxy)alkylene glycol residues of such glycols are advantageously incorporated in the polymer systems of interest. Thus, the polymer to which the protein is attached can be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained. Examples of polyoxyethylated polyols include, for example, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

As an alternative to polyalkylene oxides, dextran, polyvinyl pyrrolidones, polyacrylamides, polyvinyl alcohols, carbohydrate-based polymers and the like may be used. Moreover, heteropolymers (i.e., polymers consisting of more than one species of monomer such as a copolymer) as described in U.S. Pat. No. 5,359,030 may be used (e.g., proteins conjugated to polymers comprising a polyalkylene glycol moiety and one or more fatty acids) Those of ordinary skill in the art will recognize that the foregoing list is merely illustrative and that all polymer materials having the qualities described herein are contemplated.

The polymer need not have any particular molecular weight, but it is preferred that the molecular weight be between about 300 and 100,000, more preferably between 10,000 and 40,000. In particular, sizes of 20,000 or more are best at preventing protein loss due to filtration in the kidneys.

Polyalkylene glycol derivatization has a number of advantageous properties in the formulation of polymer-hedgehog conjugates in the practice of the present invention, as associated with the following properties of polyalkylene glycol derivatives: improvement of aqueous solubility, while at the same time eliciting no antigenic or immunogenic response; high degrees of biocompatibility; absence of in vivo biodegradation of the polyalkylene glycol derivatives; and ease of excretion by living organisms.

Moreover, in another aspect of the invention, one can utilize hedgehog covalently bonded to the polymer component in which the nature of the conjugation involves cleavable covalent chemical bonds. This allows for control in terms of the time course over which the polymer may be cleaved from the hedgehog. This covalent bond between the hedgehog protein drug and the polymer may be cleaved by chemical or enzymatic reaction. The polymer-hedgehog protein product retains an acceptable amount of activity. Concurrently, portions of polyethylene glycol are present in the conjugating polymer to endow the polymer-hedgehog protein conjugate with high aqueous solubility and prolonged blood circulation capability. As a result of these improved characteristics the invention contemplates parenteral, aerosol, and oral delivery of both the active polymer-hedgehog protein species and, following hydrolytic cleavage, bioavailability of the hedgehog protein per se, in in vivo applications.

It is to be understood that the reaction schemes described herein are provided for the purposes of illustration only and are not to be limiting with respect to the reactions and structures which may be utilized in the modification of the hedgehog protein, e.g., to achieve solubility, stabilization, and cell membrane affinity for parenteral and oral administration. Generally speaking, the concentrations of reagents used are not critical to carrying out the procedures provided hererin except that the molar amount of activated polymer should be at least equal to, and preferably in excess of, the molar amount of the reactive group (e.g., thiol) on the hedgehog amino acid(s). The reaction of the polymer with the hedgehog to obtain the most preferred conjugated products is readily carried out using a wide variety of reaction schemes. The activity and stability of the hedgehog protein conjugates can be varied in several ways, by using a polymer of different molecular size. Solubilities of the conjugates can be varied by changing the proportion and size of the polyethylene glycol fragment incorporated in the polymer composition.

V. Agonists

One of the most preferred polypeptides for use in the methods of the invention are agonists of a biological activity of the naturally occurring or recombinant hedgehog. The agonists have at least one of the following properties: (i) the isolated protein binds the receptor patched-1 with an affinity that is at least the same as, but is preferably higher than, the binding of mature hedgehog protein to patched-1; or (ii) the isolated protein binds to a hedgehog protein in such a way as to increase the proteins binding affinity to patched-1 when tested in an in vitro CH3H10T1/2 cell-based AP induction assay. Agonists of the invention may also have the additional properties of being (iii) able to solely induce ptc-1 and gli-1 expression.

Human Sonic hedgehog, expressed as a full-length construct in either insect or in mammalian cells, has a hydrophobic palmitoyl group appended to the α-amine of the N-terminal cysteine (Pepinsky et al. in press). This is the first example of an extracellular signaling protein being modified in such a manner, and, in contrast to thiol-linked palmitic acid modifications whose attachment is readily reversible, this novel N-linked palmitoyl moiety is likely to be very stable by analogy with myristic acid modification.

As a direct consequence of this initial discovery, it is known that increasing the hydrophobic nature of a hedgehog signaling protein can increase the protein's biological activity. Thus, the modified hedgehog acts as its own antagonist. In particular, appending a hydrophobic moiety to a signaling protein, such as a hedgehog protein, can enhance the protein's activity, and thus, act as an agonist. The N-terminal cysteine of biologically active proteins not only provides a convenient site for appending a hydrophobic moiety, and thereby modifying the physico-chemical properties of the protein, but modifications to the N-terminal cysteine can also increase the protein's stability. Additionally, addition of a hydrophobic moiety to an internal amino acid residue on the surface of the protein structure enhances the protein's activity.

In addition to those effects seen by cholesterol-addition to the C-terminus of extracellular fragments of the protein, at least certain of the biological activities of the hedgehog gene products are unexpectedly potentiated by derivatization of the protein with lipophilic moieties at other sites on the protein and/or by moieties other than cholesterol. Certain aspects of the invention are directed to therapeutic preparations of hedgehog agonists which are modified at sites other than N-terminal or C-terminal residues of the natural processed form of the protein, and/or which are modified at such terminal residues with lipophilic moieties other than a sterol at the C-terminus or fatty acid at the N-terminus. Accordingly, the methods and compositions of the present invention include the use of the derivatized hedgehog polypeptides for all such uses as hedgehog agonists due to their increased biological activity and higher patched-1 binding affinity. Moreover, the subject methods can be performed on cells which are provided in culture (in vitro), or on cells in a whole animal (in vivo).

In one aspect, the present invention provides pharmaceutical preparations comprising, as an active ingredient, a hedgehog polypeptide being derivatized by one or more lipophilic moieties such as described herein. The subject hedgehog treatments are effective on both human and animal subjects. Animal subjects to which the invention is applicable extend to both domestic animals and livestock, raised either as pets or for commercial purposes. Examples are dogs, cats, cattle, horses, sheep, hogs and goats.

A. General Properties of Isolated Hedgehog Proteins Acting as Agonists

The polypeptide portion of the hedgehog compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

Family members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family. Particularly useful hedgehog polypeptides include those disclosed in U.S. patent application Ser. No. 60/106,703.

The preferred agonists for use in any of the methods of the present invention include a derivitized hedgehog polypeptide sequence as well as other N-terminal and/or C-terminal amino acid sequence or it may include all or a fragment of a hedgehog amino acid sequence. The isolated hedgehog polypeptide can also be a recombinant fusion protein having a first hedgehog portion and a second polypeptide portion, e.g., a second polypeptide portion having an amino acid sequence unrelated to hedgehog. The second polypeptide portion can be, e.g., histidine tag, maltose binding protein, glutathione-S-transferase, a DNA binding domain, or a polymerase-activating domain.

Polypeptides of the invention include those that arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, the agonist is a hedgehog polypeptide with one or more of the following characteristics:

(i) it has at least 30, 40, 42, 50, 60, 70, 80, 90 or 95% sequence identity with a hedgehog sequence such as SEQ ID NOS.21–22 or fragments thereof;

(ii) it has a cysteine or a functional equivalent as the N-terminal end;

(iii) it may induce alkaline phosphatase activity in C3H10T1/2 cells;

(iv) it has an overall sequence identity of at least 50%, preferably at least 60%, more preferably at least 70, 80, 90, or 95%, with a polypeptide of a hedgehog sequence;

(v) it can be isolated from natural sources such as mammalian cells;

(vi) it can bind or interact with patched; and (vii) it is hydrophobically-modified (i.e., it has at least one hydrophobic moiety attached to the polypeptide).

Increasing the overall hydrophobic nature of a hedgehog protein increases the biological activity of the protein. The potency of a signaling protein such as hedgehog can be increased by: (a) chemically modifying, such as by adding a hydrophobic moiety to, the sulfhydryl and/or to the α-amine of the N-terminal cysteine; (b) replacing the N-terminal cysteine with a hydrophobic amino acid; or (c) replacing the N-terminal cysteine with a different amino acid and then chemically modifying the substituted residue so as to add a hydrophobic moiety at the site of the substitution.

Additionally, modification of a hedgehog protein at an internal residue on the surface of the protein with a hydrophobic moiety by: (a) replacing the internal residue with a hydrophobic amino acid; or (b) replacing the internal residue with a different amino acid and then chemically modifying the substituted residue so as to add a hydrophobic moiety at the site of the substitution will retain or enhance the biological activity of the protein.

Additionally, modification of a protein such as a hedgehog protein at the C-terminus with a hydrophobic moiety by: (a) replacing the C-terminal residue with a hydrophobic amino acid; or (b) replacing the C-terminal residue with a different amino acid and then chemically modifying the substituted residue so as to add a hydrophobic moiety at the site of the substitution, will retain or enhance the biological activity of the protein.

There are a wide range of lipophilic moieties with which hedgehog polypeptides can be derivatived. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1–C18)- alkyl phosphate diesters, —O—CH2—CH(OH)—O—(C12-C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthylamine, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc.

Other exemplary lipophilic moietites include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbomaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(−)-myrtentaneacetyl, 2-norbornaneacetyl, anti-3-oxo-tricyclo [2.2.1.0<2,6>]-heptane-7-carbonyl, decanoyl, dodecanoyl, dodecenoyl, tetradecadienoyl, decynoyl or dodecynoyl.

If an appropriate amino acid is not available at a specific position, site-directed mutagenesis can be used to place a reactive amino acid at that site. Reactive amino acids include cysteine, lysine, histidine, aspartic acid, glutamic acid, serine, threonine, tyrosine, arginine, methionine, and tryptophan. Mutagenesis could be used to place the reactive amino acid at the N- or C-terminus or at an internal position.

For example, it is possible to chemically modify an N-terminal cysteine of a biologically active protein, such as a hedgehog protein, or eliminate the N-terminal cysteine altogether and still retain the protein's biological activity, provided that the modified or substituted chemical moiety is hydrophobic. It has been discovered that enhancement of hedgehog's biological activity roughly correlates with the hydrophobicity of the modification. In addition to enhancing the protein's activity, modifying or replacing the N-terminal cysteine eliminates unwanted cross reactions and/or modifications of the cysteine that can occur during production, purification, formulation, and storage of the protein. The thiol of an N-terminal cysteine is very reactive due to its proximity to the α-amine which lowers the pKa of the cysteine and increases proton dissociation and formation of the reactive thiolate ion at neutral or acid pH.

The replacement of the N-terminal cysteine of hedgehog with a hydrophobic amino acid results in a protein with increased potency in a cell-based signaling assay. By replacing the cysteine, this approach eliminates the problem of suppressing other unwanted modifications of the cysteine that can occur during the production, purification, formulation, and storage of the protein. The generality of this approach is supported by the finding that three different hydrophobic amino acids, phenylalanine, isoleucine, and methionine, each give a more active form of hedgehog, and thus, an agonist. Therefore, replacement of the cysteine with any other hydrophobic amino acid should result in an active protein. Furthermore, since we have found a correlation between the hydrophobicity of an amino acid or chemical modification and the potency of the corresponding modified protein in the C3H10T1/2 assay (e.g. Phe>Met, long chain length fatty acids>short chain length), it could be envisioned that adding more than one hydrophobic amino acid to the hedgehog sequence would increase the potency of the agonist beyond that achieved with a single amino acid addition. Indeed, addition of two consecutive isoleucine residues to the N-terminus of human Sonic hedgehog results in an increase in potency in the C3H10T1/2 assay as compared to the mutant with only a single isoleucine added. Thus, adding hydrophobic amino acids at the N- or C-terminus of a hedgehog protein, in a surface loop, or some combination of positions would be expected to give a more active form of the protein. The substituted amino acid need not be one of the 20 common amino acids. Methods have been reported for substituting unnatural amino acids at specific sites in proteins and this would be advantageous if the amino acid was more hydrophobic in character, resistant to proteolytic attack, or could be used to further direct the hedgehog protein to a particular site in vivo that would make its activity more potent or specific. Unnatural amino acids can be incorporated at specific sites in proteins during in vitro translation, and progress is being reported in creating in vivo systems that will allow larger scale production of such modified proteins.

There are many modifications of the N-terminal cysteine which protect the thiol and append a hydrophobic moiety. These modifications are discussed in more detail below. One of skill in the art is capable of determining which modification is most appropriate for a particular therapeutic use. Factors affecting such a determination include cost and ease of production, purification and formulation, solubility, stability, potency, pharmacodynamics and kinetics, safety, immunogenicity, and tissue targeting.

B. Chemical Modifications of Primary Amino Acid Sequence

The chemical modification of the N-terminal cysteine to protect the thiol, with concomitant activation by a hydrophobic moiety, can be carried out in numerous ways by someone skilled in the art. The sulfhydryl moiety, with the thiolate ion as the active species, is the most reactive functional group in a protein. There are many reagents that react faster with the thiol than any other groups. See Chemistry of Protein Conjugation and Cross-Linking (S. S. Wong, CRC Press, Boca Raton, Fla., 1991). The thiol of an N-terminal cysteine, such as found in all hedgehog proteins, would be expected to be more reactive than internal cysteines within the sequence. This is because the close proximity to the α-amine will lower the pKa of the thiol resulting in a greater degree of proton dissociation to the reactive thiolate ion at neutral or acid pH. In addition, the cysteine at the N-terminus of the structure is more likely to be exposed than the other two cysteines in the hedgehog sequence that are found buried in the protein structure. Other examples of such methods would be reaction with other α-haloacetyl compounds, organomercurials, disulfide reagents, and other N-substituted maleimides. Numerous hydrophobic derivatives of these active species are available commercially (e.g., ethyl iodoacetate (Aldrich, Milwaukee Wis.), phenyl disulfide (Aldrich), and N-pyrenemaleimide (Molecular Probes, Eugene Oreg.)) or could be synthesized readily (e.g., N-alkyliodoacetamides (84), N-alkylmaleimides, and organomercurials. The N-terminal cysteine of human Sonic hedgehog can be modified with N-isopropyliodoacetamide. The hydrophobically-modified protein is 2-fold more potent in the C3H10T1/2 assay than the unmodified protein. It is expected that modification of Shh with a long-chain alkyl iodoacetamide derivative will result in a modified protein with even greater enhancement of potency. Thus, such an agonist would have a greater binding affinity. Such N-alkyliodoacetamides can be synthesized readily by ones skilled in the art, using commercially available starting materials.

Another aspect to the reactivity of an N-terminal cysteine is that it can take part in reaction chemistries unique to its 1,2-aminothiol configuration. One example is the reaction with thioester groups to form an N-terminal amide group via a rapid S to N shift of the thioester. This reaction chemistry can couple together synthetic peptides and can be used to add single or multiple, natural or unnatural, amino acids or other hydrophobic groups via the appropriately activated peptide. Another example, demonstrated herein, is the reaction with aldehydes to form the thiazolidine adduct. Numerous hydrophobic derivatives of thiol esters (e.g., C2–C24 saturated and unsaturated fatty acyl Coenzyme A esters (Sigma Chemical Co., St. Louis Mo.)), aldehydes (e.g., butyraldehyde, n-decyl aldehyde, and n-myristyl aldehyde (Aldrich)), and ketones (e.g., 2-, 3-, and 4-decanone (Aldrich)) are available commercially or could be synthesized readily. In a similar manner, thiomorpholine could be prepared from a variety of ao-haloketone starting materials. Because of the ease of finding alternative routes to modifying the thiol of the N-terminal cysteine, or any cysteine in a protein, we do not wish to be bound by the specific examples demonstrated here.

The α-amine of a protein can be modified preferentially relative to other amines in a protein because its lower pKa results in higher amounts of the reactive unprotonated form at neutral or acidic pH. Modification of the N-terminal amine with a long chain fatty amide group, while maintaining a free cysteine thiol group, activates the hedgehog protein by as much as two orders of magnitude. Therefore chemistries that can be directed to react preferentially with the N-terminal amine would be expected to be of use in increasing the potency of the hedgehog proteins. Aryl halides, aldehydes and ketones, acid anhydrides, isocyanates, isothiocyanates, imidoesters, acid halides, N-hydroxysuccinimidyl (e.g., sulfo-NHS-acetate), nitrophenyl esters, acylimidazoles, and other activated esters are among those known to react with amine functions.

By replacing the N-terminal cysteine of hedgehog with certain other amino acids, other chemical methods can be used to add a hydrophobic moiety to the N-terminus. One example is to place a serine or threonine at the N-terminus, oxidize this amino acid to form an aldehyde, and then conjugate the protein with a chemical moiety containing a 1,2 aminothiol structure (e.g., a cysteine). A second example would be to place a histidine at the N-terminus to couple to a C-terminal thiocarboxylic acid.

C. Chemical Modification of Other Amino Acids.

There are specific chemical methods for the modification of many other amino acids. Therefore another route for synthesizing a more active form of hedgehog would be to chemically attach a hydrophobic moiety to an amino acid in hedgehog other than to the N-terminal cysteine. If an appropriate amino acid is not available at the desired position, site-directed mutagenesis could be used to place the reactive amino acid at that site in the hedgehog structure, whether at the N- or C-terminus or at another position. Reactive amino acids would include cysteine, lysine, histidine, aspartic acid, glutamic acid, serine, threonine, tyrosine, arginine, methionine, and tryptophan. Thus the goal of creating a better hedgehog agonist could be attained by many chemical means and we do not wish to be restricted by a particular chemistry or site of modification since our results support the generality of this approach.

The hedgehog polypeptide can be linked to the hydrophobic moiety in a number of ways including by chemical coupling means, or by genetic engineering. To illustrate, there are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl(4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) Bioconjugate Chemistry 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms. Preparing protein-protein conjugates using heterobifunctional reagents is disclosed in U.S. patent application Ser. No. 60/067,423.

For lipid-modified hedgehog obtained by chemically modifying the soluble, unmodified protein, palmitic acid and other lipids can be added to soluble Shh to create a lipid-modified forms with increased potency in the C3H10T1/2 assay. Another form of protein encompassed by the invention is a protein derivatized with a variety of lipid moieties. The principal classes of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: CH3(CH2)nCOOH. Table 1 below lists examples of some fatty acids that can be derivatized conveniently using conventional chemical methods.

Other lipids that can be attached to the protein include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups. Lipid-modified hedgehog proteins can be purified from either a natural source, or can be obtained by chemically modifying the soluble, unmodified protein.

TABLE 1

Exemplary Saturated and Unsaturated Fatty Acids

| Value of n | Common Name |
|---|---|
| Saturated Acids: CH3(CH2)nCOOH | |
| 2 | butyric acid |
| 4 | caproic acid |
| 6 | caprylic acid |
| 8 | capric acid |
| 10 | lauric acid |
| 12 | myristic acid* |
| 14 | palmitic acid* |
| 16 | stearic acid* |
| 18 | arachidic acid* |
| 20 | behenic acid |
| 22 | lignoceric acid |
| Unsaturated Acids | |
| CH3CH=CHCOOH | crotonic acid |
| CH3(CH2)3CH=CH(CH2)7COOH | myristoleic acid* |
| CH3(CH2)5CH=CH(CH2)7COOH | palmitoleic acid* |
| CH3(CH2)7CH=CH(CH2)7COOH | oleic acid* |
| CH3(CH2)3(CH2CH=CH)2(CH2)7COOH | linoleic acid |
| CH3(CH2CH=CH)3(CH2)7COOH | linolenic acid |
| CH3(CH2)3(CH2CH=CH)4(CH2)3COOH | arachidonic acid |

The asterisk (*) denotes the fatty acids that we found in recombinant hedgehog protein secreted from a soluble construct.

For protein purified from a natural source, we showed that when full-length human Sonic hedgehog (Shh) was expressed in insect cells and membrane-bound Shh purified from the detergent-treated cells using a combination of SP-Sepharose chromatography and immunoaffinity chromatography, that the purified protein migrated on reducing SDS-PAGE gels as a single sharp band with an apparent mass of 20 kDa. The soluble and membrane-bound Shh proteins were readily distinguishable by reverse phase HPLC, where the tethered forms eluted later in the acetonitrile gradient. We then demonstrated that human Sonic hedgehog is tethered to cell membranes in two forms, one form that contains a cholesterol, and therefore is analogous to the data reported previously for Drosophila hedgehog, and a second novel form that contains both a cholesterol and a palmitic acid modification. Soluble and tethered forms of Shh were analyzed by electrospray mass spectrometry using a triple quadrupole mass spectrometer, equipped with an electrospray ion source as well as by liquid chromatography-mass spectrometry. The identity of the N-terminal peptide from endoproteinase Lys-C digested tethered Shh was confirmed by MALDI PSD mass spectrometric measurement on a MALDI time of flight mass spectrometer. The site of palmitoylation was identified through a combination of peptide mapping and sequence analysis and is at the N-terminus of the protein. Both tethered forms were equally as active in the C3H10T1/2 alkaline phosphatase assay, but interestingly both were about 30-times more potent than soluble human Shh lacking the tether(s). The lipid modifications did not significantly affect the apparent binding affinity of Shh for its receptor, patched.

For lipid-modified hedgehog obtained by chemically modifying the soluble, unmodified protein, palmitic acid and other lipids can be added to soluble Shh to create a lipid-modified forms with increased potency in the C3H10T1/2 assay. Generally, therefore, the reactive lipid moiety can be in the form of thioesters of saturated or unsaturated carboxylic acids such as a Coenzyme A thioesters. Such materials and their derivatives may include, for example, commercially available Coenzyme A derivatives such as palmitoleoyl Coenzyme A, arachidoyl Coenzyme A, arachidonoyl Coenzyme A, lauroyl Coenzyme A and the like. These materials are readily available from Sigma Chemical Company (St. Louis, Mo., 1998 catalog pp. 303–306).

VI. Uses

A. General

Generally, the lipid modulators described herein are hedgehog agonist and antagonist proteins useful in therapeutic, diagnostic and research contexts. As indicated by the present invention, the hedgehog signaling pathway has been implicated in the metabolism of lipids within the gastrointestinal tract. In fact, the introduction into embryonic mice of antibodies directed against the hedgehog protein caused these mice to express the symptoms most common among subjects suffering from a variety of lipid metabolism disorders. These mice exhibited runting, severe diarrhea, general failure to thrive, accumulation of lipids in the gut epithelial tissue and early death (as exemplified in Example 1 below), all of which are symptoms shared by various animal models for aberrant expression of apolipoprotein B (McCormick et al. 1995 271:11963–11970) and by subjects afflicted with Anderson's disease, chlyomicron-retention disease, abetalipoproteinemia, hypobetalipoproteinemia, normotriglyceridemia, apo-B-100 deficiency and abetalipoproteinemia.

The methods of the present invention use lipid modulators to either agonize or antagonize the normal biological activity of the hedgehog proteins and the related signaling pathway. Thus, resulting in modulation of lipid metabolism and/or storage within intestinal epithelial tissue. The epithelial tissue can either be modulated in vivo or in ex vivo tissue cultures. Methods using lipid modulators such as hedgehog antagonists or agonists would be valuable to alter intestinal metabolism and storage of lipids in a subject suffering from weight loss or obesity.

In one example, lipid modulators such as hedgehog agonists or antagonists can be administered to further investigate the role of hedgehog in lipoprotein metabolism and uptake, as well as the normal cellular function of hedgehog in adult intestinal epithelial tissue. Such methods can be used in cell culture but also can be used through administration to animals, for example, In the creation of transgenic mice. The lipid modulators may also be useful in modulating the effects of a high fat diet in subjects, and thus, alter the progression of atherosclerosis. In another example, lipid modulators such as hedgehog agonists or antagonists would also be useful in modulating synthesis of apolipoproteins, VLDL, IDL. LDL and HDL in enterocytes or the liver.

The following well known and well used animal models are suitable for testing the efficacy of the lipid modulators. An apolipoprotein-deficient mouse that synthesizes a truncated apolipoprotein has been generated by Homanics et al. (*Proc. Natl. Acad. Sci. USA* 1993 90:2389–2393) using gene targeting in mouse embryonic stem cells. These mice have reduced apo-B mRNA levels in both the intestines and liver, as well as reduced plasma levels of apo-B, cholesterol, and tricylglycerols. A apolipoprotein knockout mouse or animal model for hypobetalipoproteinemia was developed by Farese et al. (*Proc. Natl. Acad. Sci. USA* 1995 92:1774–1778) using an insertional disruption of the 5' region of the mouse apolipoprotein gene. Both of these mice exhibit reductions in plasma levels of cholesterol and lipoproteins, combined with apparent protection from diet-induced hypercholesterolemia. Thus, either of these animals models should be useful for studying the effects of lipid modulators on lipid metabolism and/or storage. These animal models would also be useful in testing the efficacy of the lipid modulators on lipid metabolism and/or storage.

Another animal model for aberrant expression of apolipoprotein and atherosclerosis was generated by both McCormick et al. (*J. Biol. Chem.* 1996 271:11963–11970) and Callow et al. (*Proc. Natl. Acad. Sci. USA* 1994 91:2130–2134). Both groups used a P1 bacteriophage clone that caused the mice to express high levels of murine apolipoprotein. These transgenic mice develop severe atherosclerotic lesions in response to high fat diets. (Purcell-Huynh et al. *J. Clin. Invest.* 1995 95:2246–2257). Thus, this animal model, as well as similar model developed by Davidson et al. (Nature Medicine. 1998 4: 934–938) would be useful for studying the effects of lipid modulators on lipid metabolism and storage, as well as atherosclerosis,. These animal models would also be useful in testing the efficacy of the lipid modulators on lipid metabolism and storage, as well as atherosclerosis. Other animal models of atherosclerosis, for example, Apolipoprotein E deficent and LDL receptor deficent mice (Science. 1996 272: 685–688) will be useful in testing the efficacy of the lipid modulators on lipid metabolism and storage, as well as atherosclerosis.

B. Therapeutic Applications

In therapeutic applications, lipid modulators such as the hedgehog agonists and antagonists described herein are used in a manner appropriate to general use and can be formulated in a variety of loads of administration, including systemic and localized administration. Techniques and formulations generally may be found in *Remington's Pharmaceutical Sciences*, Meade Publishing Co., Easton Pa. For systemic administration, injection is preferred, including intramuscular, intravenous, intraperitoneal and subcutaneous. Liquid solutions of either the agonist or antagonist can be formulated, preferably in physiologically compatible carrier such as Hanks' solution or Ringer's solution. Lyophilized forms are also included.

In particular, the lipid modulators to be used in therapy will be formulated and dosages established in a fashion consistent with good medical practice taking into account the disorder to be treated, the condition of the individual patient, the site of delivery of the isolated polypeptide, the method of administration and other factors known to practitioners. Therapeutic administration of the lipid modulators of this invention is preferably via parenteral delivery, including subcutaneous, intravenous, intramuscular, intra-articular, intra-synovial, intrasternal, intrathecal, intrahepatic, intralesional and intracranial injection or infusion techniques. Alternative routes include tablets and the like, commercially available nebulizers for liquid formulations, and inhalation of dry powder, lyophilized or aerosolized liposomes. Liquid formulations may be utilized after reconstitution from powder formulations or developed into creams for topical application.

The lipid modulators described herein can be administered as a sterile pharmaceutical composition containing a pharmaceutically acceptable carrier, which may be any of the numerous well known carriers, such as water, saline, phosphate buffered saline, dextrose, glycerol, ethanol, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat and the like, or combinations thereof.

The dose administered will be dependent upon the properties of the lipid modulator employed, e.g. its binding activity and in vivo plasma half-life, the concentration of the lipid modulator in the formulation, the administration route, the site and rate of dosage, the clinical tolerance of the patient involved, the pathological condition afflicting the patient and the like, as is well known within the skill of the physician. Generally, doses of from about 0.5×10–6 molar or less of protein per patient per administration are preferred, although the dosage will certainly depend on the nature of the protein. Different dosages may be utilized during a series of sequential administrations.

It is obvious from the experimentation included herewith that the hedgehog signaling pathway plays a role in the metabolism and storage of lipids and related molecules. The lipid modulators of the present invention may be particularly useful for treating those medical conditions characterized by aberrant expression of hedgehog protein or, more generally, for treating any condition in which it desired to alter by either agonizing or antagonizing the hedgehog signaling pathway.

As but one example of the application of the lipid modulators of this invention in a therapeutic context, lipid modulators such as agonists or antagonists can be administered to patients suffering from a variety of lipid metabolism or storage disorders of the gastrointestinal tract. Certain lipid modulators may be involved in the regulation of apolipoprotein expression. Lipid modulators of the present invention, therefore, may be of use in the treatment of, for instance, lipid transport defects, diet-induced hypercholesterolemia, obesity, and the reduction of plasma cholesterol.

The lipid modulators of the present invention may also be formulated and linked to detectable markers, such as fluoroscopically or radiographically opaque substances, and administered to a subject to allow imaging of tissues. The lipid modulators may also be bound to substances, such as horseradish peroxidase, which can be used as immunocytochemical stains to allow visualization of areas of hedgehog ligand-positive cells on histological sections.

B. Gene Therapy

The lipid modulators of the present invention can also be used as a part of a gene therapy protocol to deliver polynucleotides encoding these lipid modulators. The invention features expression vectors for in vivo transfection and expression of lipid modulators in particular cell types so as to alter the function of the hedgehog signaling pathway in a cell. Expression constructs of lipid modulators may be administered in any biologically effective carrier, e.g. any formulation or composition capable of effectively delivering the lipid modulator to cells in vivo.

Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of polynucleotides into a cell is by use of a viral vector containing polynucleotide, e.g. a cDNA, encoding the desired lipid modulator polypeptide. Infection of cells with a viral vector has the advantage that a large proportion of the targeted cells can receive the polynucleotide. Additionally, molecules encoded within the viral vector, e.g., by a cDNA contained in the viral vector, are expressed efficiently in cells which have taken up viral vector polynucleotide.

A variety of viral vectors can be used as a recombinant gene delivery system for the transfer of exogenous genes in vivo, particularly into humans. These vectors provide efficient delivery of genes into cells, and the transferred polynucleotides can be stably integrated into the chromosomal DNA of the host. For review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses are well known to those skilled in the art. Examples of suitable packaging virus lines for preparing both ecotropic and amphotropic retroviral systems include Crip, Cre2 and Am. Retroviruses have been used to introduce a variety of genes into many different cell types, including epithelial cells, in vitro and/or in vivo. See for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573.

Another viral gene delivery system useful in the present invention utilizes adenovirus-derived vectors. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. See Rosenfeld et al, (1992), supra.

Yet another viral vector system useful for delivery of the lipid modulators is the adeno-associated virus (AAV). Adeno-associated virus is a naturally occurring defective virus that requires another virus, such as an adenovirus or a herpes virus, as a helper virus for efficient replication and a productive life cycle. For a review see Muzyczka et al. Curr. Topics in Micro. and Immunol. (1992) 158:97–129. A variety of polynucleotides have been introduced into different cell types using AAV vectors. See, for example, Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al.(1993) J. Biol. Chem. 268:3781–3790).

In addition to viral transfer methods, such as those illustrated above, non-viral methods can also be employed to cause expression of lipid modulator in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject lipid modulator gene by the targeted cell. Exemplary gene delivery systems of this type include liposomal derived systems, poly-lysine conjugates, and artificial viral envelopes, and tat protein-derived conjugates. See U.S. Pat. No. 5,747,641. In a representative embodiment, a gene encoding antagonist polypeptide can be entrapped in liposomes bearing positive charges on their surface (e.g., lipofectins) and (optionally) which are tagged with antibodies against cell surface antigens of the target tissue (PCT publication WO91/06309; Japanese patent application 1047381; and European patent publication EP-A-43075).

In clinical settings, the gene delivery systems for the therapeutic lipid modulators can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (U.S. Pat. No. 5,328,470) or by stereotactic injection, e.g. Chen et al. (1994) Proc. Nat. Acad. Sci. USA 91: 3054–3057.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Exemplification

The invention now being generally described, it will be more readily understood by reference to the following examples which are included merely for purposes of illustration of certain aspects and embodiments of the present invention, and are not intended to limit the invention.

EXAMPLE 1

Materials and Methods 1.1 Animal Housing and Treatment

Pregnant mice (C57BL/6 or BALB/c) are either purchased (Jackson Laboratory, Bar Harbor, Me.) or matings set up in the mouse facility at Biogen, Inc. Pregnant mice at E12.5 of gestation are injected with 200 ug antibodies once every two days (6 mg/kg) by i.v. injection. The subsequently born offspring continue to receive injections (3 mg/kg) once every two days intraperitoneally (i.p.) until the time of sacrifice. In some experiments, mice receive injections only after birth (postnatal day 1) and followed the same injection regimens as the prenatal injections described above.

In experiments with adult mice that receive treatment only postnatally, two groups, each containing twenty (20) BALB/c mice (Jackson Labs, Bar Harbor Ma.) were maintained under standard laboratory conditions. The two groups were divided into two main sections, dependent upon treatment. Group A mice are treated with hedgehog antagonist, while group B are treated with hedgehog agonist. All injections completed on group A and group B, whether antagonist or agonist, are 8 mg/kg. Each group (A and B) are further divided into four sections of five (5) mice each (group A1, A2, A3, and A4; B1, B2, B3, and B4). Group A1 and B1 are fed with a low-fat diet (5% fat) and injected (IP) with control reagents. Group A2 and B2, are fed a low-fat diet and injected (IP) with either hedgehog antagonist or agonist. Group A3 and B3 are fed a high-fat diet (20% fat) and injected with control reagents. Group A4 and B4 were fed a high-fat diet and injected (IP) with hedgehog antagonist or agonist. The mice continue to receive injections for eighteen weeks.

After sacrifice, the GI tract (duodenum, jejunum, ileum and cecum) is removed and ixed in formalin. Paraffin-embedded sections of 5 um thickness of the duodenum, ejunum, ileum and cecum are prepared and subjected to a hematoxylin and eosin staining H&E staining). (Luna: *Manual of Histological Staining Methods of the Armed Forces stitute of Pathology*; pg. 38–40 1960)

The samples of GI tract are also subject to electron microscopic analysis. Secifically, 5 mm of GI tract samples (duodenum, jejunum, ileum and cecum) are fixed with 1.25% formaldehyde, 2.5% glutaraldehyde, 0.03% picric acid, 100 mM cacodylate buffer, pH=7.2 for 2 hrs at RT, then washed and replaced with PBS for EM analysis. To determine whether there was accumulation of lipid molecules within the enterocytes, Oil-O Red analysis is performed. This type of staining is directed to the detection of lipid molecules, e.g. triglycerides and cholesteryl oleate. (Luna, Id at 187.) For Oil-O Red analysis, cyrosections of approximately 4 um of jejunum are fixed in 4% paraformaldehyde/PBS, PH=7.0 for 5 min and rinsed with PBS 3x, 5 min. Sections are then incubated with 100% Propylene Glycol, 2 min, RT, then 0.5% Oil-Red O/ 100% Propylene Glycol for 30 min at RT, then 85% Propylene Glycol for 1 min at RT, washed 5x with ddH2O, 5 min. The mAb SE1 treated sections are counterstained with Mayers Hematoxylin for 2 min, washed with tap water and mounted with Crystal/Mount (Biomeda Corp.). The intestinal tissues of certain mice embryos are embedded in OCT™ medium (Tissue-Tek, Torrance, Calif.) and immunochemistry performed to detect the binding patterns of injected antibodies. Only anti-hedgehog mab SE1, but not control mab 1E6, bound specifically to the epithelial layers of the intestine (photographs not presented here).

In further experiments, mice in which expression of a beta-galactosidase gene was controlled by a promoter for patched (the receptor for hedgehog), are injected with either control mab 1E6 or anti-hedgehog mab SE1 at postnatal days 8, 10, 12. Mice are sacrificed at day 14 at which time the ileum, cecum and colon are collected and subject to whole-mount x-gal staining, sectioned and subject to eosin stain. We found that expression levels of patched (as reflected by the intensity of the x-gal stain) was reduced in the 5E1 treated cells as compared to the control treated mice (photographs not presented here). This indicates a specific modulation of the hedgehog signalling pathway by SE1 mab.

1.2 Discussion

The mice treated with mAb SE1 generally exhibited a lipid metabolism disorder located in the GI tract, as evidenced by their failure to thrive and early death. Pregnant mice at E12.5 of gestation were injected intravenously with blocking anti-hh monoclonal antibodies once every two days (6 mg per kg). After birth, the offspring continued to receive mAb intraperitoneously (IP) (3 mg/kg) every other day until the time of sacrifice. There was an apparent progressive runting of the SE1 injected mice at day 3 and day 6 as compared to the 1E6 injected mice (photographs not presented here). In separate experiments, newborn mice (Day 1) injected with blocking mAb 5E1 also exhibited runting by day 14 as compared to control 1E6 mAb-injected mice (photographs not presented here). Thus, both prenatal (E12–E18) and postnatal (NB to day 3) treatment with 5E1 resulted in failure to thrive, runting, diarrhea and death before weaning.

Histological analysis revealed prominent apical or subnuclear vacuole formation in intestinal epithelial cells (enterocytes) only in the mice after birth and older (photographs not presented here). Other cell types of the GI tract, as well as histology of other major organs appeared to be histologically normal as assessed by two pathologists. Specifically, vacuolation of the enterocytes was confirmed by EM analysis. Myofibroblasts with a normal patched-1 receptor were present. Furthermore, regeneration and migration of enterocyte precursors to surface epithelial cells occurred, as confirmed by pulse-chase BrdU labeling. A TUNEL assay showed no increase in rate of cell death. Finally, the negative staining of PAS in these vacuoles suggested that developmental lineage commitment of epithelial/goblet cells occurred properly.

Specifically, hematoxylin and Eosin (H&E) staining of the GI tract tissue sections on postnatal mice (day 17) that received mAb injections starting from postnatal day 2 (D2) and every other day afterward until the time of sacrifice, revealed vacuolation of enterocytes only in the blocking anti-hh mAb 5E1 treated GI tract sections and not in the control 1E6 treated sections (photographs not presented here). When mice were injected with mAbs starting at postnatal day 1 and the representative ileum and ceca regions of the GI tract were subjected to electron microscopic (EM) analysis, vacuolation in enterocytes appears at day 11 to day 15 only in blocking mAb SE1-treated enterocytes but not in mAb 1E6 controls (photographs not presented here). In these same mice, analyses with Oil Red O for staining of lipid (triglycerides and cholesteryl oleate) revealed only scattered, punctuated Oil Red O staining along the control mAb 1E6-treated enterocytes in contrast to vacuoles in the enterocytes of the blocking anti-hh mAb 5E1 treated mice which were filled with Oil Red O positive lipids (photographs not presented here)

EXAMPLE 2

Evaluation of Weight Loss in Mice Subject to the Modulating Effect of a Hedgehog Antagonist Three week old BALB/c mice (n=4) and 16 week old BU6 mice (n=4) are injected with control 1E6 mab or hedgehog antagonist SE1 mab (8 mg/kg; three times per week) for 18 weeks. Mice are subject to either chow diet or high fat diet (19.2% fat) from the beginning of antibody treatments. Body weight is measured every week and is shown in FIG. 1 as a percentage of weight change as compared to the first weeks weight post treatment. There is a high-fat diet dependent weight loss only in the anti-hedgehog 5E1 treated group. Lipid accumulation (as evidenced by oil staining) was only observed in this group of mice.

EXAMPLE 3

Evaluation of the Modulating Effect of a Hedgehog Antagonist on Obese Mice

Figure 2:
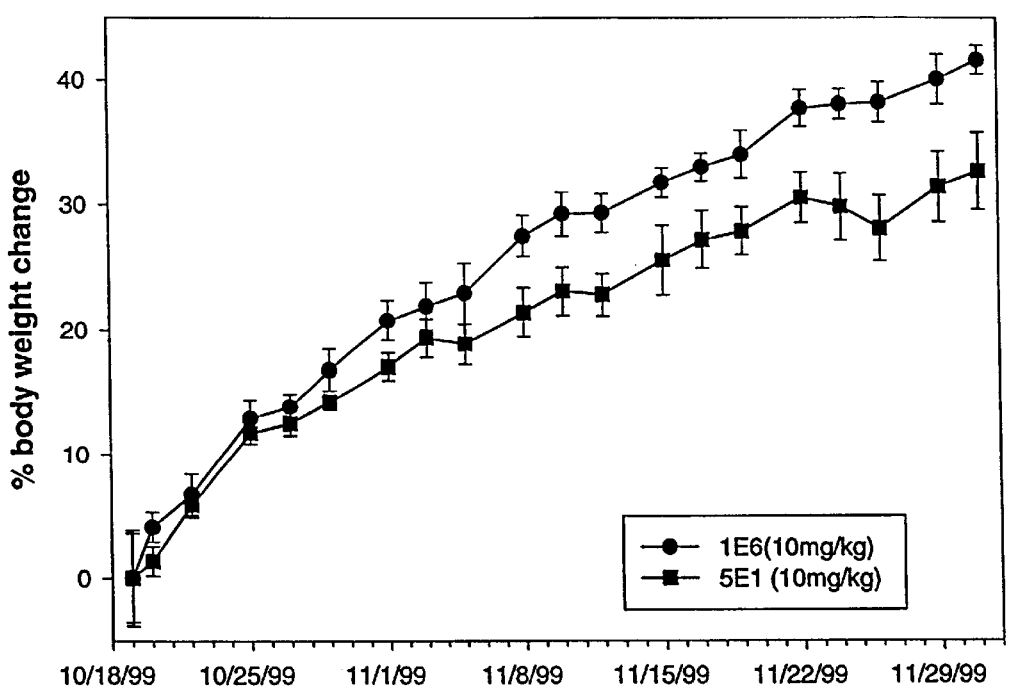
FIG. 2: Six week old obese mice were treated with 1E6 or 5E1 mabs (10 mg/kb; three times per week) for 6 weeks and the body weight measured before each injection. The body weight is indicated as the percentage of weight change as compared to the original weight of the animal prior to the first injection.

A strain of obese mice with a leptin gene mutation are obtained from Jackson Laboratory (Bar Harbor, Ma.). Six week old obese mice are treated with 1E6 or SE1 mabs (10 mg/kg; three times per week) for 8 weeks and the body weight measured before each injection (FIG. 2). The body weight is indicated as the percentage of weight change as compared to the original weight of the animal prior to the first injection. Treatment with hedgehog antagonist results in significant weight loss in the obese mice.

EXAMPLE 4

Evaluation of the Modulating Effect of a Hedgehog Antagonist or Agonist on Mice Prone to Apolipoprotein Deficiency and Atherosclerosis Eight groups, each containing 15 atherogenic prone, Apo-E deficient mice (8 weeks old) are maintained under standard laboratory conditions. The treatments are:

Group 1 (n=15), mice under low-fat diet and injected (i.p) with 200 ug of control Ab;

Group 2 (n=15), mice under low-fat diet and injected (i.p) with 200 ug of anti-hh mAb;

Group 3 (n=15), mice under high-fat diet and injected (i.p) with 200 ug of control Ab; and Group 4 (n=15), mice under high-fat diet and injected (i.p) with 200 ug of anti-hh mAb;

Group 5 (n=15), mice under high-fat diet and injected (i.p) with 200 ug of a hedgehog agonist; and Group 6 (n=15), mice under high-fat diet and injected (i.p) with control reagent for hedgehog agonist; and Group 7 (n=15), mice under low-fat diet and injected (i.p) with 200 ug of a hedgehog agonist; and Group 8 (n=15), mice under low-fat diet and injected (i.p) with control reagent doe hedgehog agonist.

The mAbs are administered every other day, while the hedgehog agonists are administered everyday. The low-fat diet refers to the standard chow (5% fat), the high fat (atherogenic) diet is purchased from ICN (Costa Mesa, Calif.)(17.8% fat and 1.23% cholersterol and others). Both the injections and the high-fat diet treatments are continued for 18 weeks at which point, they are sacrificed. After sacrifice, the aortas are removed and fixed with formalin and stained with Sudan IV and the atherosclerotic plaque area are measured. Histopathological examination of tisuues is also done on H&E sections.

What is claimed is:

1. A method for decreasing lipid absorption in an animal comprising administering to the animal an amount of an anti-hedgehog antibody effective to decrease lipid absorption in said animal.

2. A method of increasing lipid accumulation in vacuoles in intestinal epithelial cells in an animal comprising administering to the animal an amount of an anti-hedgehog antibody effective to increase the lipid accumulation in vacuoles in intestinal epithelial cells.

3. A method for increasing the accumulation of fat in intestinal epithelial cells in an animal comprising administering to the animal an amount of an anti-hedgehog antibody effective to increase the accumulation of fat in intestinal epithelial cells.

4. The method according to any one of claims 1–3, wherein the anti-hedgehog antibody is selected from:

(a) a human antibody or an active fragment thereof;

(b) a chimeric antibody or an active fragment thereof;

(c) a humanized antibody or an active fragment thereof.

5. The method according to any one of claims 1–3, wherein the animal is a mammal.

6. The method according to claim 5, wherein the mammal is a human.

7. A method of inducing weight loss in an animal comprising administering to the animal an amount of an anti-hedgehog antibody effective to decrease the weight of said animal.

8. The method of claim 7, wherein said animal is obese.

* * * * *